(12) United States Patent
Zlatev et al.

(10) Patent No.: US 12,018,260 B2
(45) Date of Patent: Jun. 25, 2024

(54) TUNABLE REVERSIR™ COMPOUNDS

(71) Applicant: ALNYLAM PHARMACEUTICALS, INC., Cambridge, MA (US)

(72) Inventors: Ivan Zlatev, Cambridge, MA (US); Adam Castoreno, Cambridge, MA (US); Martin Maier, Cambridge, MA (US); Vasant Jadhav, Cambridge, MA (US); Jae Kim, Cambridge, MA (US); Pushkal Garg, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 17/583,931

(22) Filed: Jan. 25, 2022

(65) Prior Publication Data
US 2023/0029227 A1 Jan. 26, 2023

Related U.S. Application Data

(63) Continuation of application No. 16/636,255, filed as application No. PCT/US2018/046904 on Aug. 17, 2018, now abandoned.

(60) Provisional application No. 62/546,779, filed on Aug. 17, 2017.

(51) Int. Cl.
*C12N 15/113* (2010.01)
*A61K 31/702* (2006.01)

(52) U.S. Cl.
CPC .......... *C12N 15/113* (2013.01); *A61K 31/702* (2013.01); *C12N 2310/11* (2013.01); *C12N 2310/14* (2013.01); *C12N 2310/315* (2013.01); *C12N 2310/3231* (2013.01); *C12N 2310/3515* (2013.01)

(58) Field of Classification Search
None
See application file for complete search history.

(56) References Cited

U.S. PATENT DOCUMENTS

| | | |
|---|---|---|
| 7,300,922 B2 | 11/2007 | Sullenger et al. |
| 8,361,980 B2 | 1/2013 | Kauppinen |
| 8,389,488 B2 | 3/2013 | Monia et al. |
| 9,181,549 B2 | 11/2015 | Prakash et al. |
| 9,334,497 B2 | 5/2016 | Hutvagner et al. |
| 2009/0298916 A1 | 12/2009 | Kauppinen et al. |
| 2010/0184822 A1 | 7/2010 | Sullenger et al. |
| 2011/0172292 A1 | 7/2011 | Hansen et al. |
| 2016/0319279 A1 | 11/2016 | Hutvagner et al. |
| 2017/0368972 A1 | 12/2017 | Fujikake et al. |

FOREIGN PATENT DOCUMENTS

| | | |
|---|---|---|
| WO | 2009043353 A2 | 4/2009 |
| WO | 2009061841 A2 | 5/2009 |
| WO | 2014076195 A1 | 5/2014 |
| WO | 2016100716 A1 | 6/2016 |
| WO | 2016161388 A1 | 10/2016 |

OTHER PUBLICATIONS

Haraguchi et al., "A potent 2'-O-methylated RNA-based microRNA inhibitor with unique secondary structures", Nucleic Acids Research 40(8):e58 (2012). (13 pages).
Jackson et al., "Recognizing and avoiding siRNA off-target effects for target identification and therapeutic application", Nature Reviews Drug Discovery 9:57-67 (2010).
Kauppinen et al., "Locked nucleic acid (LNA): High affinity targeting of RNA for diagnostics and therapeutics", Drug Discovery Today: Technologies 2(3):287-290 (2005).
Krutzfeldt et al., "Specificity, duplex degradation and subcellular localization of antagomirs", Nucleic Acids Research 35(9):2885-2892 (2007).
Nair et al., "Multivalent N-Acetylgalactosamine-Conjugated siRNA Localizes in Hepatocytes and Elicits Robust RNAi-Mediated Gene Silencing", Journal of the American Chemical Society 136:16958-16961 (2014).
Meister et al., "Sequence-specific inhibition of mircoRNA- and siRNA-induced RNA silencing." RNA 10:544-550 (2004).
US Food and Drug Administration "Guidline for industry structure and content of clinical study reports". [date verified by web.archive.erg; retrieved on Nov. 5, 2018]. Retrieved from the Internet: <URL:https://www.fda.gov/downloads/drugs/guidancecomplianceregulatoryinformation/guidances/ucm073113.pdf> (1996).
Zlatev "Reversir Platform for Rapid and Potent Reversal of siRNA Silencing Activity." Presentation [online]. 11th Annual Meeting of the OTS. Oct. 13, 2015 (Retrieved on Nov. 2, 2018). Retrieved from the Internet: <URL: http://www.alnylam.com/web/assets/Reversir_OTS_ 101315.pdf>.
"Sarett ""Hydrophobic Modification of siRNA to Improve Delivery and Efficacy of RNAI Therapeutics"". Dissertation [online]. Vanderbilt University. May 2017 (Retrieved on Nov. 6, 2018). Retrieved from the Internet: <URL: https://etd .library. vanderbilt .edu//available/etd-03272017155710/unrestricted/ssarettDissertationFinalETD.pdf>nFinalETD.pdf>".
Zlatev et al. "Reversal of siRNA-mediated gene silencing in vivo." Nature Biotechnology 36: 1-20 (2018) [Includes Reporting Summaries and Supplementary Figures].
Scanlon "Anti-genes: siRNA, ribozymes and antisense". Current Pharmaceutical Biotechnology 5:415-420 (2004).

*Primary Examiner* — Brian Whiteman
(74) *Attorney, Agent, or Firm* — Nixon Peabody LLP; David S. Resnick; Ravinderjit S. Braich

(57) ABSTRACT

The present invention relates, in general to agents that modulate the pharmacological activity of siRNAs. In addition, the invention relates generally to methods and systems for use in assessing the efficacy and safety of a pharmaceutical composition for use in the treatment or prophylaxis of a disease.

19 Claims, 19 Drawing Sheets
Specification includes a Sequence Listing.

TUNABLE REVERSIR™ COMPOUNDS

CROSS REFERENCE TO RELATED APPLICATION

This application is a continuation under 35 U.S.C. § 120 of copending U.S. application Ser. No. 16/636,255 filed Feb. 3, 2020, which is a 371 National Phase Entry of International Patent Application No. PCT/US2018/046904 filed Aug. 17, 2018, which designated the U.S. and which claims the benefit under 35 U.S.C. § 119(e) of the U.S. Provisional Application No. 62/546,779 filed Aug. 17, 2017, the content of which is incorporated herein by reference in its entirety.

SEQUENCE LISTING

The sequence listing of the present application has been submitted electronically via EFS-Web as an ASCII formatted sequence listing with a file name 051058-090110WOPT-SL.txt, creation date of Jan. 31, 2020 and a size of 18,390 bytes. The sequence listing submitted via EFS-Web is part of the specification and is herein incorporated by reference in its entirety.

TECHNICAL FIELD

The present disclosure relates generally to oligomeric compounds (oligomers), which target siRNAs (e.g. conjugated or unconjugated siRNAs) in vivo, thereby providing a method for the tailored control of RNAi pharmacology and therefore of the therapeutic activity and/or side effects of siRNA-based therapeutics in vivo. The present invention also relates generally to methods and systems for use in assessing the efficacy and safety of a pharmaceutical composition for use in the treatment or prophylaxis of a disease.

BACKGROUND

In recent years, safety and efficacy data from a number of investigational clinical studies have generated growing evidence for the therapeutic potential of RNA interference (RNAi). The short interfering RNA (siRNA) molecules that utilize the endogenous RNAi pathway can potently and specifically silence mRNAs, thereby preventing the formation of disease causing or disease pathway implicated proteins. Targeted delivery of RNAi therapeutics to liver hepatocytes is achieved by conjugating chemically modified siRNAs to a trivalent N-acetylgalactosamine (GalNAc) ligand, which facilitates asialoglycoprotein receptor (ASGPR)-mediated tissue specific uptake. The development of GalNAc-siRNA conjugates with enhanced stabilization chemistry has led to substantial improvements in efficacy and duration. In preclinical animal models, as well as in humans, GalNAc-siRNA conjugates have demonstrated impressive duration of action following a single subcutaneous administration, with potent silencing sustained for several months. With their extended duration of action, RNAi therapeutics can benefit from a technology that enables rapid reversal of silencing activity and provides tailored control over RNAi pharmacology, a desired attribute for personalized precision medicines.

SUMMARY OF THE INVENTION

The inventors surprisingly found that the right level in modulation of a tunable REVERSIR™ agent is required to effectively revive the RNAi activity of a siRNA compound after redosing of the same siRNA compound. Tunable duration of REVERSIR™ action is achieved through optimization of design parameters allowing for effective resumption of RNAi pharmacology after redosing with the same siRNA, therefore providing off-rate and on-rate control in modulating the therapeutic activity of siRNA therapeutics in vivo. The tunable duration properties of tunable REVERSIR™ agents can be extended to the control of siRNA efficacy in the design of clinical trials with siRNA therapeutics in humans.

In certain embodiments, the present invention provides tunable REVERSIR™ compounds comprising a modified oligonucleotide consisting of 8-10 linked nucleotides (e.g. 8, 9 or 10) and having a nucleobase sequence substantially complementary to at least one strand of siRNA compounds (e.g. conjugated or unconjugated siRNA). In some embodiments, the tunable REVERSIR™ compounds comprise a modified oligonucleotide consisting of 8-10 (e.g. 8, 9 or 10) linked nucleotides and having a nucleobase sequence substantially complementary to the antisense strand of siRNA compounds. In some other embodiments, the tunable REVERSIR™ compounds comprise a modified oligonucleotide consisting of 8-10 (e.g. 8, 9 or 10) linked nucleotides and having a nucleobase sequence substantially complementary to the sense strand of siRNA compounds.

In certain such embodiments, the modified oligonucleotide is a single-stranded oligonucleotide and/or is at least 90% complementary to at least one strand of the siRNA. In some embodiments, the modified oligonucleotide is a single-stranded oligonucleotide and/or is at least 90% complementary to the antisense strand of the siRNA. In some other embodiments, the modified oligonucleotide is a single-stranded oligonucleotide and/or is at least 90% complementary to the sense strand of the siRNA.

In certain embodiments, the tunable REVERSIR™ compound is fully complementary to at least one strand of the conjugated or unconjugated siRNA. In some embodiments, the tunable REVERSIR™ compound is fully complementary to the antisense strand of the siRNA. In some other embodiments, the tunable REVERSIR™ compound is fully complementary to the sense strand of the siRNA.

In certain embodiments, tunable REVERSIR™ compounds comprise at least one modified internucleotide or intersugar linkage. In certain such embodiments, at least one (e.g., one, two, three, four, five, six, and including all) internucleotide linkage is a phosphorothioate internucleotide linkage.

In certain embodiments, tunable REVERSIR™ compounds comprise at least one nucleotide comprising a modified sugar. In certain such embodiments, the modified sugar is a bicyclic sugar or sugar comprising a 2'-O-methyl or a 2'-O-methoxyethyl.

In certain embodiments, tunable REVERSIR™ compounds comprise one or more (e.g., one, two, three, four, five, six, seven, eight, nine, or ten) locked nucleic acid (LNA) monomers.

In some embodiments, each nucleotide in the tunable REVERSIR™ compound is a 2'modified nucleotide and the tunable REVERSIR™ compound comprises at least one (e.g., one, two, or three) G-clamp nucleobases.

In certain embodiments, tunable REVERSIR™ compounds of the invention further comprise at least one nucleotide comprising a modified nucleobase. In certain such embodiments, the modified nucleobase is a 5-methylcytosine, 5-methyluracil, or 2,6-diaminopurine.

In certain embodiments, tunable REVERSIR™ compounds comprise at least one modification. In certain such embodiments, tunable REVERSIR™ compounds comprise one or more nucleotide modifications and or one or more linkage modifications. In certain embodiments, tunable REVERSIR™ compounds comprise one or more modifications selected from: sugar modifications, linkage modifications, nucleobase modifications, conjugates (e.g., ligands), and any combinations thereof.

In certain embodiments, the present invention provides tunable REVERSIR™ compounds comprising of 8 or 9 modified nucleotides.

In certain embodiments, the present invention provides tunable REVERSIR™ compounds consisting of 8 or 9 modified nucleotide nucleotides and a DNA nucleotide linker at the 3'-end of tunable REVERSIR™, connecting the molecule to the 3'-GalNAc ligand.

In certain embodiments, the tunable REVERSIR™ compound comprising at least three (three or four) LNA nucleotides and one of the LNA nucleotides is base paired with the $6^{th}$ nucleotide from the 5'-end of the target strand of the siRNA.

In certain embodiments, the tunable REVERSIR™ of the invention further comprises not more than three or four phosphorothioate (PS) backbone modifications.

In certain embodiments, tunable REVERSIR™ compounds modulate the RISC pathway. In some embodiments, tunable REVERSIR™ compounds inhibit the RISC pathway.

In certain embodiments, the invention provides a composition comprising a tunable REVERSIR™ compound or a pharmaceutically acceptable salt thereof and a pharmaceutically acceptable carrier or diluent.

In certain embodiments, the activity of siRNA is counteracted by oligomeric tunable REVERSIR™ compound according to the present invention. In certain embodiments, at a later timepoint following the time of administration of oligomeric tunable REVERSIR™ compound, the oligomeric tunable REVERSIR™ compound's action of reducing the activity of an siRNA is counteracted by the administration of the same siRNA.

In certain embodiments, the action of tunable REVERSIR™ compound allows on-drug and off-drug control of the therapeutic action of an siRNA drug, where the sequence of on-drug and off-drug action of the siRNA can be performed by the sequential administration of the tunable REVERSIR™, preceded and/or followed by the administration of the therapeutic siRNA.

In certain embodiments, the invention provides methods of inhibiting RNAi activity of a conjugated or unconjugated siRNA in a cell. The method, generally, comprises contacting the cell with a tunable REVERSIR™ compound according the present invention and thereby inhibiting the RNAi activity in the cell. In certain such embodiments, the cell is in vivo. In some embodiments, the cell is in vitro. In some embodiments the cell is ex vivo. In some embodiments, the cell is in a subject. In some further embodiments of this, the cell is an animal. In certain embodiments, the animal is a human.

In certain embodiments, the invention provides methods comprising: contacting a cell with a conjugated or unconjugated siRNA; detecting RNAi activity; and contacting the cell with a tunable REVERSIR™ compound. In certain embodiments, the method of detecting the RNAi activity comprises measuring the amount of target mRNA present, the amount of target protein present, and/or the activity of a target protein. In certain embodiments, such methods comprise detecting tunable REVERSIR™ activity by measuring RNAi activity after contacting the cell with the tunable REVERSIR™ compound. In certain such methods, the cell is in vivo. In some embodiments, the cell is in an animal. In certain embodiments, the animal is a human.

In certain embodiments, the invention provides methods of ameliorating a side-effect of siRNA treatment comprising: contacting a cell with a conjugated or unconjugated siRNA; detecting a side-effect; contacting the cell with a tunable REVERSIR™ compound; and thereby ameliorating the side effect of the siRNA, an endogeneous, an exogenous micro-RNA, or combinations thereof.

In certain embodiments, the invention provides methods of treating a patient comprising: administering to the patient a conjugated or unconjugated siRNA; monitoring the patient for siRNA activity; and if the siRNA activity becomes higher than desired, administrating a tunable REVERSIR™ compound. In certain such embodiments, the monitoring siRNA activity comprises measuring the amount of target mRNA present, measuring the amount of target protein present and/or measuring the activity of a target protein. In certain embodiments, such methods include detecting tunable REVERSIR™ activity by measuring siRNA activity after administration of the tunable REVERSIR™ compound. In certain embodiments, the patient is a mammal. In some embodiments, the patient is a human.

In certain embodiments, the invention provides methods of treating a patient comprising: administering to the patient a conjugated or unconjugated siRNA; monitoring the patient for one or more side effect; and if the one or more side effect reaches an undesirable level, administrating a tunable REVERSIR™ compound. In certain embodiments, the patient is a mammal. In some embodiments, the patient is a human.

In certain embodiments, the structure and the properties of the tunable REVERSIR™ compounds are designed as such so that the tunable REVERSIR™ compound will achieve maximal inhibition or reversal of siRNA activity in vivo. For example, maximal inhibition or reversal of siRNA activity occurs when the mRNA levels decreased to at least about 70%, at least about 80%, at least about 90%, at least about 95%, at least about 99%, up to and including 100% and any integer in between 5% and 100%.

In certain embodiments, the structure and the properties of the tunable REVERSIR™ compounds are designed as such so that the tunable REVERSIR™ compound will achieve controlled duration of inhibition or reversal of siRNA activity in vivo. In certain embodiments, the duration is controlled with tunable REVERSIR™ requires designing tunable REVERSIR™ with low phosphorothioates internucleotides and strategic positioning of the LNA modifications within the oligonucleotides.

In certain embodiments the tunable REVERSIR™ comprises not more than five, four or three phosphorothioates, and comprises at least three (three or four) LNA nucleotides and one of the LNA nucleotides is base-paired with the $6^{th}$ nucleotide from the 5'-end of the target strand of the siRNA.

In certain embodiments, the structure and the properties of the tunable REVERSIR™ compounds are designed as such so that the tunable REVERSIR™ compound will enable effective redosing of the siRNA and resumption of RNAi activity in vivo.

The present invention also relates generally to methods for demonstrating efficacy and safety of pharmaceutical compositions for use in the treatment or prophylaxis of diseases, for example disease that is caused by an aberrant expression of a target gene. In particular, it relates to improved methods for demonstration of efficacy and safety in circumstances, wherein the pharmaceutical compositions, such as siRNAs, that have durable pharmacodynamics (PD) and where long term safety and efficacy is preferred in an open-label single-arm clinical trial but not feasible. It also relates to circumstances, such as in orphan diseases, wherein recruitments of patients are difficult, and there are minimal subjects receiving placebo or minimally active treatments which may prevent detection of therapeutic efficacy and safety.

Thus the invention provides various methods and systems for assessing the efficacy and safety of a pharmaceutical composition for use in the treatment or prophylaxis of a disease, the randomized withdrawal method comprising the steps of:

(1) treating all subjects with the pharmaceutical composition for a first treatment time frame,
(2) deriving mRNA level and/or physiological outcome measures for the all subjects, (3) separating the responder members of the treated subjects from the non-responder members,
(4) randomizing and stratifying members of the responders into at least two further sub-groups,
(5) continue treating members of one sub-group in (4) with the pharmaceutical composition, and treating members of the other sub-group with a REVERSIR™ compound of claim 1 for a second treatment timeframe,
(6) deriving mRNA level and/or physiological outcome measures for the sub-groups,
(7) comparing the outcomes at (6) with the outcomes at (2), and
(8) using the comparison in (7) to derive an efficacy and safety measures for the pharmaceutical composition.

In certain embodiments, the invention provides various methods and systems for assessing the efficacy and safety of a pharmaceutical composition for use in the treatment or prophylaxis of a disease, the cross-over method comprising the steps of:

(1) stratifying a subject group into at least two sub-groups,
(2) treating members of one sub-group with the pharmaceutical composition for a first treatment timeframe, and treating members of a second sub-group with a blinded placebo,
(3) deriving mRNA level, and/or biomarker and/or physiological outcome measures for the sub-groups,
(4) treating members of the treated sub-group with a tunable REVERSIR™, and treating members of the other blinded placebo sub-group with the pharmaceutical composition for a second treatment timeframe,
(5) deriving mRNA level and/or physiological outcome measures for the sub-groups,
(6) comparing the outcomes at (5) with the outcomes at (3), and
(7) using the comparison in (6) to derive an efficacy and safety measures for the pharmaceutical composition.

DETAILED DESCRIPTION OF THE INVENTION

Figure 1:
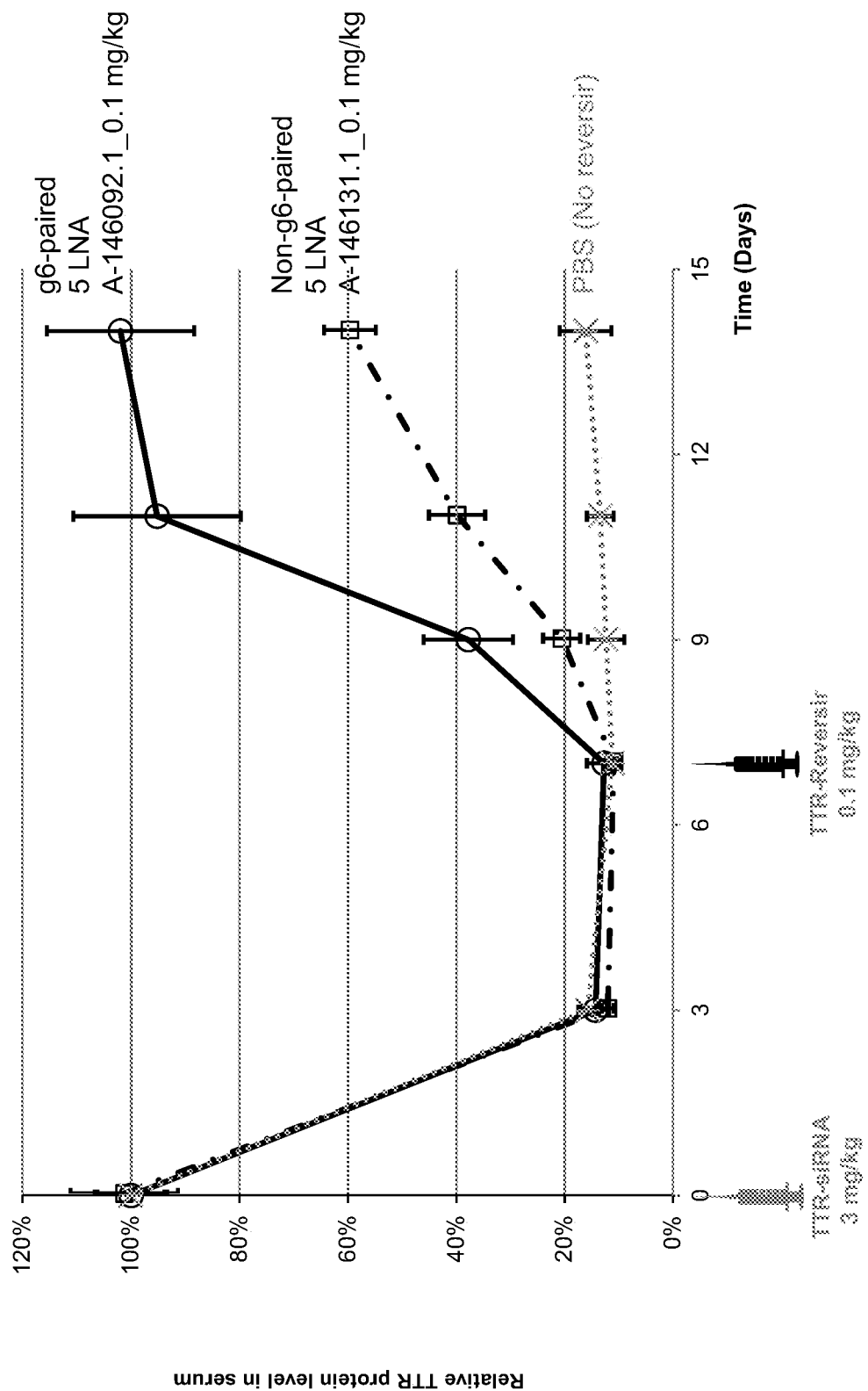
FIG. 1 shows in vivo activity of exemplary 15-mer REVERSIR™ compounds targeting transthyretin-directed (TTR) siRNAs and having different potencies of RNAi activity reversal based on different base pairing with the position g6 in the guide (antisense) siRNA strand (the 6$^{th}$ nucleotide from the 5'-end of the target strand of the siRNA).

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

In certain embodiments, the invention provides a tunable REVERSIR™ compound comprising 8 or 9 modified nucleotides, wherein at least three of the modified nucleotides are high affinity monomers and one of the high affinity monomers is base paired with the 6th nucleotide from the 5'-end of the target strand of the siRNA.

In certain embodiments, the high affinity monomer is an LNA.

In certain embodiments, the tunable REVERSIR™ compound comprising three or four LNA nucleotides.

In certain embodiments, the tunable REVERSIR™ compound is a single-stranded oligonucleotide having at least 90% complementary to the antisense strand.

In certain embodiments, the tunable REVERSIR™ compound is fully complementary to the antisense strand.

In certain embodiments, the tunable REVERSIR™ compound comprises at least one modified internucleotide linkage.

In certain embodiments, the tunable REVERSIR™ compound comprises internucleotide linkage that is a phosphorothioate.

In certain embodiments, the tunable REVERSIR™ compound comprises not more than three or four phosphorothioate modifications.

In certain embodiments, the tunable REVERSIR™ compound is conjugated with a ligand.

In certain embodiments, the tunable REVERSIR™ compound comprises a ligand that is

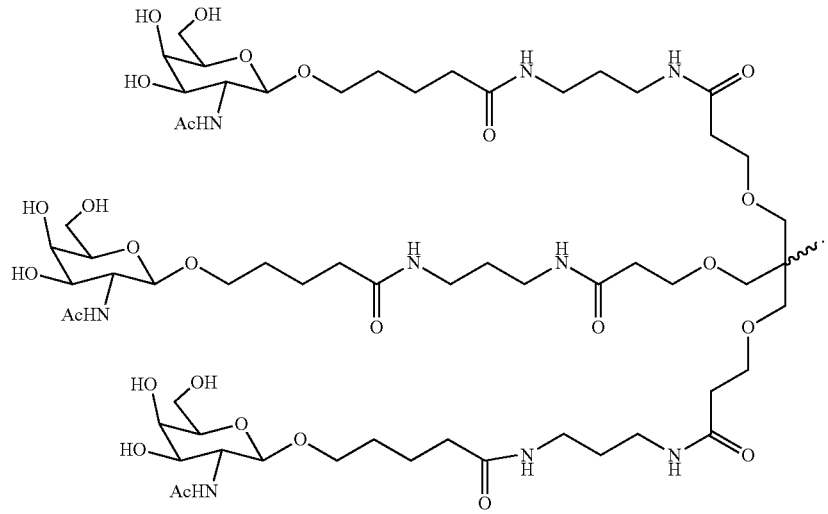

In certain embodiments, the tunable REVERSIR™ compound comprises a ligand is conjugated to 3'-terminus of the compound.

In certain embodiments, the tunable REVERSIR™ compound comprises a deoxy sugar that is a 2'-deoxy ribose.

In certain embodiments, the invention provides a kit comprising the tunable REVERSIR™ compound comprising 8 or 9 modified nucleotides, wherein at least three of the modified nucleotides are high affinity monomers and one of the high affinity monomers is base paired with the 6th nucleotide from the 5'-end of the target strand of the siRNA.

In certain embodiments, the invention provides a kit comprising a siRNA and a tunable REVERSIR™ compound comprising 8 or 9 modified nucleotides, wherein at least three of the modified nucleotides are high affinity monomers and one of the high affinity monomers is base paired with the 6th nucleotide from the 5'-end of the target strand of the siRNA.

In certain embodiments, the invention provides method or a system for assessing the efficacy and safety of a pharmaceutical composition for use in the treatment or prophylaxis of a disease, the method comprising the steps of:
 (1) treating all subjects with the pharmaceutical composition for a first treatment time frame,
 (2) deriving mRNA level and/or physiological outcome measures for the all subjects,
 (3) separating the responder members of the treated subjects from the non-responder members,
 (4) randomizing and stratifying members of the responders into at least two further sub-groups,
 (5) continue treating members of one sub-group in (4) with the pharmaceutical composition, and treating members of the other sub-group with a REVERSIR™ compound of claim 1 for a second treatment timeframe,
 (6) deriving mRNA level and/or physiological outcome measures for the sub-groups,
 (7) comparing the outcomes at (6) with the outcomes at (2), and
 (8) using the comparison in (7) to derive an efficacy and safety measures for the pharmaceutical composition.

In certain embodiments, the invention provides method or a system for assessing the efficacy and safety of a pharmaceutical composition for use in the treatment or prophylaxis of a disease, the method comprising the steps of:
 (1) treating all subjects with the pharmaceutical composition for a first treatment time frame,
 (2) deriving mRNA level and/or physiological outcome measures for the all subjects, (3) separating the responder members of the treated subjects from the non-responder members,
 (4) randomizing and stratifying members of the responders into at least two further sub-groups,
 (5) continue treating members of one sub-group in (4) with the pharmaceutical composition, and treating members of the other sub-group with a REVERSIR™ compound of claim 1 for a second treatment timeframe, (6) deriving mRNA level and/or physiological outcome measures for the sub-groups, (7) comparing the outcomes at (6) with the outcomes at (2), and (8) using the comparison in (7) to derive an efficacy and safety measures for the pharmaceutical composition, wherein the subjects are grouped into four sub-groups, and following a Williams design and randomization in cross-over clinical trials (Journal of Statistical Software, V29, February 2009).

In one example, the number of treatments in the trial is four and with the following sequence treatment:

| SeqNo | Period1 | Period2 | Period3 | Period |
|---|---|---|---|---|
| 1 | Drug2B | Drug1A | ActCtrl | Placebo |
| 2 | ActCtrl | Drug2B | Placobo | Drug1A |
| 3 | Placebo | ActCtrl | Drug1A | Drug2B |
| 4 | Drug1A | Placebo | Drug2B | ActCtrl | wherein Drug1A comprises a pharmaceutical composition at a first dose, Drug2B comprises a pharmaceutical composition at a second dose, ActCtrl comprises a pharmaceutical composition at the original dose, active comparator or other standard of care (i.e. other available treatment(s) for the disease), and Placebo comprises a group with REVERSIR™ treatment.

In certain embodiments, the invention provides a method or a system for assessing the efficacy and safety of a pharmaceutical composition for use in the treatment or prophylaxis of a disease, wherein the disease is caused by an aberrant expression of a target gene.

In certain embodiments, the invention provides a method or a system for assessing the efficacy and safety of a pharmaceutical composition for use in the treatment or prophylaxis of a disease, wherein the pharmaceutical composition comprises an oligonucleotide.

In certain embodiments, the invention provides a method or a system for assessing the efficacy and safety of a pharmaceutical composition for use in the treatment or prophylaxis of a disease, wherein the oligonucleotide is an antisense or a siRNA.

In certain embodiments, the invention provides a method or a system for assessing the efficacy and safety of a pharmaceutical composition for use in the treatment or prophylaxis of a disease, wherein the oligonucleotide provided durable pharmacodynamics.

In certain embodiments, the invention provides a method or a system for assessing the efficacy and safety of a pharmaceutical composition for use in the treatment or prophylaxis of a disease, wherein the tunable REVERSIR™ compound of the invention is used to equalize and enable randomized withdrawal of the treated members.

In certain embodiments, the tunable REVERSIR™ compound of the invention induces washout in the treated sub-group.

In certain embodiments, the tunable REVERSIR™ compound of the invention resets the baseline of the RNAi acidity.

In certain embodiments, the siRNA can be redosed after at least one, two, three, or four weeks after the tunable REVERSIR™ treatment.

In certain embodiments, the target gene is selected from the group consisting of TTR, AGT, ALAS-1, Factor XI, Factor XII, CC5, CC3, GO1, AT3, AAT, Eg5, PCSK9, TPX2, apoB, SAA, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-I gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21 (WAFI/CIPl) gene, mutations in the p27(KIPl) gene, mutations in the PPMlD gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

In certain embodiments, the second timeframe is until the completion of an open-label study.

In certain embodiments, the first timeframe is about one month, two months, or three months.

In certain embodiments, the third timeframe is until the completion of a clinical study.

In certain embodiments, the method or system constitutes a clinical trial or system for performing a clinical trial for testing the pharmaceutical.

In certain embodiments, the method or system is to assess a treatment regime employing the pharmaceutical for its efficacy.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "tunable REVERSIR™" means an oligomeric REVERSIR™ compound that counteract the activity of siRNA with protein recovery level at about 50%, 60%, 70%, 80%, 90%, or complete recovery in about 8, 9, 10, 11, 12, 13, 14 or 15 days. In one embodiment, tunable REVERSIR™ compound counteract the activity of siRNA with complete recovery of protein level in about 8, 9, 10, 11, 12, 13, 14 or 15 days. In one embodiment, tunable REVERSIR™ compound counteract the activity of siRNA with protein recovery level at about 70% in about 9, 10, 11, or 12 days.

In certain embodiments, at a later timepoint following the time of administration of oligomeric tunable REVERSIR™ compound, the oligomeric tunable REVERSIR™ compound's action of reducing the activity of an siRNA is counteracted by the administration of the same siRNA in about 15 to 45 days, preferably in about 37 to 42 days.

As used herein, the term "nucleoside" means a glycosylamine comprising a nucleobase and a sugar. Nucleosides includes, but are not limited to, naturally occurring nucleosides, abasic nucleosides, modified nucleosides, and nucleosides having mimetic bases and/or sugar groups.

As used herein, the term "nucleotide" refers to a glycosomine comprising a nucleobase and a sugar having a phosphate group covalently linked to the sugar. Nucleotides may be modified with any of a variety of substituents.

As used herein, the term "nucleobase" refers to the base portion of a nucleoside or nucleotide. A nucleobase may comprise any atom or group of atoms capable of hydrogen bonding to a base of another nucleic acid.

As used herein, the term "heterocyclic base moiety" refers to a nucleobase comprising a heterocycle.

As used herein, the term "oligomeric compound" refers to a polymeric structure comprising two or more sub-structures and capable of hybridizing to a region of a nucleic acid molecule. In certain embodiments, oligomeric compounds are oligonucleotides. In certain embodiments, oligomeric compounds are oligonucleotides. In certain embodiments, oligomeric compounds are antisense compounds. In certain embodiments, oligomeric compounds are tunable REVERSIR™ compounds. In certain embodiments, oligomeric compounds comprise conjugate groups.

As used herein "oligonucleoside" refers to an oligonucleotide in which the internucleoside linkages do not contain a phosphorus atom.

As used herein, the term "oligonucleotide" refers to an oligomeric compound comprising a plurality of linked nucleotides. In certain embodiment, one or more nucleotides of an oligonucleotide is modified. In certain embodiments, an oligonucleotide comprises ribonucleic acid (RNA) or deoxyribonucleic acid (DNA). In certain embodiments, oligonucleotides are composed of naturally- and/or non-naturally-occurring nucleobases, sugars and covalent internucleotide linkages, and may further include non-nucleic acid conjugates.

As used herein "internucleoside linkage" refers to a covalent non-phosphorus linkage between adjacent nucleosides.

As used herein "internucleotide linkage" refers to a covalent phosphorus linkage between adjacent nucleotides.

As used herein "naturally occurring internucleotide linkage" refers to a 3' to 5' phosphodiester linkage.

As used herein the term "detecting siRNA activity" or "measuring siRNA activity" means that a test for detecting or measuring siRNA activity is performed on a particular sample and compared to that of a control sample. Such detection and/or measuring can include values of zero. Thus, if a test for detection of siRNA activity results in a finding of no siRNA activity (siRNA activity of zero), the step of "detecting siRNA activity" has nevertheless been performed.

As used herein the term "control sample" refers to a sample that has not been contacted with a reporter oligomeric compound.

As used herein, the term "motif" refers to the pattern of unmodified and modified nucleotides in an oligomeric compound.

As used herein, the term "tunable REVERSIR™ compound" refers to an oligomeric compound that is complementary to and capable of hybridizing with at least one strand of a conjugated or unconjugated siRNA. Without limitations, the tunable REVERSIR™ compound could not only block unintended target PD effect but also block any potential off-target activity that could happen with a conjugated or unconjugated siRNA.

As used herein, the term "tunable REVERSIR™ activity" refers to any decrease in intensity or duration of any siRNA activity attributable to hybridization of a tunable REVERSIR™ compound to one of the strands of the siRNA.

As used herein, the term "mixed-backbone oligomeric compound" refers to an oligomeric compound wherein at least one internucleotide linkage of the oligomeric compound is different from at least one other internucleotide linkage of the oligomeric compound.

As used herein, the term "target protein" refers to a protein, the modulation of which is desired.

As used herein, the term "target gene" refers to a gene encoding a target protein.

As used herein, the term "target nucleic acid" refers to any nucleic acid molecule the expression or activity of which is capable of being modulated by a conjugated or unconjugated siRNA compound. Target nucleic acids include, but are not limited to, RNA (including, but not limited to pre-mRNA and mRNA or portions thereof) transcribed from DNA encoding a target protein, and also cDNA derived from such RNA, and miRNA. For example, the target nucleic acid can be a cellular gene (or mRNA transcribed from the gene) whose expression is associated with a particular disorder or disease state, or a nucleic acid molecule from an infectious agent.

As used herein, the term "target siRNA" refers to a siRNA compound that is targeted by a tunable REVERSIR™ compound.

As used herein, the term "targeting" or "targeted to" refers to the association of antisense strand of a siRNA to a particular target nucleic acid molecule or a particular region of nucleotides within a target nucleic acid molecule.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an oligomeric compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are oligomeric compounds (e.g., tunable REVERSIR™ compounds, siRNAs, and the like) that may comprise up to about 20% nucleotides that are mismatched (i.e., are not nucleobase complementary to the corresponding nucleotides of the target). Preferably the oligomeric compounds, such as tunable REVERSIR™ compounds and siRNAs, contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" means the pairing of complementary oligomeric compounds (e.g., an antisense strand of a siRNA and its target nucleic acid or a tunable REVERSIR™ to its target siRNA). While not limited to a particular mechanism, the most common mechanism of pairing involves hydrogen bonding, which may be Watson-Crick, Hoogsteen or reversed Hoogsteen hydrogen bonding, between complementary nucleotide or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, the antisense strand of an siRNA specifically hybridizes to more than one target site.

As used herein, "designing" or "designed to" refer to the process of designing an oligomeric compound that specifically hybridizes with a selected nucleic acid molecule.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

As used herein, "variant" refers to an alternative RNA transcript that can be produced from the same genomic region of DNA. Variants include, but are not limited to "pre-mRNA variants" which are transcripts produced from the same genomic DNA that differ from other transcripts produced from the same genomic DNA in either their start or stop position and contain both intronic and exonic sequence. Variants also include, but are not limited to, those with alternate splice junctions, or alternate initiation and termination codons.

As used herein, "high-affinity modified monomer" refers to a monomer having at least one modified nucleobase, internucleotide linkage or sugar moiety, when compared to naturally occurring monomers, such that the modification increases the affinity of an antisense compound comprising the high-affinity modified monomer to its target nucleic acid.

High-affinity modifications include, but are not limited to, monomers (e.g., nucleosides and nucleotides) comprising 2'-modified sugars.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O—$C_1$-$C_{10}$ alkyl, OCF3, O—$(CH_2)_2$—O—$CH_3$, 2'-O$(CH_2)_2$SCH$_3$, O—$(CH_2)_2$—O—N(Rm)(Rn), or O—$CH_2$—C(=O) N(Rm)(Rn), where each Rm and Rn is, independently, H or substituted or unsubstituted $C_1$-$C_{10}$ alkyl. In certain embodiments, oligomeric compounds comprise a 2' modified monomer that does not have the formula 2'-O$(CH_2)_n$H, wherein n is one to six. In certain embodiments, oligomeric compounds comprise a 2' modified monomer that does not have the formula 2'-OCH$_3$. In certain embodiments, oligomeric compounds comprise a 2' modified monomer that does not have the formula or, in the alternative, 2'-O$(CH_2)_2$OCH$_3$.

As used herein, the term "locked nucleic acid" or "LNA" or "locked nucleoside" or "locked nucleotide" refers to a nucleoside or nucleotide wherein the furanose portion of the nucleoside includes a bridge connecting two carbon atoms on the furanose ring, thereby forming a bicyclic ring system. Locked nucleic acids are also referred to as bicyclic nucleic acids (BNA).

As used herein, unless otherwise indicated, the term "methyleneoxy LNA" alone refers to β-D-methyleneoxy LNA.

As used herein, the term "MOE" refers to a 2'-O-methoxyethyl substituent.

As used herein, the term "gapmer" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) in each wing are the same. In certain embodiments, the modification(s) in one wing are different from the modification(s) in the other wing. In certain embodiments, oligomeric compounds are gapmers having 2'-deoxynucleotides in the gap and nucleotides with high-affinity modifications in the wing.

As used herein, the term "prodrug" refers to a therapeutic agent that is prepared in an inactive form that is converted to an active form (i.e., drug) within the body or cells thereof by the action of endogenous enzymes or other chemicals and/or conditions.

As used herein, the term "pharmaceutically acceptable salts" refers to salts of active compounds that retain the desired biological activity of the active compound and do not impart undesired toxicological effects thereto.

As used herein, the term "cap structure" or "terminal cap moiety" refers to chemical modifications, which have been incorporated at either terminus of an antisense compound.

As used herein, the term "prevention" refers to delaying or forestalling the onset or development of a condition or disease for a period of time from hours to days, preferably weeks to months.

As used herein, the term "amelioration" refers to a lessening of at least one activity or one indicator of the severity of a condition or disease. The severity of indicators may be determined by subjective or objective measures which are known to those skilled in the art.

As used herein, the term "treatment" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "pharmaceutical agent" refers to a substance that provides a therapeutic benefit when administered to a subject. In certain embodiments, a pharmaceutical agent is an active pharmaceutical agent. In certain embodiments, a pharmaceutical agent is a prodrug.

As used herein, the term "therapeutically effective amount" refers to an amount of a pharmaceutical agent that provides a therapeutic benefit to an animal.

As used herein, "administering" means providing a pharmaceutical agent to an animal, and includes, but is not limited to administering by a medical professional and self-administering.

As used herein, the term "co-administering" means providing more than one pharmaceutical agent to an animal. In certain embodiments, such more than one pharmaceutical agents are administered together. In certain embodiments, such more than one pharmaceutical agents are administered separately. In certain embodiments, such more than one pharmaceutical agents are administered at the same time. In certain embodiments, such more than one pharmaceutical agents are administered at different times. In certain embodiments, such more than one pharmaceutical agents are administered through the same route of administration. In certain embodiments, such more than one pharmaceutical agents are administered through different routes of administration. In certain embodiments, such more than one pharmaceutical agents are contained in the same pharmaceutical formulation. In certain embodiments, such more than one pharmaceutical agents are in separate formulations.

As used herein, the term "pharmaceutical composition" refers to a mixture of substances suitable for administering to an individual. For example, a pharmaceutical composition may comprise an antisense oligonucleotide and a sterile aqueous solution. In certain embodiments, a pharmaceutical composition includes a pharmaceutical agent and a diluent and/or carrier.

As used herein, the term "in vitro" refers to events that occur in an artificial environment, e.g., in a test tube or reaction vessel, in cell culture, etc., rather than within an organism (e.g. animal or a plant). As used herein, the term "ex vivo" refers to cells which are removed from a living organism and cultured outside the organism (e.g., in a test tube). As used herein, the term "in vivo" refers to events that occur within an organism (e.g. animal, plant, and/or microbe).

As used herein, the term "subject" or "patient" refers to any organism to which a composition disclosed herein can be administered, e.g., for experimental, diagnostic, and/or therapeutic purposes. Typical subjects include animals (e.g., mammals such as mice, rats, rabbits, non-human primates, and humans) and/or plants. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to with domesticated animals and/or pets.

In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species. In some embodiments, the subject can be of European ancestry. In some embodiments, the subject can be of African American ancestry. In some embodiments, the subject can be of Asian ancestry.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, the term "dosage unit" refers to a form in which a pharmaceutical agent is provided. In certain embodiments, a dosage unit is a vial comprising lyophilized antisense oligonucleotide. In certain embodiments, a dosage unit is a vial comprising reconstituted antisense oligonucleotide.

As used herein, the term "active pharmaceutical ingredient" refers to the substance in a pharmaceutical composition that provides a desired effect.

As used herein, the term "side effects" refers to physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

As used herein, the term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C1-C12 alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, the term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, the term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, the term "aminoalkyl" as used herein, refers to an amino substituted alkyl radical. This term is meant to include C1-C12 alkyl groups having an amino substituent at any position and wherein the alkyl group attaches the aminoalkyl group to the parent molecule. The alkyl and/or amino portions of the aminoalkyl group can be further substituted with substituent groups.

As used herein, the term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

As used herein, the term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups. As used herein, the term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups. As used herein, the terms "halo" and "halogen," as used herein, refer to an atom selected from fluorine, chlorine, bromine and iodine.

As used herein, the terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, the terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

As used herein, the term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups. As used herein, the terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

As used herein, the term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

As used herein, the term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substitutent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, the term "acyl," as used herein, refers to a radical formed by removal of a hydroxyl group from an organic acid and has the general formula C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

As used herein, the term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, the terms "substituent" and "substituent group," as used herein, include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)Raa), carboxyl (—C(O)O-Raa), aliphatic groups, alicyclic groups, alkoxy, substituted oxo (—O—Raa), aryl, aralkyl, heterocyclic, heteroaryl, heteroarylalkyl, amino (—NRbbRcc), imino (=NRbb), amido (—C(O)N-RbbRcc or —N(Rbb)C(O)Raa), azido (—N3), nitro (—NO2), cyano (—CN), carbamido (—OC(O)NRbbRcc or —N(Rbb)C(O)ORaa), ureido (—N(Rbb)C(O)NRbbRcc), thioureido (—N(Rbb)C(S)NRbbRcc), guanidinyl (—N(Rbb)C(=NRbb)NRbbRcc), amidinyl (—C(=NRbb)-NRbbRcc or —N(Rbb)C(NRbb)Raa), thiol (—SRbb), sulfinyl (—S(O)Rbb), sulfonyl (—S(O)2Rbb), sulfonamidyl (—S(O)2NRbbRcc or —N(Rbb)S(O)2Rbb) and conjugate groups. Wherein each Raa, Rbb and Rcc is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

The tunable REVERSIR™ compounds disclosed herein are particularly effective in reducing the activity of siRNAs. For example, the tunable REVERSIR™ compounds disclosed herein can reduce the activity of an siRNA by at least about 50%, or at least about 60%, or at least about 70%, or at least about 80%, or at least about 90%, or at least about 95%, or at least about 97%, or at least about 99% or up to and including a 100% decrease (i.e., absent level as compared to a reference sample), or any decrease between 50-100% as compared to a reference level. The reference level can be siRNA activity in absence of the tunable REVERSIR™ compound.

In some embodiments, the tunable REVERSIR™ compounds describe herein can reduce the activity of the siRNA by at least 75%, for example by 80%, 85%, 90%, 95% or more and upto and including completer reduction or inhibition of siRNA activity, within less than seven (e.g., within 6 days, five days, four days, three days, two days or one day) of administering or use of the tunable REVERSIR™ compound.

In some embodiments, the tunable REVERSIR™ compounds can completely reduce the siRNA activity within four days of administering or use of the tunable REVERSIR™ compound. By complete reduction of siRNA activity is meant a reduction of the siRNA activity by at least 80% relative to a reference level.

Oligomeric Compounds

In certain embodiments, the siRNA and/or the tunable REVERSIR™ compounds are oligomeric compounds. In certain embodiments, it is desirable to chemically modify oligomeric compounds, including siRNAs and/or tunable REVERSIR™ compounds, compared to naturally occurring oligomers, such as DNA or RNA. Certain such modifications alter the activity of the oligomeric compound. Certain such chemical modifications can alter activity by, for example: increasing affinity of a siRNA for its target nucleic acid or a tunable REVERSIR™ for its target siRNA, increasing its resistance to one or more nucleases, and/or altering the pharmacokinetics or tissue distribution of the oligomeric compound. In certain instances, the use of chemistries that increase the affinity of an oligomeric compound for its target can allow for the use of shorter oligomeric compounds.

Monomers

In certain embodiment, oligomeric compounds comprise one or more modified monomer. In certain such embodiments, oligomeric compounds comprise one or more high affinity monomer. In certain embodiments, such high-affinity monomer is selected from monomers (e.g., nucleosides and nucleotides) comprising 2'-modified sugars, including, but not limited to: BNA's and monomers (e.g., nucleosides and nucleotides) with 2'-substituents such as allyl, amino, azido, thio, O-allyl, O—$C_1$-$C_{10}$ alkyl, $OCF_3$, O—$(CH_2)_2$—O—$CH_3$, 2'-O$(CH_2)_2SCH_3$, O—$(CH_2)_2$—O—N(Rm)(Rn), or O—$CH_2$—C(=O) N(Rm)(Rn), where each Rm and Rn is, independently, H or substituted or unsubstituted $C_1$-$C_{10}$ alkyl.

In certain embodiments, the oligomeric compounds including, but not limited to tunable REVERSIR™ compounds and siRNAs of the present invention, comprise one or more high affinity monomers.

In certain embodiments, the oligomeric compounds including, but not limited to tunable REVERSIR™ compounds and siRNAs of the present invention, comprise one or more β-D-Methyleneoxy (4'-$CH_2$—O-2') LNA monomers.

In certain embodiments, the oligomeric compounds including, including, but not limited to tunable REVERSIR™ compounds and siRNAs of the present invention, comprise one or more α-D-Methyleneoxy (4'-$CH_2$—O-2') LNA monomers.

In certain embodiments, the oligomeric compounds including, including, but not limited to tunable REVERSIR™ compounds and siRNAs of the present invention, comprise one or more (S)-cEt monomers.

In certain embodiments, the oligomeric compounds including, but not limited to tunable REVERSIR™ compounds and siRNAs of the present invention, comprise one or more high affinity monomers provided that the oligomeric compound does not comprise a nucleotide comprising a 2'-O$(CH_2)_n$H, wherein n is one to six.

In certain embodiments, the oligomeric compounds including, but not limited to tunable REVERSIR™ compounds and siRNAs, comprise one or more high affinity monomer provided that the oligomeric compound does not comprise a nucleotide comprising a 2'-$OCH_3$ or a 2'-O$(CH_2)_2$ $OCH_3$.

In certain embodiments, the oligomeric compounds including, but not limited to tunable REVERSIR™ compounds and siRNAs, comprise one or more (e.g., 1, 2, 3, 4, 5, 6, 7, 8, 9, 10, 11, 12, 13, 14, 15 or more) high affinity monomer provided that the oligomeric compound does not comprise a α-L-Methyleneoxy (4'-$CH_2$—O-2') LNA.

In certain embodiments, the oligomeric compounds including, but no limited to tunable REVERSIR™ compounds and siRNAs, comprise one or more high affinity monomer provided that the oligomeric compound does not comprise a β-D-Methyleneoxy (4'-$CH_2$—O-2') LNA.

In certain embodiments, the oligomeric compounds including, but no limited to tunable REVERSIR™ compound and siRNAs, comprise one or more high affinity monomer provided that the oligomeric compound does not comprise a α-L-Methyleneoxy (4'-$CH_2$—O-2') LNA or β-D-Methyleneoxy (4'-$CH_2$—O-2') LNA.

Certain Nucleobases

The naturally occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleoside or internucleotide backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The unmodified or natural nucleobases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the oligomer modifications described herein. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

An oligomeric compound described herein can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Exemplary modified nucleobases include, but are not limited to, other synthetic and natural nucleobases such as inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-$N^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$, $N^6$-(dimethyl)adenine, 2-(alkyl)guanine,2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, N³-(methyl)uracil, 5-uracil (i.e., pseudouracil), 2-(thio)pseudouracil,4-(thio)pseudouracil,2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, N²-substituted purines, N⁶-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and "universal bases" can be employed.

As used herein, a universal nucleobase is any nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, Nucleic Acids Research, 29, 2437-2447).

Further nucleobases include those disclosed in U.S. Pat. No. 3,687,808; those disclosed in International Application No. PCT/US09/038425, filed Mar. 26, 2009; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

In some embodiments, the tunable REVERSIR™ compound comprises at least one (e.g., 1, 2, 3, 4, 5, 6, 7, 8, 9, or 10) G-clamp nucleobase selected from the following:

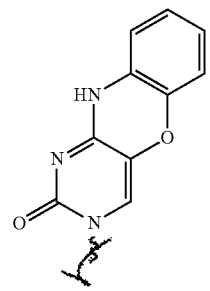

A-001

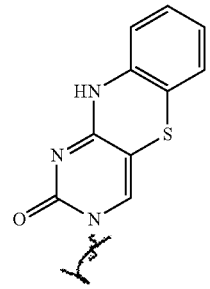

A-002

-continued
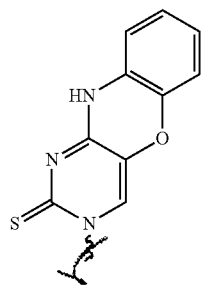
A-001
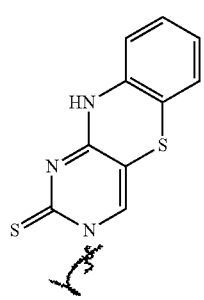
A-003
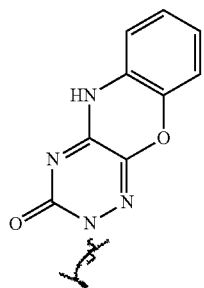
A-004
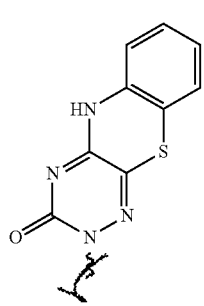
A-005
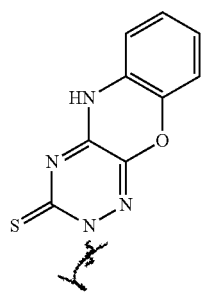
A-006
-continued
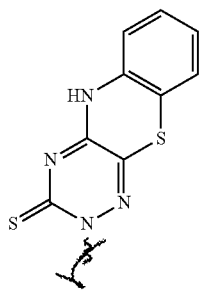
A-007
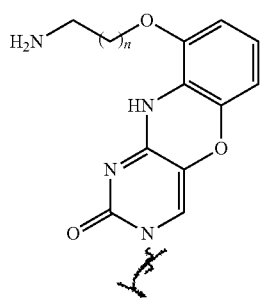
A-008
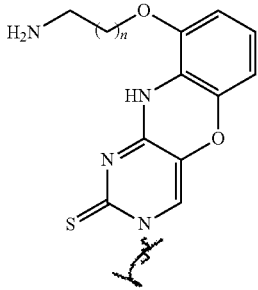
A-009
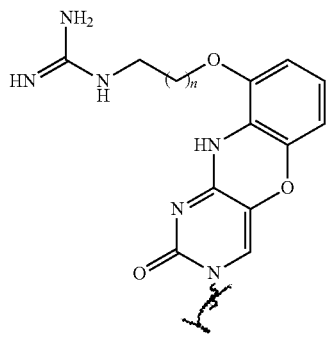
A-010
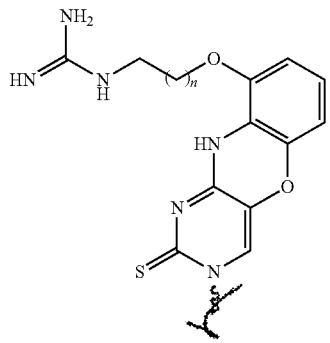
A-011

-continued
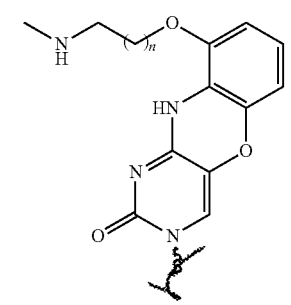
A-012
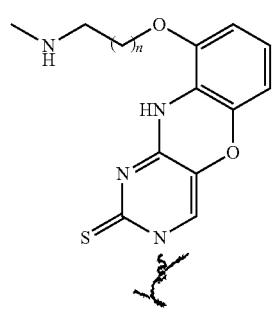
A-013
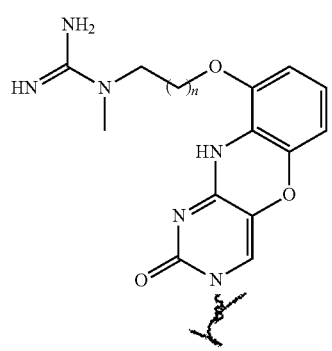
A-014
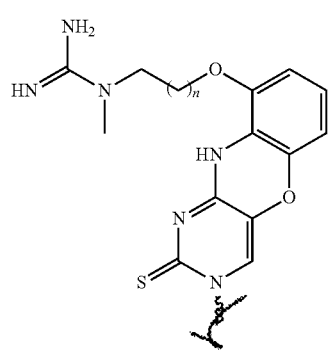
A-015
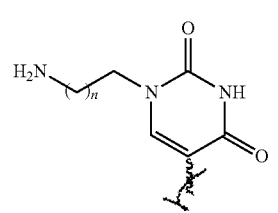
A-016
-continued
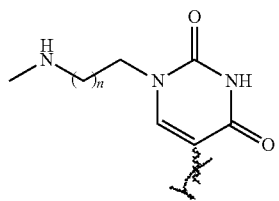
A-017
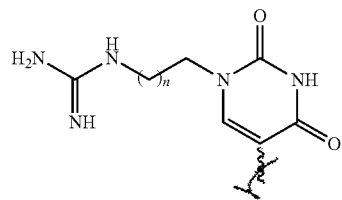
A-018
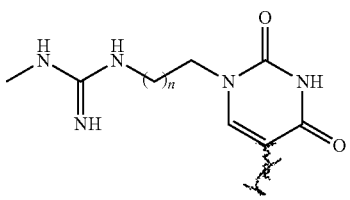
A-019
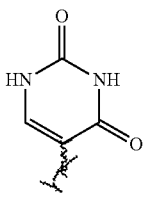
A-020
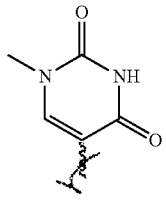
A-021
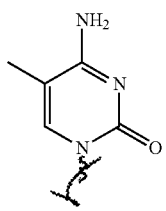
A-022
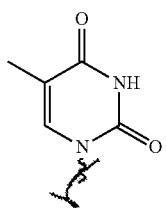
A-024

-continued

A-025

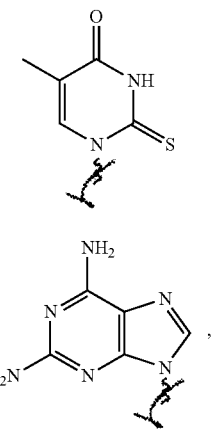

A-026 where n is 0, 1, 2, 3, 4, 5 or 6.

Certain Sugars

Oligomeric compounds provided herein can comprise one or more monomer, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a locked nucleic acid or bicyclic nucleic acid. In certain embodiments, oligomeric compounds comprise one or more monomers that are LNA.

In some embodiments of a locked nucleic acid, the 2' position of furnaosyl is connected to the 4' position by a linker selected independently from —[C(R1)(R2)]$_n$—, —[C(R1)(R2)]$_n$—O—, —[C(R1)(R2)]$_n$—N(R1)—, —[C(R1)(R2)]$_n$—N(R1)-O—, —[C(R1R2)]n-O—N(R1)—, —C(R1)=C(R2)-O—, —C(R1)=N—, —C(R1)=N—O—, —C(=NR1)—, —C(=NR1)-O—, C(=O)—, —C(=O)O—, —C(=S)—, —C(=S)O—, —C(=S)S—, —O—, —Si(R1)2-, —S(=O)$_x$— and —N(R1)-;

wherein:

x is 0, 1, or 2;

n is 1, 2, 3, or 4;

each R1 and R2 is, independently, H, a protecting group, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, heterocycle radical, substituted heterocycle radical, heteroaryl, substituted heteroaryl, C5-C7 alicyclic radical, substituted C5-C7 alicyclic radical, halogen, OJ1, NJ1J2, SJ1, N3, COOJ1, acyl (C(=O)—H), substituted acyl, CN, sulfonyl (S(=O) 2J1), or sulfoxyl (S(=O)-J1); and each J1 and J2 is, independently, H, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, acyl (C(=O)—H), substituted acyl, a heterocycle radical, a substituted heterocycle radical, C1-C12 aminoalkyl, substituted C1-C12 aminoalkyl or a protecting group.

In one embodiment, each of the linkers of the LNA compounds is, independently, —[C(R1)(R2)]n-, —[C(R1)(R2)]n-O—, —C(R1R2)-N(R1)-O— or —C(R1R2)-O—N(R1)—. In another embodiment, each of said linkers is, independently, 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R1)-2' and 4'-CH$_2$—N(R1)—O-2'- wherein each R1 is, independently, H, a protecting group or C1-C12 alkyl.

Certain LNA's have been prepared and disclosed in the patent literature as well as in scientific literature (Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039; Examples of issued US patents and published applications that disclose LNA s include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

Also provided herein are LNAs in which the 2'-hydroxyl group of the ribosyl sugar ring is linked to the 4' carbon atom of the sugar ring thereby forming a methyleneoxy (4'-CH$_2$—O-2') linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH$_2$—) group bridging the 2' oxygen atom and the 4' carbon atom, for which the term methyleneoxy (4'-CH$_2$—O-2') LNA is used for the bicyclic moiety; in the case of an ethylene group in this position, the term ethyleneoxy (4'-CH$_2$CH$_2$—O-2') LNA is used (Singh et al., Chem. Commun., 1998, 4, 455-456: Morita et al., Bioorganic Medicinal Chemistry, 2003, 11, 2211-2226). Methyleneoxy (4'-CH$_2$—O-2') LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., Proc. Natl. Acad. Sci. U.S.A., 2000, 97, 5633-5638).

An isomer of methyleneoxy (4'-CH$_2$—O-2') LNA that has also been discussed is alpha-L-methyleneoxy (4'-CH$_2$—O-2') LNA which has been shown to have superior stability against a 3'-exonuclease. The alpha-L-methyleneoxy (4'-CH$_2$—O-2') LNA's were incorporated into antisense gapmers and chimeras that showed potent antisense activity (Frieden et al., Nucleic Acids Research, 2003, 21, 6365-6372).

The synthesis and preparation of the methyleneoxy (4'-CH$_2$—O-2') LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). BNAs and preparation thereof are also described in WO 98/39352 and WO 99/14226.

Analogs of methyleneoxy (4'-CH$_2$—O-2') LNA, phosphorothioate-methyleneoxy (4'-CH$_2$—O-2') LNA and 2'-thio-LNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-LNA, a novel comformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Modified sugar moieties are well known and can be used to alter, typically increase, the affinity of the antisense compound for its target and/or increase nuclease resistance. A representative list of preferred modified sugars includes but is not limited to bicyclic modified sugars, including methyleneoxy (4'-CH$_2$—O-2') LNA and ethyleneoxy (4'-(CH$_2$)$_2$—O-2' bridge) ENA; substituted sugars, especially 2'-substituted sugars having a 2'-F, 2'-OCH$_3$ or a 2'-O(CH$_2$)$_2$—OCH$_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR, n=1-50; "locked" nucleic acids (LNA) in which the furanose portion of the nucleoside includes a bridge connecting two carbon atoms on the furanose ring, thereby forming a bicyclic ring system; O-AMINE or O—(CH$_2$)$_n$AMINE (n=1-10, AMINE=NH$_2$; alkylamino, dialkylamino, heterocyclyl, arylamino, diaryl amino, heteroaryl amino, diheteroaryl amino, ethylene diamine or polyamino); and O—CH$_2$CH$_2$(NCH$_2$CH$_2$NMe$_2$)$_2$.

"Deoxy" modifications include hydrogen (i.e. deoxyribose sugars, which are of particular relevance to the single-strand overhangs); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar);

cyano; mercapto; alkyl-thio-alkyl; thioalkoxy; thioalkyl; alkyl; cycloalkyl; aryl; alkenyl and alkynyl, which can be optionally substituted with e.g., an amino functionality.

Other suitable 2'-modifications, e.g., modified MOE, are described in U.S. Patent Application Publication No. 20130130378, contents of which are herein incorporated by reference.

A modification at the 2' position can be present in the arabinose configuration The term "arabinose configuration" refers to the placement of a substituent on the C2' of ribose in the same configuration as the 2'-OH is in the arabinose.

The sugar can comprise two different modifications at the same carbon in the sugar, e.g., gem modification. The sugar group can also contain one or more carbons that possess the opposite stereochemical configuration than that of the corresponding carbon in ribose. Thus, an oligomeric compound can include one or more monomers containing e.g., arabinose, as the sugar. The monomer can have an alpha linkage at the 1' position on the sugar, e.g., alpha-nucleosides. The monomer can also have the opposite configuration at the 4'-position, e.g., C5' and H4' or substituents replacing them are interchanged with each other. When the C5' and H4' or substituents replacing them are interchanged with each other, the sugar is said to be modified at the 4' position.

Oligomeric compounds can also include abasic sugars, i.e., a sugar which lack a nucleobase at C-1' or has other chemical groups in place of a nucleobase at C1'. See for example U.S. Pat. No. 5,998,203, content of which is herein incorporated in its entirety. These abasic sugars can also be further containing modifications at one or more of the constituent sugar atoms. Oligomeric compounds can also contain one or more sugars that are the L isomer, e.g. L-nucleosides. Modification to the sugar group can also include replacement of the 4'-O with a sulfur, optionally substituted nitrogen or CH$_2$ group. In some embodiments, linkage between C1' and nucleobase is in α configuration.

Sugar modifications can also include acyclic nucleotides, wherein a C—C bonds between ribose carbons (e.g., C1'-C2', C2'-C3', C3'-C4', C4'-O4', C1'-O4') is absent and/or at least one of ribose carbons or oxygen (e.g., C1', C2', C3', C4' or O4') are independently or in combination absent from the nucleotide. In some embodiments, acyclic nucleotide is

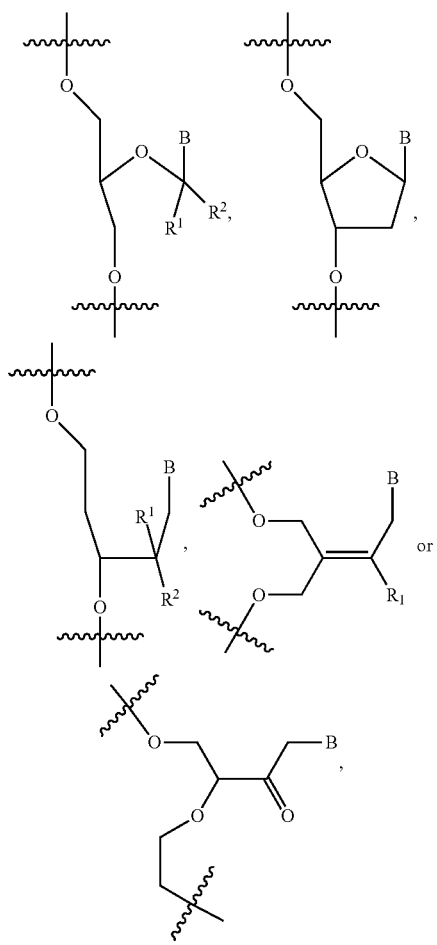

wherein B is a modified or unmodified nucleobase, R$_1$ and R$_2$ independently are H, halogen, OR, or alkyl;

and R3 is H, alkyl, cycloalkyl, aryl, aralkyl, heteroaryl or sugar).

In some embodiments, sugar modifications are selected from the group consisting of 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH$_2$CH$_2$-(4'-C) (ENA), 2'-O-aminopropyl (2'-O-AP), 2'-O-dimethylaminoethyl (2'-O-

DMAOE), 2'-O-dimethylaminopropyl (2'-O-DMAP), 2'-O-dimethylaminoethyloxyethyl (2'-O-DMAEOE) and gem 2'-OMe/2'F with 2'-O-Me in the arabinose configuration.

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position. A modification at the 3' position can be present in the xylose configuration The term "xylose configuration" refers to the placement of a substituent on the C3' of ribose in the same configuration as the 3'-OH is in the xylose sugar.

The hydrogen attached to C4' and/or C1' can be replaced by a straight- or branched-optionally substituted alkyl, optionally substituted alkenyl, optionally substituted alkynyl, wherein backbone of the alkyl, alkenyl and alkynyl can contain one or more of O, S, S(O), $SO_2$, N(R'), C(O), N(R')C(O)O, OC(O)N(R'), CH(Z'), phosphorous containing linkage, optionally substituted aryl, optionally substituted heteroaryl, optionally substituted heterocyclic or optionally substituted cycloalkyl, where R' is hydrogen, acyl or optionally substituted aliphatic, Z' is selected from the group consisting of $OR_{11}$, $COR_{11}$, $CO_2R_{11}$,

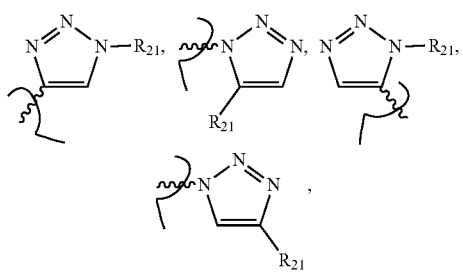

$NR_{21}R_{31}$, $CONR_{21}R_{31}$, $CON(H)NR_{21}R_{31}$, $ORN_{21}R_{31}$, $CON(H)N=CR_{41}R_{51}$, $N(R_{21})C(=NR_{31})NR_{21}R_{31}$, $N(R_{21})C(O)NR_{21}R_{31}$, $N(R_{21})C(S)NR_{21}R_{31}$, $OC(O)NR_{21}R_{31}$, $SC(O)NR_{21}R_{31}$, $N(R_{21})C(S)OR_{11}$, $N(R_{21})C(O)OR_{11}$, $N(R_{21})C(O)SR_{11}$, $N(R_{21})N=CR_{41}R_{51}$, $ON=CR_{41}R_{51}$, $SO_2R_{11}$, $SOR_{11}$, $SR_{11}$, and substituted or unsubstituted heterocyclic; R21 and R31 for each occurrence are independently hydrogen, acyl, unsubstituted or substituted aliphatic, aryl, heteroaryl, heterocyclic, $OR_{11}$, $COR_{11}$, $CO_2R_{11}$, or $NR_{11}R_{11}'$; or $R_{21}$ and $R_{31}$, taken together with the atoms to which they are attached, form a heterocyclic ring; $R_{41}$ and $R_{51}$ for each occurrence are independently hydrogen, acyl, unsubstituted or substituted aliphatic, aryl, heteroaryl, heterocyclic, $O_{11}$, $COR_{11}$, or $CO_2R_{11}$, or $NR_{11}R_{11}'$; and $R_{11}$ and $R_{11}'$ are independently hydrogen, aliphatic, substituted aliphatic, aryl, heteroaryl, or heterocyclic. In some embodiments, the hydrogen attached to the C4' of the 5' terminal nucleotide is replaced.

In some embodiments, C4' and C5' together form an optionally substituted heterocyclic, preferably comprising at least one —PX(Y)—, wherein X is H, OH, OM, SH, optionally substituted alkyl, optionally substituted alkoxy, optionally substituted alkylthio, optionally substituted alkylamino or optionally substituted dialkylamino, where M is independently for each occurrence an alki metal or transition metal with an overall charge of +1; and Y is O, S, or NR', where R' is hydrogen, optionally substituted aliphatic. Preferably this modification is at the 5 terminal of the oligonucleotide.

In certain embodiments, LNA's include bicyclic nucleotide having the formula:

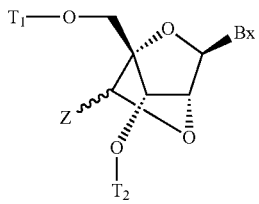

wherein:
Bx is a heterocyclic base moiety;
T1 is H or a hydroxyl protecting group;
T2 is H, a hydroxyl protecting group or a reactive phosphorus group;
Z is C1-C6 alkyl, C2-C6 alkenyl, C2-C6 alkynyl, substituted C1-C6 alkyl, substituted
C2-C6 alkenyl, substituted C2-C6 alkynyl, acyl, substituted acyl, or substituted amide.

In one embodiment, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In certain such embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H, C1-C6 alkyl, or substituted C1-C6 alkyl and X is O or NJ1.

In certain embodiments, the Z group is C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is C1-C6 alkyl substituted with one or more Xx, wherein each Xx is independently halo (e.g., fluoro), hydroxyl, alkoxy (e.g., $CH_3O$—), substituted alkoxy or azido.

In certain embodiments, the Z group is —$CH_2$Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is —$CH_2$Xx, wherein Xx is halo (e.g., fluoro), hydroxyl, alkoxy (e.g., $CH_3O$—) or azido.

In certain such embodiments, the Z group is in the (R)-configuration:

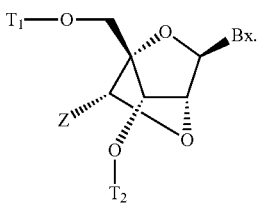

In certain such embodiments, the Z group is in the (S)-configuration:

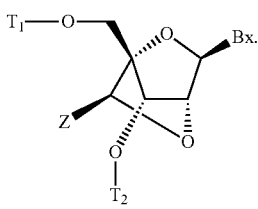

In certain embodiments, each T1 and T2 is a hydroxyl protecting group. A preferred list of hydroxyl protecting groups includes benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, T1 is a hydroxyl protecting group selected from acetyl, benzyl, t-butyldimethylsilyl, t-butyldiphenylsilyl and dimethoxytrityl wherein a more preferred hydroxyl protecting group is T1 is 4,4'-dimethoxytrityl.

In certain embodiments, T2 is a reactive phosphorus group wherein preferred reactive phosphorus groups include diisopropylcyanoethoxy phosphoramidite and H-phosphonate. In certain embodiments T1 is 4,4'-dimethoxytrityl and T2 is diisopropylcyanoethoxy phosphoramidite.

In certain embodiments, oligomeric compounds have at least one monomer of the formula:

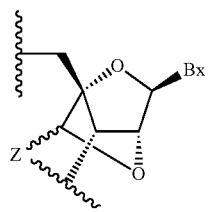

or of the formula:

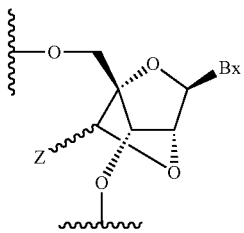

or of the formula:

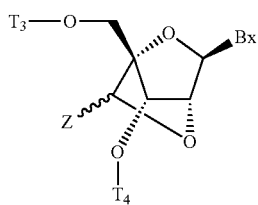

wherein
Bx is a heterocyclic base moiety;
T3 is H, a hydroxyl protecting group, a linked conjugate group or an internucleoside linking group attached to a nucleoside, a nucleotide, an oligonucleoside, an oligonucleotide, a monomeric subunit or an oligomeric compound;
T4 is H, a hydroxyl protecting group, a linked conjugate group or an internucleoside linking group attached to a nucleoside, a nucleotide, an oligonucleoside, an oligonucleotide, a monomeric subunit or an oligomeric compound;
wherein at least one of T3 and T4 is an internucleoside linking group attached to a nucleoside, a nucleotide, an oligonucleoside, an oligonucleotide, a monomeric subunit or an oligomeric compound; and
Z is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, or substituted amide.

In one embodiment, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In one embodiment, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H or C1-C6 alkyl, and X is O or NJ1.

In certain such embodiments, at least one Z is C1-C6 alkyl or substituted C1-C6 alkyl. In certain embodiments, each Z is, independently, C1-C6 alkyl or substituted C1-C6 alkyl. In certain embodiments, at least one Z is C1-C6 alkyl. In certain embodiments, each Z is, independently, C1-C6 alkyl. In certain embodiments, at least one Z is methyl. In certain embodiments, each Z is methyl. In certain embodiments, at least one Z is ethyl. In certain embodiments, each Z is ethyl. In certain embodiments, at least one Z is substituted C1-C6 alkyl. In certain embodiments, each Z is, independently, substituted C1-C6 alkyl. In certain embodiments, at least one Z is substituted methyl. In certain embodiments, each Z is substituted methyl. In certain embodiments, at least one Z is substituted ethyl. In certain embodiments, each Z is substituted ethyl.

In certain embodiments, at least one substituent group is C1-C6 alkoxy (e.g., at least one Z is C1-C6 alkyl substituted with one or more C1-C6 alkoxy). In another embodiment, each substituent group is, independently, C1-C6 alkoxy (e.g., each Z is, independently, C1-C6 alkyl substituted with one or more C1-C6 alkoxy).

In certain embodiments, at least one C1-C6 alkoxy substituent group is CH3O— (e.g., at least one Z is CH3OCH2—). In another embodiment, each C1-C6 alkoxy substituent group is CH3O— (e.g., each Z is CH3OCH2—).

In certain embodiments, at least one substituent group is halogen (e.g., at least one Z is C1-C6 alkyl substituted with one or more halogen). In certain embodiments, each substituent group is, independently, halogen (e.g., each Z is, independently, C1-C6 alkyl substituted with one or more halogen). In certain embodiments, at least one halogen substituent group is fluoro (e.g., at least one Z is CH2FCH2—, CHF2CH2— or CF3CH2—). In certain embodiments, each halo substituent group is fluoro (e.g., each Z is, independently, CH2FCH2—, CHF2CH2— or CF3CH2—).

In certain embodiments, at least one substituent group is hydroxyl (e.g., at least one Z is C1-C6 alkyl substituted with one or more hydroxyl). In certain embodiments, each substituent group is, independently, hydroxyl (e.g., each Z is, independently, C1-C6 alkyl substituted with one or more hydroxyl). In certain embodiments, at least one Z is $HOCH_2$—. In another embodiment, each Z is $HOCH_2$—.

In certain embodiments, at least one Z is $CH_3$—, $CH_3CH_2$—, $CH_2OCH_3$—, $CH_2F$— or $HOCH_2$—. In certain embodiments, each Z is, independently, $CH_3$—, $CH_3CH_2$—, $CH_2OCH_3$—, $CH_2F$— or $HOCH_2$—.

In certain embodiments, at least one Z group is C1-C6 alkyl substituted with one or more Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, at least one Z group is C1-C6 alkyl substituted with one or more Xx, wherein each Xx is, independently, halo (e.g., fluoro), hydroxyl, alkoxy (e.g., $CH_3O$—) or azido.

In certain embodiments, each Z group is, independently, C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, C1-C6 alkyl substituted with one or more Xx, wherein each Xx is independently halo (e.g., fluoro), hydroxyl, alkoxy (e.g., $CH_3O$—) or azido.

In certain embodiments, at least one Z group is —$CH_2Xx$, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1 In certain embodiments, at least one Z group is —$CH_2Xx$, wherein Xx is halo (e.g., fluoro), hydroxyl, alkoxy (e.g., $CH_3O$—) or azido.

In certain embodiments, each Z group is, independently, —$CH_2Xx$, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, —$CH_2Xx$, wherein each Xx is, independently, halo (e.g., fluoro), hydroxyl, alkoxy (e.g., $CH_3O$—) or azido.

In certain embodiments, at least one Z is $CH_3$—. In another embodiment, each Z is, $CH_3$—.

In certain embodiments, the Z group of at least one monomer is in the (R)-configuration represented by the formula:

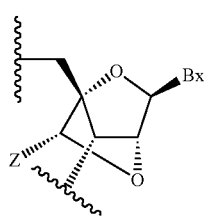

or the formula:

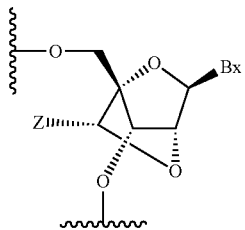

or the formula:

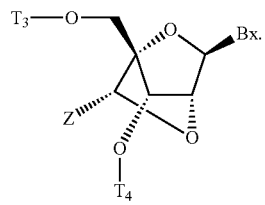

In certain embodiments, the Z group of each monomer of the formula is in the (R)— configuration.

In certain embodiments, the Z group of at least one monomer is in the (S)— configuration represented by the formula:

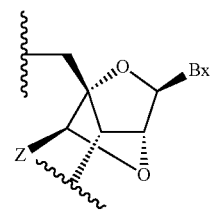

or the formula:

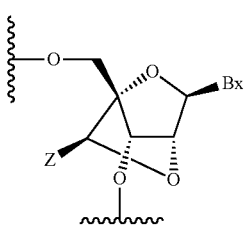

or the formula:

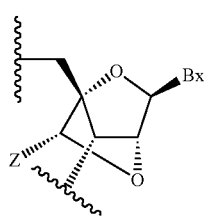

or the formula:

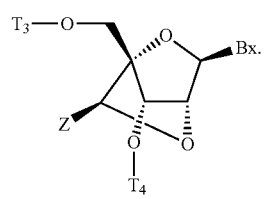

In certain embodiments, the Z group of each monomer of the formula is in the (S)— configuration.

In certain embodiments, T3 is H or a hydroxyl protecting group. In certain embodiments, T4 is H or a hydroxyl protecting group. In a further embodiment T3 is an internucleoside linking group attached to a nucleoside, a nucleotide or a monomeric subunit. In certain embodiments, T4 is an internucleoside linking group attached to a nucleoside, a nucleotide or a monomeric subunit. In certain embodiments, T3 is an internucleoside linking group attached to an oligonucleoside or an oligonucleotide. In certain embodiments, T4 is an internucleoside linking group attached to an oligonucleoside or an oligonucleotide. In certain embodiments, T3 is an internucleoside linking group attached to an oligomeric compound. In certain embodiments, T4 is an internucleoside linking group attached to an oligomeric compound. In certain embodiments, at least one of T3 and T4 comprises an internucleotide linking group selected from phosphodiester or phosphorothioate.

In certain embodiments, oligomeric compounds have at least one region of at least two contiguous monomers of the formula:

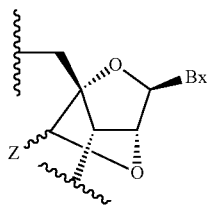

or of the formula:

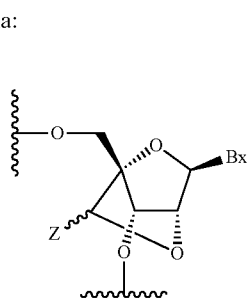

or of the formula:

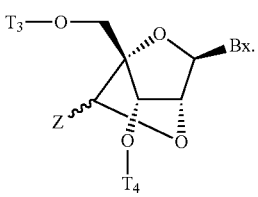

In certain such embodiments, LNAs include, but are not limited to, (A) α-L-Methyleneoxy (4'-CH$_2$—O-2') LNA, (B) β-D-Methyleneoxy (4'-CH2-O-2') LNA, (C) Ethyleneoxy (4'-(CH2)2-O-2') LNA, (D) Aminooxy (4'-CH2-O—N(R)-2') LNA and (E) Oxyamino (4'-CH2-N(R)—O-2') LNA, as depicted below:

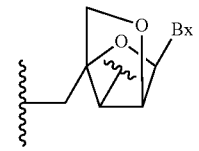
(A)

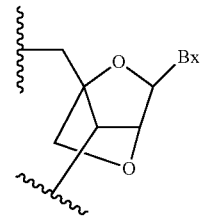
(B)

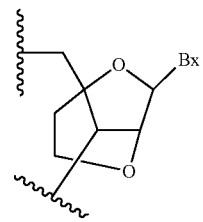
(C)

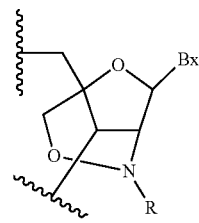
(D)

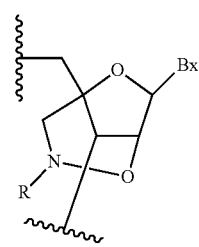
(E)

In certain embodiments, the oligomeric compound comprises at least two regions of at least two contiguous monomers of the above formula. In certain embodiments, the oligomeric compound comprises a gapped oligomeric compound. In certain embodiments, the oligomeric compound comprises at least one region of from about 8 to about 14 contiguous (3-D-2'-deoxyribofuranosyl nucleosides. In certain embodiments, the oligomeric compound comprises at least one region of from about 9 to about 12 contiguous (3-D-2'-deoxyribofuranosyl nucleosides.

In certain embodiments, the oligomeric compound comprises at least one (e.g., 1, 2, 3, 4, 5, 6, 7, 8, 9, 10, 11, 12, 13, 14, 15 or more) S-cEt monomer of the formula:

S-cEt (C)
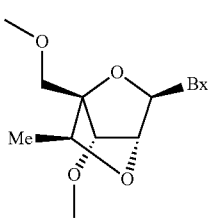
wherein Bx IS heterocyclic base moiety.
In some embodiments, the oligomeric compound, e.g. tunable REVERSIR™ compound, comprises at least one (e.g., 1, 2, 3, 4, 5, 6, 7, 8, 9, 10, 11, 12, 13, 14, 15 or more) nucleotide selected from the following:
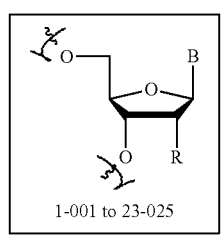
1-001 to 23-025
A-001
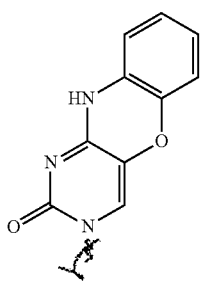
A-002
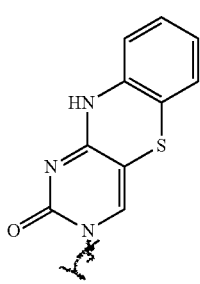
A-001
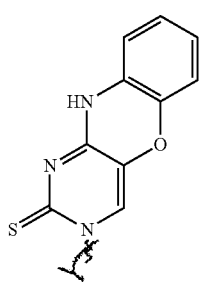
A-003
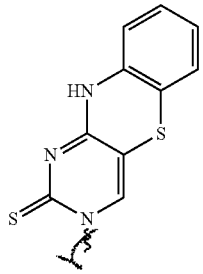
A-004
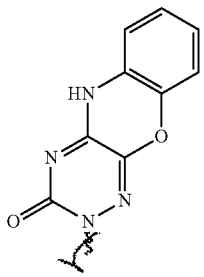
A-005
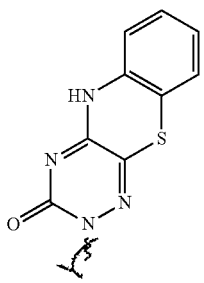
A-006
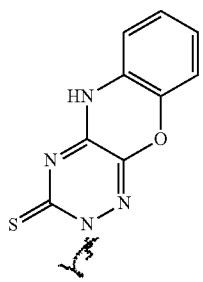
A-007
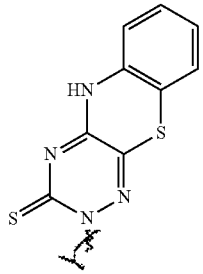

A-008
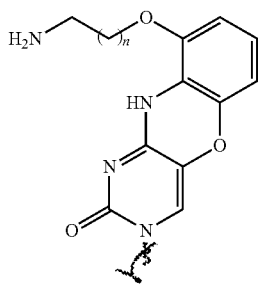
A-009
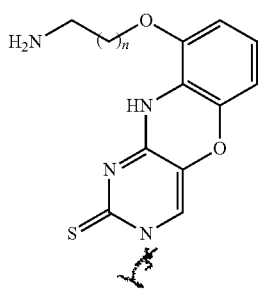
A-010
A-011
A-012
A-013
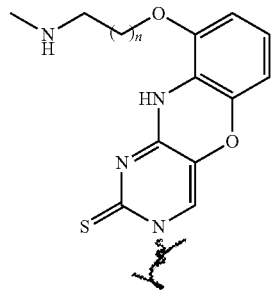
A-014
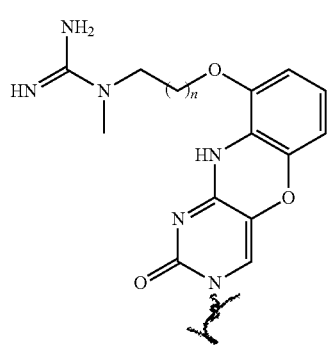
A-015
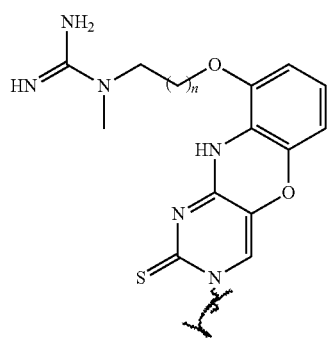
A-016
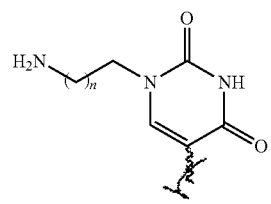
A-017
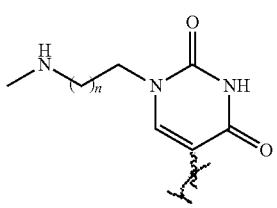
A-018
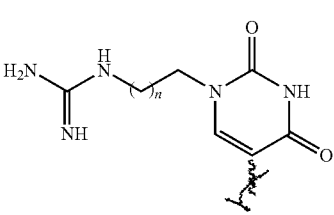

A-019 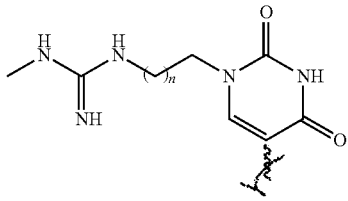

A-020 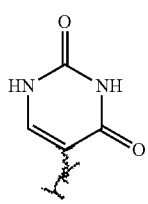

A-021 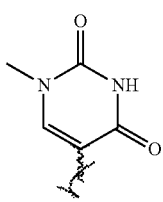

A-022 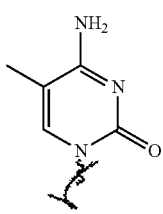

A-024 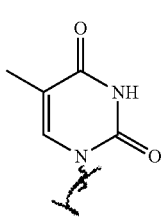

A-025 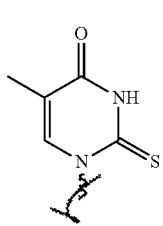

A-026 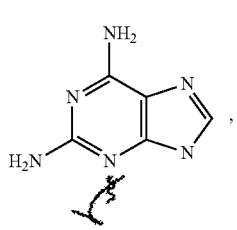

1-001 to 1-025 R = OH
2-001 to 2-025 R = F
3-001 to 3-025 R = OMe
4-001 to 4-025 R = O(CH$_2$)$_2$OMe
5-001 to 5-025 R = O(CH$_2$)$_2$SMe
6-001 to 6-025 R = O(CH$_2$)$_2$OBn
7-001 to 7-025 R = OCH$_2$CF$_3$
8-001 to 8-025 R = O(CH$_2$)$_2$OCF$_3$
9-001 to 9-025 R = O(CH$_2$)C(O)NH(Me)
10-001 to 10-025 R = O(CH$_2$)$_2$ONMe$_2$
11-001 to 11-025 R = O(CH$_2$)$_2$ON=CH$_2$
12-001 to 12-025 R = O(CH$_2$)CH=CH$_2$
13-001 to 13-025 R = O(CH$_2$)C≡CH
14-001 to 14-025 R = CH$_2$CF$_3$
15-001 to 15-025 R = CH$_2$CH$_2$F
16-001 to 16-025 R = CF$_3$
17-001 to 17-025 R = araF
18-001 to 18-025 R = O(CH$_2$)$_2$O(CH$_2$)$_2$NMe$_2$ 19-001 to 19-025 R = 

20-001 to 20-025 R = 

21-001 to 21-025 R = 

22-001 to 22-025 R = 

23-001 to 23-025 R = where B is A-001 to A-026 and n is 0-6 (e.g., 0, 1, 2, 3, 4, 5 or 6).

In certain embodiments, monomers include sugar mimetics. In certain such embodiments, a mimetic is used in place of the sugar or sugar-internucleoside linkage combination, and the nucleobase is maintained for hybridization to a selected target. Representative examples of a sugar mimetics include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances, a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside, nucleotide and nucleobase mimetics are well known to those skilled in the art.

In certain embodiments, the tunable REVERSIR™ compound comprises at least one monomer that is LNA and at least one G-clamp nucleobase. For example, the tunable REVERSIR™ compound can comprise 1, 2, 3, 4, 5, 6, 7, 8, 9, 10, 11, 12, 13, 14, 15 or more monomers that are LNA 1, 2, 3, 4, 5, 6, 7, 8, 9, 10, 11, 12, 13, 14, 15 or more G-clamp nucleobases.

In some embodiments, the tunable REVERSIR™ compound comprises at least one (e.g., 1, 2, 3, 4, 5, 6, 7, 8, 9, 10, 11, 12, 13, 14, 15 or more) peptide nucleic acid monomer. In certain embodiments, the tunable REVERSIR™ compound comprises at least one monomer that is LNA and at least one monomer that is PNA. For example, the tunable REVERSIR™ compound can comprise 1, 2, 3, 4, 5, 6, 7, 8, 9, 10, 11, 12, 13, 14, 15 or more monomers that are LNA 1, 2, 3, 4, 5, 6, 7, 8, 9, 10, 11, 12, 13, 14, 15 or more monomers that are PNA.

In certain embodiments, the tunable REVERSIR™ compound comprises at least one PNA monomer and at least one G-clamp nucleobase. For example, the tunable REVERSIR™ compound can comprise 1, 2, 3, 4, 5, 6, 7, 8, 9, 10, 11, 12, 13, 14, 15 or more PNA monomers and 1, 2, 3, 4, 5, 6, 7, 8, 9, 10, 11, 12, 13, 14, 15 or more G-clamp nucleobases.

In certain embodiments, the tunable REVERSIR™ compound comprises at least one LNA monomer, at least one PNA monomer and at least one G-clamp nucleobase. For example, the tunable REVERSIR™ compound can comprise 1, 2, 3, 4, 5, 6, 7, 8, 9, 10, 11, 12, 13, 14, 15 or more LNA monomers; 1, 2, 3, 4, 5, 6, 7, 8, 9, 10, 11, 12, 13, 14, 15 or more PNA monomers and 1, 2, 3, 4, 5, 6, 7, 8, 9, 10, 11, 12, 13, 14, 15 or more G-clamp nucleobases.

Monomeric Linkages

Described herein are linking groups that link monomers (including, but not limited to, modified and unmodified nucleosides and nucleotides) together, thereby forming an oligomeric compound. Such linking groups are also referred to as intersugar linkage. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The phosphate group in the linking group can be modified by replacing one of the oxygens with a different substituent. One result of this modification can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the linkage can be replaced by any of the following: S, Se, BR$_3$ (R is hydrogen, alkyl, aryl), C (i.e. an alkyl group, an aryl group, etc. . . . ), H, NR$_2$ (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the sugar of the monomer), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker."

In certain embodiments, the phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-CH$_2$—C(=O)—N(H)-5') and amide-4 (3'-CH$_2$—N(H)—C(=O)-5')), hydroxylamino, siloxane (dialkylsiloxane), carboxamide, carbonate, carboxymethyl, carbamate, carboxylate ester, thioether, ethylene oxide linker, sulfide, sulfonate, sulfonamide, sulfonate ester, thioformacetal (3'-S—CH$_2$—O-5'), formacetal (3'-O—CH$_2$—O-5'), oxime, methyleneimino, methykenecarbonylamino, methylenemethylimino (MMI, 3'-CH$_2$—N(CH$_3$)—O-5'), methylenehydrazo, methylenedimethylhydrazo, methyleneoxymethylimino, ethers (C3'-O—C5'), thioethers (C3'-S—C5'), thioacetamido (C3'-N(H)—C(=O)—CH$_2$—S—C5', C3'-O—P(O)—O—SS—C5', C3'-CH$_2$—NH—NH—C5', 3'-NHP(O)(OCH$_3$)-0-5' and 3'-NHP(O)(OCH$_3$)—O-5' and nonionic linkages containing mixed N, O, S and CH$_2$ component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phsophotriesters, aminoalkylphosphotrioesters, alkyl-phosphonaters (e.g., methylphosphonate), selenophosphates, phosphoramidates (e.g., N-alkylphosphoramidate), and boranophosphonates.

In some embodiments, the oligomeric compound, e.g., tunable REVERSIR™ compound or siRNA, comprises at least one (e.g., 1, 2, 3, 4, 5, 6, 7, 8, 9, 10, 11, 12, 13, 14, 15 or more and upto including all) modified or nonphosphodiester linkages. In one embodiment, the oligomeric compound, e.g., tunable REVERSIR™ compound or siRNA, comprises at least one (e.g., 1, 2, 3, 4, 5, 6, 7, 8, 9, 10, 11, 12, 13, 14, 15 or more and upto including all) phosphorothioate linkages.

In some embodiments, all internucleotide linkages in the reverser compounds are phosphorothioate (PS) internucleotide linkages. In certain embodiments, the tunable REVERSIR™ compounds comprise at least one phosphorothioate (PS) internucleotide linkage, but not all internucleotide linkages in said tunable REVERSIR™ compound are a phosphorothioate linkage. In other words, in some embodiments, less than 100% (e.g., 95%, 90%, 85%, 80%, 75%, 70%, 65%, 60%, 55%, 50%, 45%, 40% or fewer) of the internucleotide linkages are phosphorothioate linkages.

In some embodiments, the tunable REVERSIR™ compounds comprise at least one phosphorothioate internucleotide linkage and at least one internucleoside or internucleotide linkage that is not a phosphorothioate. For example, the tunable REVERSIR™ compounds comprise at least one phosphorothioate internucleotide linkage and at least one phosphodiester internucleotide linkage. In some embodiments, the non-phosphorothioate internucleotide linkage is between the terminus and the penultimate nucleotides.

In some embodiments, the internucleotide linkage between the nucleobase at the 3'-terminus of the tunable REVERSIR™ compound and the rest of the tunable REVERSIR™ compound is a phosphodiester linkage. In some embodiments, all internucleotide linkages in the reverser compounds are phosphorothioate except for the internucleotide linkage between the nucleotide at the 3'-terminus of the tunable REVERSIR™ compound and the rest of the tunable REVERSIR™ compound.

Oligomeric compounds can also be constructed wherein the phosphate linker and the sugar are replaced by nuclease resistant nucleoside, nucleotide or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backnone-extended pyrrolidine PNA (bepPNA) nucleoside surrogates. A preferred surrogate is a PNA surrogate.

The oligomeric compounds described herein contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the antisense compounds provided herein are all such possible isomers, as well as their racemic and optically pure forms.

Terminal Modifications

Ends of the oligomeric compound can be modified. Such modifications can be at one end or both ends. For example, the 3' and/or 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a double stranded oligomeric compound, this array can substitute for a hairpin loop in a hairpin-type oligomeric compound.

Terminal modifications useful for modulating activity include modification of the 5' end of oligomeric compound with phosphate or phosphate analogs. In certain embodiments, the 5'end of oligomeric compound is phosphorylated or includes a phosphoryl analog. Exemplary 5'-phosphate modifications include those which are compatible with RISC mediated gene silencing. Modifications at the 5'-terminal end can also be useful in stimulating or inhibiting the immune system of a subject. In some embodiments, the 5'-end of the oligomeric compound comprises the modification

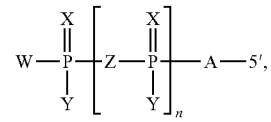

wherein W, X and Y are each independently selected from the group consisting of O, OR (R is hydrogen, alkyl, aryl), S, Se, BR$_3$ (R is hydrogen, alkyl, aryl), BH$_3^-$, C (i.e. an alkyl group, an aryl group, etc. . . . ), H, NR$_2$ (R is hydrogen, alkyl, aryl), or OR (R is hydrogen, alkyl or aryl); A and Z are each independently for each occurrence absent, O, S, CH$_2$, NR (R is hydrogen, alkyl, aryl), or optionally substituted alkylene, wherein backbone of the alkylene can comprise one or more of O, S, SS and NR (R is hydrogen, alkyl, aryl) internally and/or at the end; and n is 0-2. In some embodiments, n is 1 or 2. It is understood that A is replacing the oxygen linked to 5' carbon of sugar. When n is 0, W and Y together with the P to which they are attached can form an optionally substituted 5-8 membered heterocyclic, wherein W an Y are each independently O, S, NR' or alkylene. Preferably the heterocyclic is substituted with an aryl or heteroaryl. In some embodiments, one or both hydrogen on C5' of the 5'-terminal nucleotides are replaced with a halogen, e.g., F.

Exemplary 5'-modifications include, but are not limited to, 5'-monophosphate ((HO)$_2$(O)P—O-5'); 5'-diphosphate ((HO)$_2$(O)P—O—P(HO)(O)—O-5'); 5'-triphosphate ((HO)$_2$ (O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates ((HO)$_2$(O)

P—NH-5', (HO)(NH$_2$)(O)P—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl (CH$_2$OMe), ethoxymethyl, etc. . . . ). Other exemplary 5'-modifications include where Z is optionally substituted alkyl at least once, e.g., ((HO)$_2$(X)P—O[—(CH$_2$)$_a$—O—P(X)(OH)—O]$_b$-5', ((HO)2(X)P—O[CH$_2$)$_a$—P(X)(OH)—O]$_b$-5', ((HO)2(X)P—[—(CH$_2$)$_a$—O—P(X)(OH)—O]$_b$-5'; dialkyl terminal phosphates and phosphate mimics: HO[—(CH$_2$)$_a$—O—P(X)(OH)—O]$_b$-5', H$_2$N[—(CH$_2$)$_a$—O—P(X)(OH)—O]$_b$-5', H[—(CH$_2$)$_a$—O—P(X)(OH)—O]$_b$-5', Me$_2$N[—(CH$_2$)$_a$—O—P(X)(OH)—O]$_b$-5', HO[—(CH$_2$)$_a$—P(X)(OH)—O]$_b$-5', H$_2$N[—(CH$_2$)$_a$—P(X)(OH)—O]$_b$-5', H[CH$_2$)$_a$—P(X)(OH)—O]$_b$-5', Me$_2$N[—(CH$_2$)$_a$—P(X)(OH)—O]$_b$-5', wherein a and b are each independently 1-10. Other embodiments, include replacement of oxygen and/or sulfur with BH$_3$, BH$_3^-$ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

Oligomeric Compounds

In certain embodiments, provided herein are oligomeric compounds having reactive phosphorus groups useful for forming linkages including for example phosphodiester and phosphorothioate internucleotide linkages. Methods of preparation and/or purification of precursors or oligomeric compounds are not a limitation of the compositions or methods provided herein. Methods for synthesis and purification of oligomeric compounds including DNA, RNA, oligonucleotides, oligonucleosides, and antisense compounds are well known to those skilled in the art.

Generally, oligomeric compounds comprise a plurality of monomeric subunits linked together by linking groups. Non-limiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self-complementarity to allow for hybridization and formation of a fully or partially double-stranded compound.

In certain embodiments, the present invention provides chimeric oligomeric compounds. In certain such embodiments, chimeric oligomeric compounds are chimeric oligonucleotides. In certain such embodiments, the chimeric oligonucleotides comprise differently modified nucleotides. In certain embodiments, chimeric oligonucleotides are mixed-backbone antisense oligonucleotides.

In general, a chimeric oligomeric compound will have modified nucleosides that can be in isolated positions or grouped together in regions that will define a particular motif. Any combination of modifications and/or mimetic groups can comprise a chimeric oligomeric compound as described herein.

In certain embodiments, chimeric oligomeric compounds typically comprise at least one region modified so as to confer increased resistance to nuclease degradation, increased cellular uptake, and/or increased binding affinity for the target nucleic acid. In certain embodiments, an additional region of the oligomeric compound may serve as a substrate for enzymes capable of cleaving RNA:DNA or RNA:RNA hybrids.

In certain embodiments, chimeric oligomeric compounds are gapmers. In certain such embodiments, a mixed-backbone oligomeric compound has one type of internucleotide linkages in one or both wings and a different type of internucleoside linkages in the gap. In certain such embodiments, the mixed-backbone oligonucleotide has phosphodiester linkages in the wings and phosphorothioate linkages in the gap. In certain embodiments in which the internucleotide linkages in a wing is different from the internucleotide linkages in the gap, the internucleotide linkage bridging that wing and the gap is the same as the internucleotide linkage in the wing. In certain embodiments in which the internucleotide linkages in a wing is different from the internucleotide linkages in the gap, the internucleotide linkage bridging that wing and the gap is the same as the internucleotide linkage in the gap.

In certain embodiments, the present invention provides oligomeric compounds, including siRNAs and tunable REVERSIR™ compounds of any of a variety of ranges of lengths. In certain embodiments, the invention provides oligomeric compounds consisting of X-Y linked oligonucleotides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-25, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleotides.

As noted-above, tunable REVERSIR™ compounds can be of any length. For example, in some embodiments, the tunable REVERSIR™ compound is a modified oligonucleotide consisting of 6-30 nucleotides. For example, the tunable REVERSIR™ compound can consist of 6, 7, 8, 9, 10, 11, 12, 13, 14, 15, 16, 17, 18, 19, 20, 21, 22, 23, 24, 25, 26, 27, 28, 29 or 30 linked nucleobases. In some embodiments, the tunable REVERSIR™ compound consists of 6-17, 7-16 or 8-15 linked nucleobases.

The inventors have discovered inter alia that tunable REVERSIR™ compounds, i.e., modified oligonucleotides, consisting of 15 or fewer nucleotides are particularly effective in reversing the siRNA activity. Accordingly, in some embodiments, the tunable REVERSIR™ compound is a modified oligonucleotide consisting of 8-15 (e.g., 8, 9, 10, 11, 12, 13, 14 or 15) linked nucleotides. In some embodiments, the tunable REVERSIR™ compound is a modified oligonucleotide consisting of 6-12, 7-11 or 8-10 linked nucleobases. In some embodiments, the tunable REVERSIR™ compound consists of 8-9 linked nucleobases.

As discussed herein, tunable REVERSIR™ compounds are modified oligonucleotides that are substantially complementary to at least one strand of an siRNA. Now without wishing to be bound by a theory, tunable REVERSIR™ compounds that are substantially complementary to the seed region of the antisense strand of the siRNA (i.e., at positions 2-8 of the 5'-end of the antisense strand) are particularly effective in reducing siRNA activity. Thus, in many embodiments, the tunable REVERSIR™ compound is substantially complementary to nucleotides 2-8, 2-9, 2-10, 2-11, 2-12, 2-13, 2-14, 2-15 or 2-16 of the antisense strand of the siRNA. By substantially complementary in this context is meant a complementarity of at least 90%, preferably at least 95%, and more preferably complete complementarity.

Ligands

In certain embodiments, oligomeric compounds are modified by covalent attachment of one or more conjugate groups. In general, conjugate groups modify one or more properties of the attached oligomeric compound including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Preferred conjugate groups amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., di-hexadecyl-rac-glycerol or triethylammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996, 277, 923).

Generally, a wide variety of entities, e.g., ligands, can be coupled to the oligomeric compounds described herein. Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g., steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)chonelic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a. helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, H2A peptides, *Xenopus* peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and branched polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptides include, but are not limited to,

```
                                            (SEQ ID NO: 1)
AALEALAEALEALAEALEALAEAAAAGGC (GALA);

(SEQ ID NO: 2)
AALAEALAEALAEALAEALAEALAAAAGGC;

(SEQ ID NO: 3)
ALEALAEALEALAEA;

(SEQ ID NO: 4)
GLFEAIEGFIENGWEGMIWDYG (INF-7);

(SEQ ID NO: 5)
GLFGAIAGFIENGWEGMIDGWYG (Inf HA-2);

(SEQ ID NO: 6)
GLFEAIEGFIENGWEGMIDGWYGCGLFEAIEGFIENGWEGMID GWYGC (diINF-7);

(SEQ ID NO: 7)
GLFEAIEGFIENGWEGMIDGGCGLFEAIEGFIENGWEGMIDGGC (diINF-3);

(SEQ ID NO: 8)
GLFGALAEALAEALAEHLAEALAEALEALAAGGC (GLF);

(SEQ ID NO: 9)
GLFEAIEGFIENGWEGLAEALAEALEALAAGGSC (GALA-INF3);

(SEQ ID NO: 10)
GLF EAI EGFI ENGW EGnI DG K GLF EAI EGFI ENGW

EGnI DG (INF-5, n is norleucine);

(SEQ ID NO: 11)
LFEALLELLESLWELLLEA (JTS-1);

(SEQ ID NO: 12)
GLFKALLKLLKSLWKLLLKA (ppTG1);

(SEQ ID NO: 13)
GLFRALLRLLRSLWRLLLRA (ppTG20);

(SEQ ID NO: 14)
WEAKLAKALAKALAKHLAKALAKALKACEA (KALA);

(SEQ ID NO: 15)
GLFFEAIAEFIEGGWEGLIEGC (HA);

(SEQ ID NO: 16)
GIGAVLKVLTTGLPALISWIKRKRQQ (Melittin);

(SEQ ID NO: 17)
H5WYG;
and (SEQ ID NO: 18)
CHK6HC.
```

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl (2,2-di ((9Z,12Z)-octadeca-9,12-di enyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (also referred to as XTC herein).

Synthetic polymers with endosomolytic activity amenable to the present invention are described in U.S. Pat. App. Pub. Nos. 2009/0048410; 2009/0023890; 2008/0287630; 2008/0287628; 2008/0281044; 2008/0281041; 2008/0269450; 2007/0105804; 20070036865; and 2004/0198687, contents of which are hereby incorporated by reference in their entirety.

Exemplary cell permeation peptides include, but are not limited to, RQIKIWFQNRRMKWKK (penetratin) (SEQ ID NO: 19); GRKKRRQRRRPPQC (Tat fragment 48-60) (SEQ ID NO: 20); GALFLGWL-GAAGSTMGAWSQPKKKRKV (signal sequence based peptide) (SEQ ID NO: 21); LLIILRRRIRKQAHAHSK (PVEC) (SEQ ID NO: 22); GWTLNSAGYLLKINLKA-LAALAKKIL (transportan) (SEQ ID NO: 23); KLALKLA-LKALKAALKLA (amphiphilic model peptide) (SEQ ID NO: 24); RRRRRRRRR (Arg9) (SEQ ID NO: 25); KFFKFFKFFK (Bacterial cell wall permeating peptide) (SEQ ID NO: 26); LLGDFFRK-SKEKIGKEFKRIVQRIKDFLRNLVPRTES (LL-37) (SEQ ID NO: 27); SWLSKTAKKLENSAKKRISEGIAIAI-QGGPR (cecropin P1) (SEQ ID NO: 28); ACYCRIPA-CIAGERRYGTCIYQGRLWAFCC (α-defensin) (SEQ ID NO: 29); DHYNCVSSGGQCLYSACPIFTKIQGT-CYRGKAKCCK ((3-defensin) (SEQ ID NO: 30); RRR-PRPPYLPRPRPPPFFPPRLPPRIPPGFPPRFPPRFPGKR-NH2 (PR-39) (SEQ ID NO: 31); ILPWKWPWWPWRR-NH2 (indoli ci din) (SEQ ID NO: 32); AAVALLPAVLLALLAP (RFGF) (SEQ ID NO: 33); AALLPVLLAAP (RFGF analogue) (SEQ ID NO: 34); and RKCRIVVIRVCR (bactenecin) (SEQ ID NO: 35).

Exemplary cationic groups include, but are not limited to, protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); and $NH(CH_2CH_2NH)$ $_n$CH$_2$CH$_2$-AMINE (AMINE=NH$_2$; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 51,410,104; 5,552,545; 6,335,434 and 7,128,893, contents of which are herein incorporated in their entireties by reference.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2, 4, 6-triiodophenol and flufenamic acid). Oligomeric compounds that comprise a number of phosphorothioate intersugar linkages are also known to bind to serum protein, thus short oligomeric compounds, e.g. oligonucleotides of comprising from about 5 to 30 nucleotides (e.g., 5 to 25 nucleotides, preferably 5 to 20 nucleotides, e.g., 5, 6, 7, 8, 9, 10, 11, 12, 13, 14, 15, 16, 17, 18, 19, or 20 nucleotides), and that comprise a plurality of phosphorothioate linkages in the backbone are also amenable to the present invention as ligands (e.g. as PK modulating ligands). The PK modulating oligonucleotide can comprise at least 3, 4, 5, 6, 7, 8, 9, 10, 11, 12, 13, 14, 15 or more phosphorothioate and/or phosphorodithioate linkages. In some embodiments, all internucleotide linkages in PK modulating oligonucleotide are phosphorothioate and/or phosphorodithioates linkages. In addition, aptamers that bind serum components (e.g. serum proteins) are also amenable to the present invention as PK modulating ligands. Binding to serum components (e.g. serum proteins) can be predicted from albumin binding assays, such as those described in Oravcova, et al., Journal of Chromatography B (1996), 677: 1-27.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

In some embodiments, ligand on one strand of a double-stranded oligomeric compound has affinity for a ligand on the second strand. In some embodiments, a ligand is covalently linked to both strands of a double-stranded oligomeric compound. As used herein, when a ligand is linked to more than oligomeric strand, point of attachment for an oligomeric compound can be an atom of the ligand self or an atom on a carrier molecule to which the ligand itself is attached.

Ligands can be coupled to the oligomeric compounds at various places, for example, 3'-end, 5'-end, and/or at an internal position. When two or more ligands are present, the ligand can be on opposite ends of an oligomeric compound. In preferred embodiments, the ligand is attached to the oligomeric compound via an intervening tether/linker. The ligand or tethered ligand can be present on a monomer when said monomer is incorporated into the growing strand. In some embodiments, the ligand can be incorporated via coupling to a "precursor" monomer after said "precursor" monomer has been incorporated into the growing strand. For example, a monomer having, e.g., an amino-terminated tether (i.e., having no associated ligand), e.g., monomer-linker-NH$_2$ can be incorporated into a growing oligomeric compound strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligomeric compounds, ligands can be attached to one or both strands. In some embodiments, an siRNA comprises a ligand conjugated to the sense strand. In other embodiments, an siRNA comprises a ligand conjugated to the antisense strand.

In some embodiments, ligand can be conjugated to nucleobases, sugar moieties, or internucleosidic linkages of oligomeric compound. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Inventors have discovered inter alia that tunable REVERSIR™ compounds conjugated with a ligand are particularly effective in reducing activity of siRNAs. Without wishing to be bound by a theory, a ligand can increase or enhance the ability of a tunable REVERSIR™ compound by delivering the tunable REVERSIR™ compound to the desired location of action. Accordingly, in some embodiments, the tunable REVERSIR™ compound is conjugated with a ligand.

While useful in delivery of the tunable REVERSIR™ compound to a desired location of action, the ligand conjugated with the tunable REVERSIR™ compound can negatively affect the ability of the tunable REVERSIR™ compound to reduce siRNA activity. Therefore, in some embodiments, the linkage between the ligand and the tunable REVERSIR™ compound can be designed to undergo cleavage after the tunable REVERSIR™ compound reaches a desired location of action. This can be accomplished in a number of ways. For example, the linker connecting the tunable REVERSIR™ compound to the ligand can be a cleavable linker.

The inventors have also discovered that the nucleotide in the tunable REVERSIR™ compound that is connected with the ligand can have an effect on the ability of the tunable REVERSIR™ compound to reduce activity of the siRNA. Inventors have discovered that ligand conjugated nucleotides comprising deoxy sugars (e.g., 2'-deoxy ribose) are particularly effective in enhancing the ability of tunable REVERSIR™ compounds to reduce siRNA activity. Accordingly, in some embodiments, the nucleotide conjugated with the ligand comprises a deoxy sugar, for example, a 2'-deoxy sugar.

In some embodiments of the various aspects disclosed herein, the ligand is attached to the nucleotide at the 3'-terminus of the tunable REVERSIR™ compound. The inventors have discovered inter alia that internucleotide linkage between the ligand conjugated nucleotide and the rest of the tunable REVERSIR™ compound can also have an effect on the ability of the tunable REVERSIR™ compound to reduce siRNA activity. Without wishing to be bound by a theory, readily cleavable internucleotide linkages were found to be particularly effective in enhancing the ability of tunable REVERSIR™ compounds to reduce siRNA activity. Accordingly, in some embodiments, the ligand conjugated nucleotide is attached to the rest of the tunable REVERSIR™ compound via a cleavable internucleotide linage. In some embodiment, the cleavable internucleotide linkage is a phosphodiester internucleotide linkage.

In some embodiments, the ligand conjugated nucleotide comprises a deoxy sugar and is linked to rest of the tunable REVERSIR™ compound via a cleavable internucleotide linkage. In some further embodiments, of this the cleavable internucleotide linkage is a phosphodiester linkage.

In some embodiments, the ligand conjugated nucleotide comprises a deoxy sugar and is linked to rest of the tunable REVERSIR™ compound via an internucleotide linkage that is not a phosphodiester linkage.

In some embodiments, the ligand is conjugated to the nucleotide at the 3'-terminus of the tunable REVERSIR™ compound.

In some embodiments, the ligand is conjugated at the 5'-terminus of the tunable REVERSIR™ compound. In some embodiments, a first ligand is conjugated at the 5'-terminus of the tunable REVERSIR™ compound and a second ligand conjugated to the first ligand.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative U.S. patents that teach the preparation of conjugates of oligomeric compounds, e.g., oligonucleotides, include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; contents of which are herein incorporated in their entireties by reference.

In certain embodiments, the oligomeric compound described herein, including but not limited to tunable REVERSIR™ compounds and siRNAs, comprises a ligand having a structure shown below:

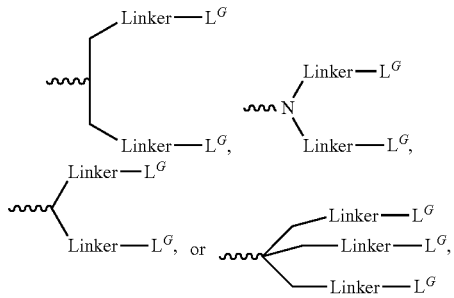

wherein:

$L^G$ is independently for each occurrence a ligand, e.g., carbohydrate, e.g. monosaccharide, disaccharide, trisaccharide, tetrasaccharide, polysaccharide; and Z', Z'', Z''' and Z'''' are each independently for each occurrence O or S.

In certain embodiments, the oligomeric compound described herein, including but not limited to tunable REVERSIR™ compounds and siRNAs, comprises a ligand of Formula (II), (III), (IV) or (V):

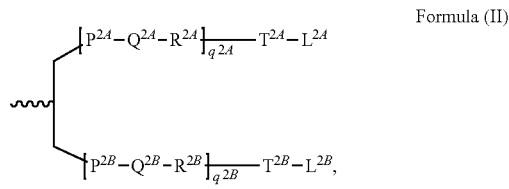

Formula (II)

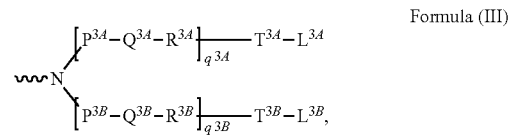

Formula (III)

-continued

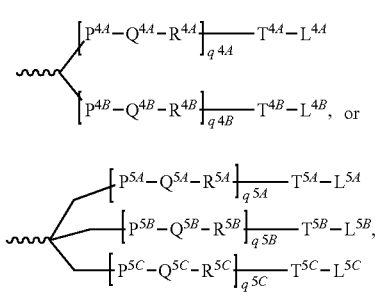

Formula (IV)

Formula (V)

wherein:
$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;
Q and Q' are independently for each occurrence is absent, $-(P^7-Q^7-R^7)_p-T^7-$ or $-T^7-Q^7-T^{7'}-B-T^{8'}-Q^8-T^8$;
$p^{2A}$, $p^{2B}$, $p^{3A}$, $p^{3B}$, $p^{4A}$, $p^{4B}$, $p^{5A}$, $p^{5B}$, $p^{5C}$, $P^7$, $T^{2A}$, $T^{2B}$, $T^{3A}$, $T^{3B}$, $T^{4A}$, $T^{4B}$, $T^{4A}$, $T^{5B}$, $T^{5C}$, $T^7$, $T^{7'}$, $T^8$ and $T^{8'}$ are each independently for each occurrence absent, CO, NH, O, S, OC(O), NHC(O), $CH_2$, $CH_2NH$ or $CH_2O$;
B is $-CH_2-N(B\ L)-CH_2-$;
$B^L$ is $-T^B-Q^B-T^{B'}-R^x$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$, $Q^7$, $Q^8$ and $Q^B$ are independently for each occurrence absent, alkylene, substituted alkylene and wherein one or more methylenes can be interrupted or terminated by one or more of O, S, S(O), $SO_2$, $N(R^N)$, $C(R')=C(R')$, $C\equiv C$ or $C(O)$;
$T^B$ and $T^{B'}$ are each independently for each occurrence absent, CO, NH, O, S, OC(O), OC(O)O, NHC(O), NHC(O)NH, NHC(O)O, $CH_2$, $CH_2NH$ or $CH_2O$;
$R^x$ is a lipophile (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, Friedelin, epifriedelanol derivatized lithocholic acid), or a cationic lipid;
$R^1$, $R^2$, $R^{2A}$, $R^{2B}$, $R^{3A}$, $R^{3B}$, $R^{4A}$, $R^{4B}$, $R^{5A}$, $R^{5B}$, $R^{5C}$, $R^7$ are each independently for each occurrence absent, NH, O, S, $CH_2$, C(O)O, C(O)NH, $NHCH(R^a)C(O)$, $-C(O)-CH(R^a)-NH-$, CO, $CH=N-O$,

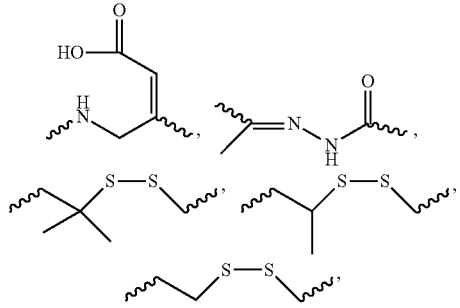

or heterocyclyl;
$L^1$, $L^{2A}$, $L^{2B}$, $L^{3A}$, $L^{3B}$, $L^{4A}$, $L^{4B}$, $L^{5A}$, $L^{5B}$ and $L^{5C}$ are each independently for each occurrence a carbohydrate, e.g., monosaccharide, disaccharide, trisaccharide, tetrasaccharide, oligosaccharide and polysaccharide;
R' and R" are each independently H, $C^1$-$C_6$ alkyl, OH, SH, or $N(R^N)_2$;
$R^N$ is independently for each occurrence H, methyl, ethyl, propyl, isopropyl, butyl or benzyl;
$R^a$ is H or amino acid side chain;
Z', Z", Z''' and Z'''' are each independently for each occurrence O or S;
p represent independently for each occurrence 0-20.

In certain embodiments, the oligomeric compound described herein, including but not limited to tunable REVERSIR™ compounds and siRNAs, comprises a ligand of structure:

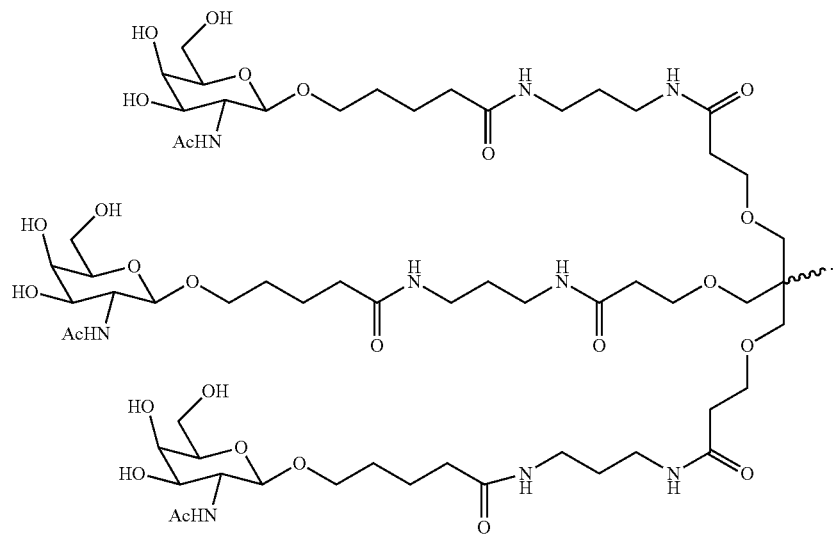 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the oligomeric compound described herein, including but not limited to tunable REVERSIR™ compounds and siRNAs, comprises a ligand of structure:

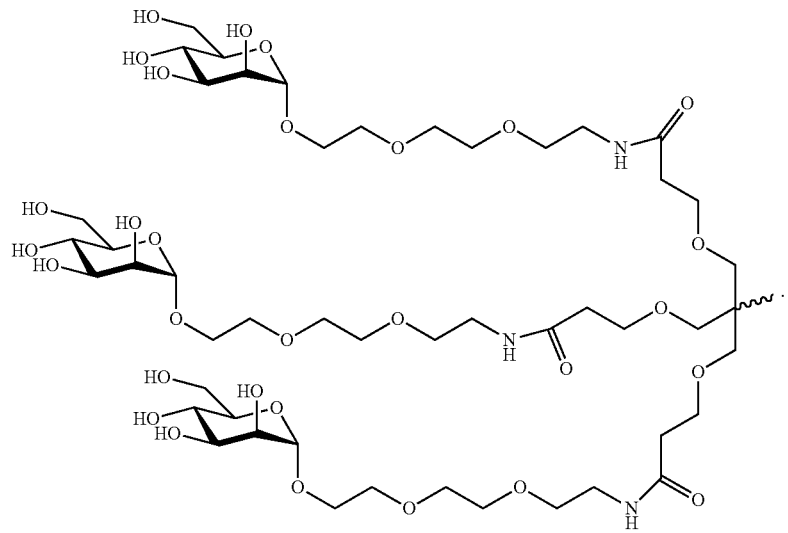

In certain embodiments, the oligomeric compound described herein, including but not limited to tunable REVERSIR™ compounds and siRNAs, comprises a ligand of structure:

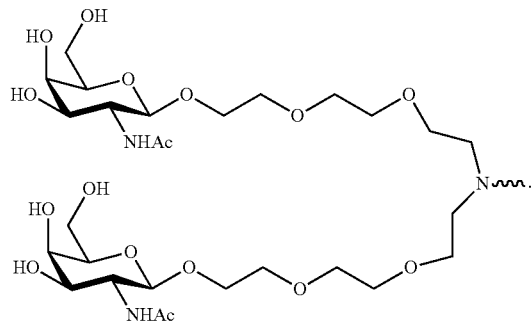

In certain embodiments, the oligomeric compound described herein, including but not limited to tunable REVERSIR™ compounds and siRNAs, comprises a ligand of structure:

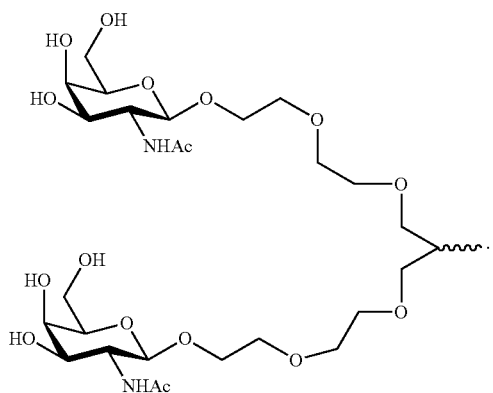

In certain embodiments, the oligomeric compound described herein, including but not limited to tunable REVERSIR™ compounds and siRNAs, comprises a ligand of structure:

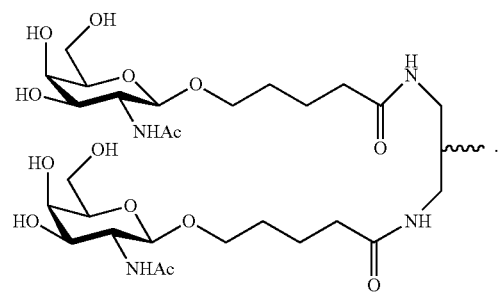

In certain embodiments, the oligomeric compound described herein, including but not limited to tunable REVERSIR™ compounds and siRNAs, comprises a ligand of structure:

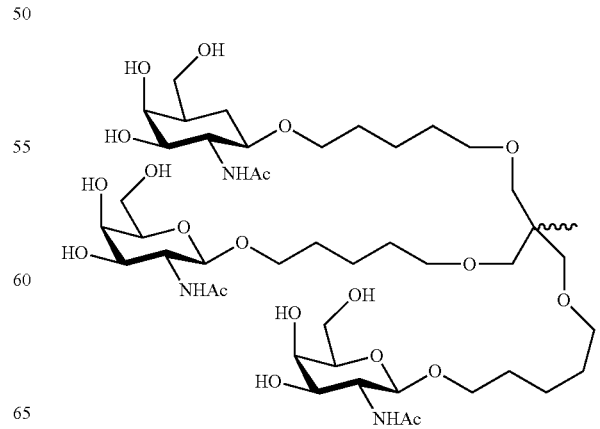

In certain embodiments, the oligomeric compound described herein, including but not limited to tunable REVERSIR™ compounds and siRNAs, comprises a ligand of structure:

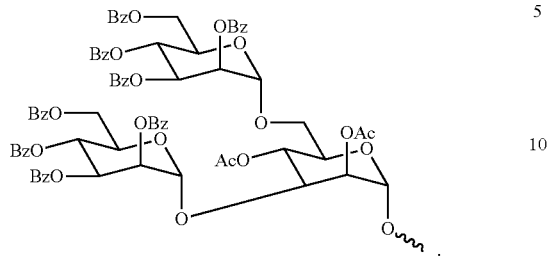

In certain embodiments, the oligomeric compound described herein, including but not limited to tunable REVERSIR™ compounds and siRNAs, comprises a ligand of structure:

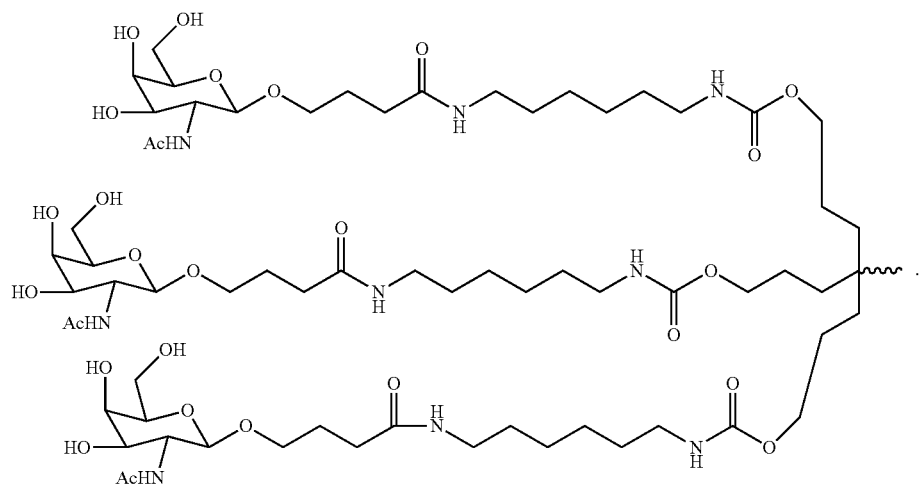 [SMILES: CC(=O)NC1C(OCCCC(=O)NCCCCCCNC(=O)OCCCCC(C)(CCCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]

In certain embodiments, the oligomeric compound described herein, including but not limited to tunable REVERSIR™ compounds and siRNAs, comprises a ligand of structure:

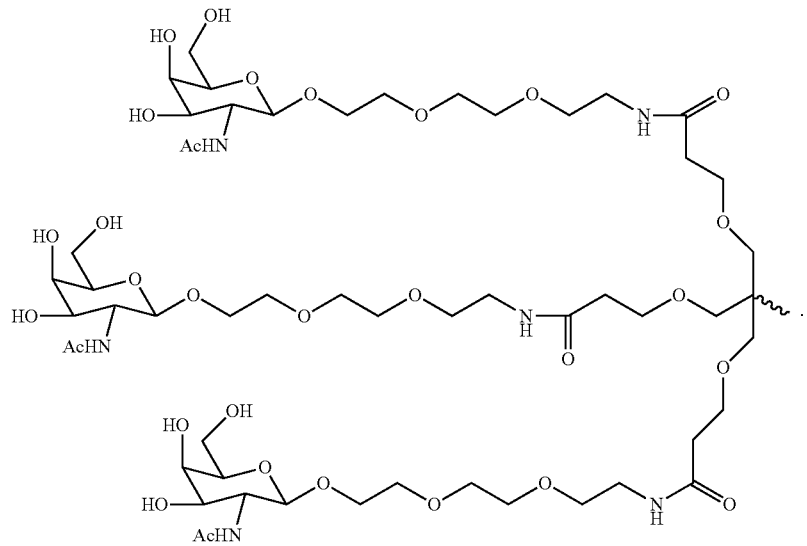 [SMILES: CC(=O)NC1C(OCCOCCOCCNC(=O)CCOCC(C)(COCCC(=O)NCCOCCOCCOC2OC(CO)C(O)C(O)C2NC(C)=O)COCCC(=O)NCCOCCOCCOC2OC(CO)C(O)C(O)C2NC(C)=O)OC(CO)C(O)C1O]

In certain embodiments, the oligomeric compound described herein, including but not limited to tunable REVERSIR™ compounds and siRNAs, comprises a ligand of structure:

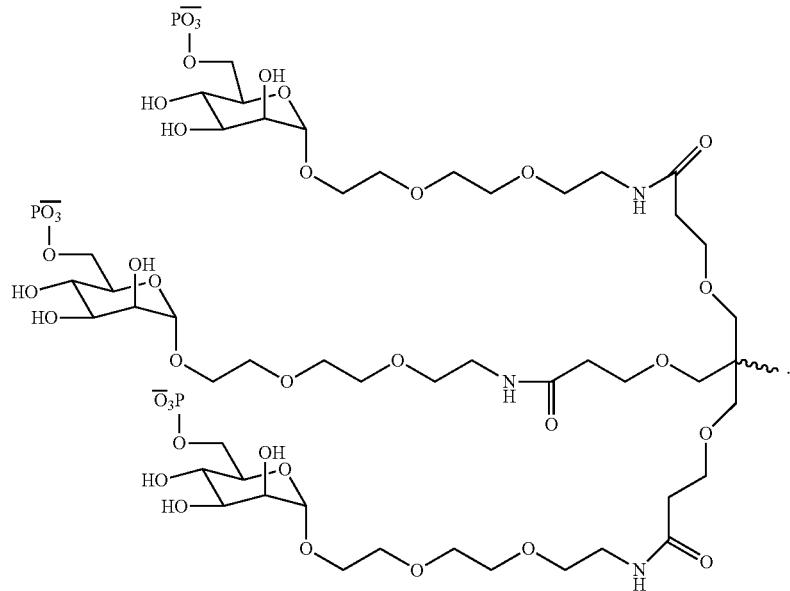

In certain embodiments, the oligomeric compound described herein, including but not limited to tunable REVERSIR™ compounds and siRNAs, comprises a ligand of structure:

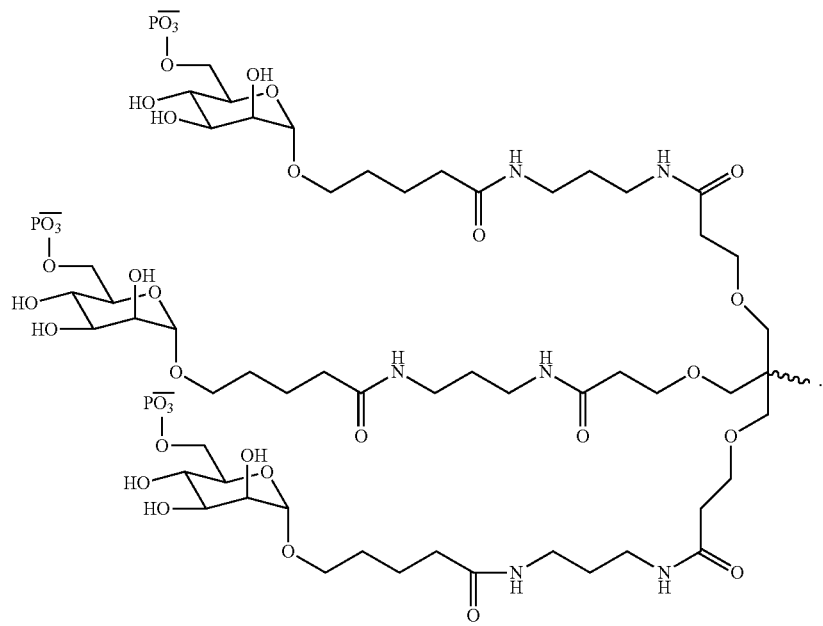

In certain embodiments, the oligomeric compound described herein, including but not limited to tunable REVERSIR™ compounds and siRNAs, comprises a monomer of structure:

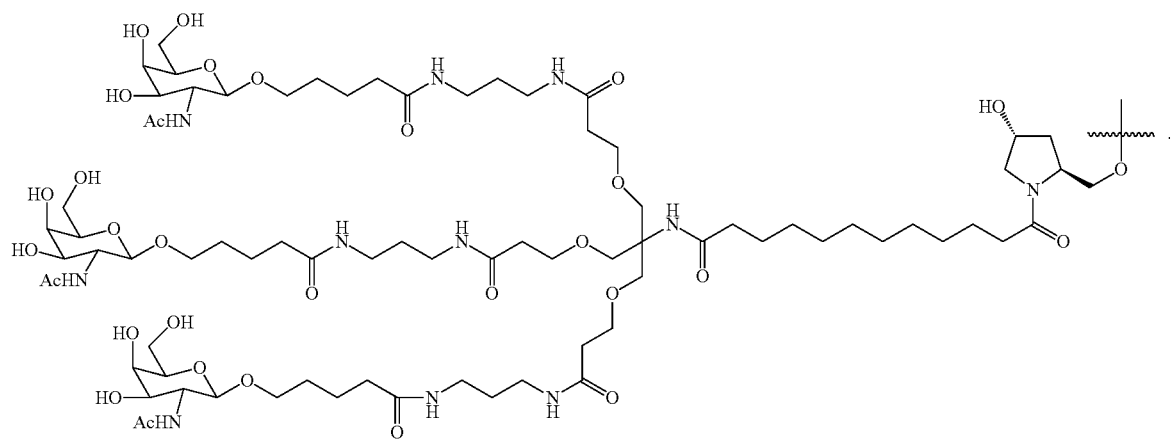 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

In certain embodiments, the oligomeric compound described herein, including but not limited to tunable REVERSIR™ compounds and siRNAs, comprises a ligand of structure:

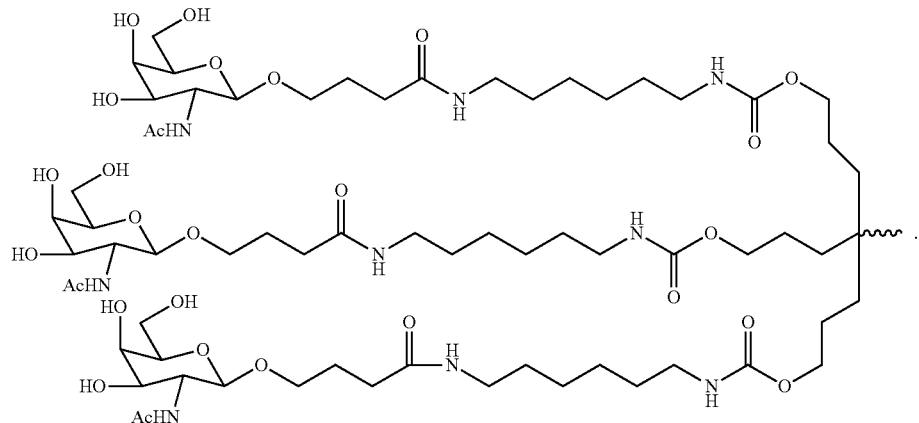 [SMILES: CC(=O)NC1C(OCCCC(=O)NCCCCCCNC(=O)OCCCC(C)(CCCOC(=O)NCCCCCCNC(=O)CCCOC2OC(CO)C(O)C(O)C2NC(C)=O)CCCOC(=O)NCCCCCCNC(=O)CCCOC2OC(CO)C(O)C(O)C2NC(C)=O)OC(CO)C(O)C1O]

In certain embodiments, the oligomeric compound described herein, including but not limited to tunable REVERSIR™ compounds and siRNAs, comprises a monomer of structure:

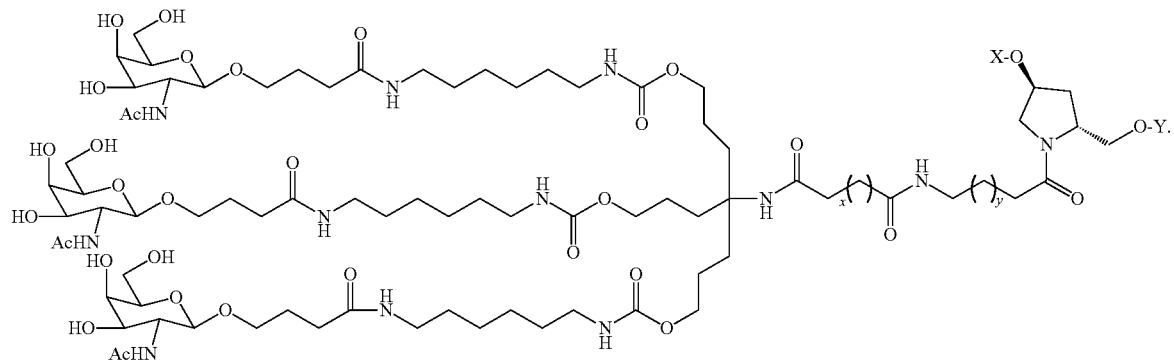

$x = 1\text{-}30$
$y = 1\text{-}15$

In certain embodiments, the oligomeric compound described herein, including but not limited to tunable REVERSIR™ compounds and siRNAs, comprises a monomer of structure:

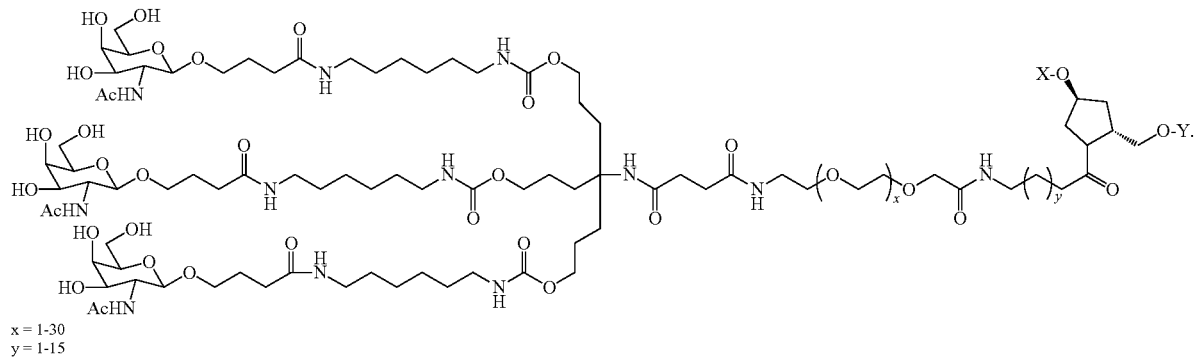

x = 1-30
y = 1-15

In certain embodiments, the oligomeric compound described herein, including but not limited to tunable REVERSIR™ compounds and siRNAs, comprises a monomer of structure:

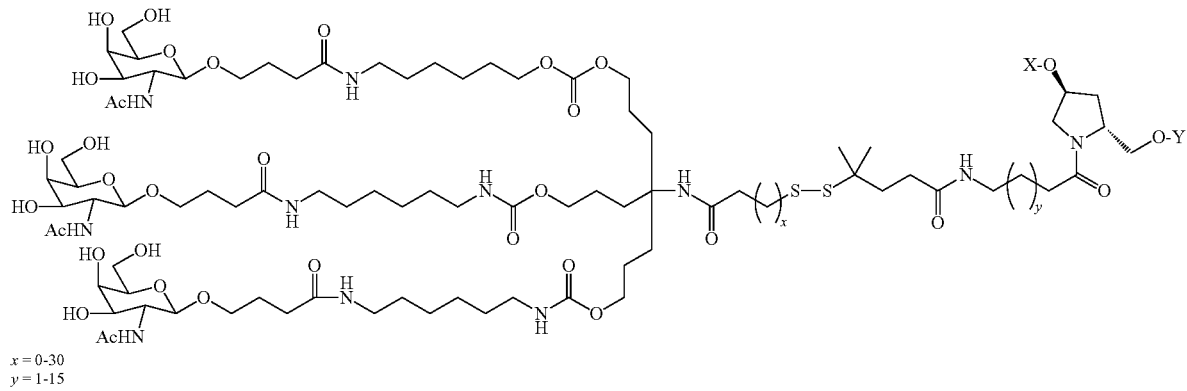

x = 0-30
y = 1-15

In certain embodiments, the oligomeric compound described herein, including but not limited to tunable REVERSIR™ compounds and siRNAs, comprises a monomer of structure:

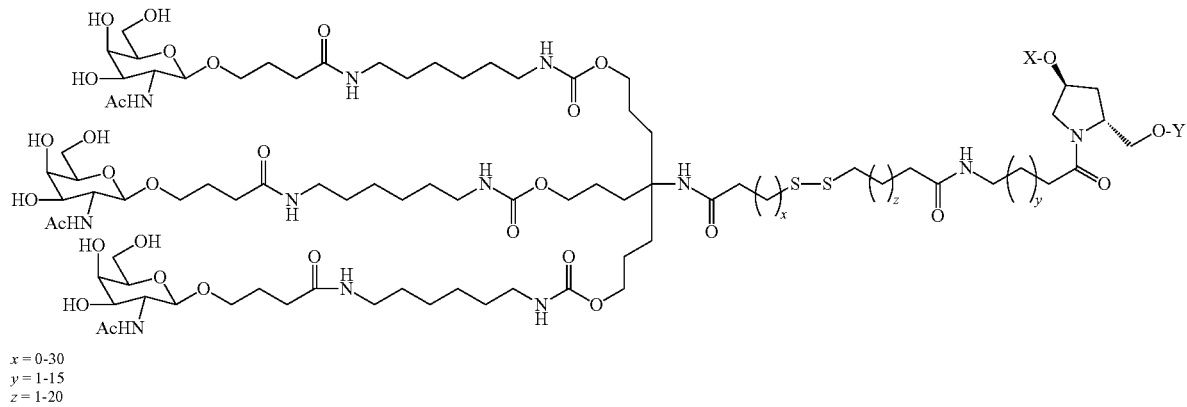

x = 0-30
y = 1-15
z = 1-20

In certain embodiments, the oligomeric compound described herein, including but not limited to tunable REVERSIR™ compounds and siRNAs, comprises a monomer of structure:

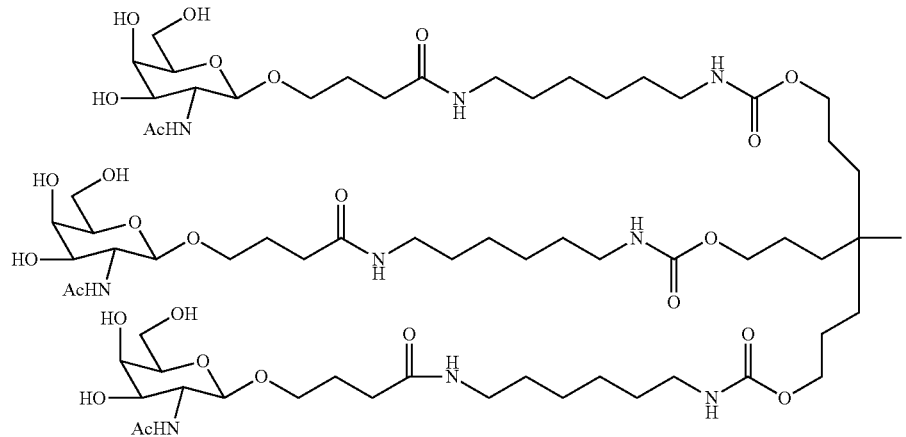

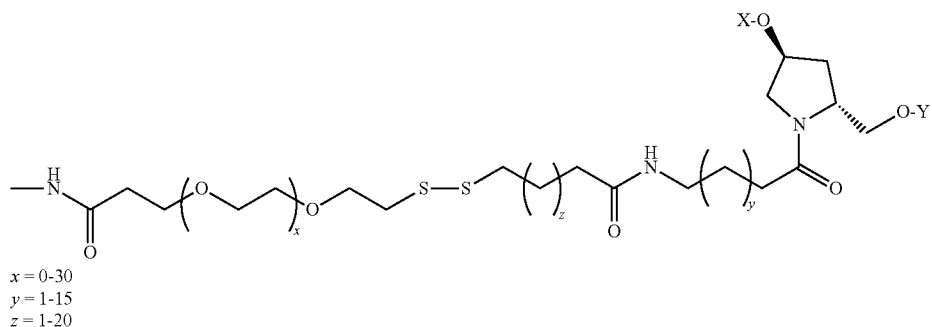

$x = 0\text{-}30$
$y = 1\text{-}15$
$z = 1\text{-}20$

In certain embodiments, the oligomeric compound described herein, including but not limited to tunable REVERSIR™ compounds and siRNAs, comprises a monomer of structure:

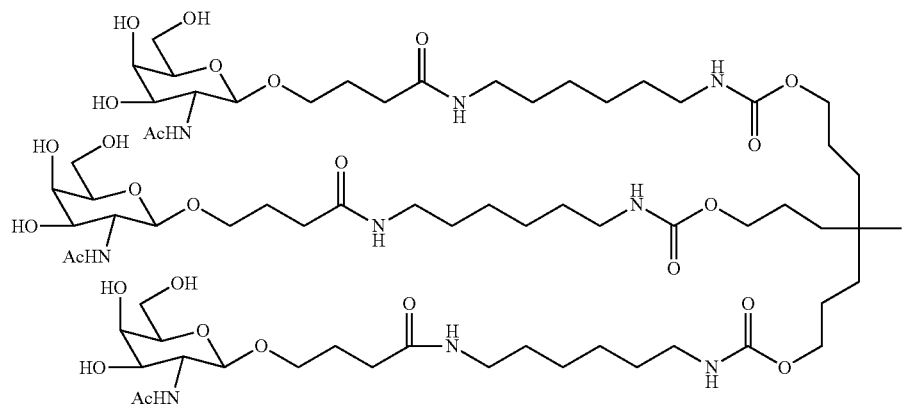

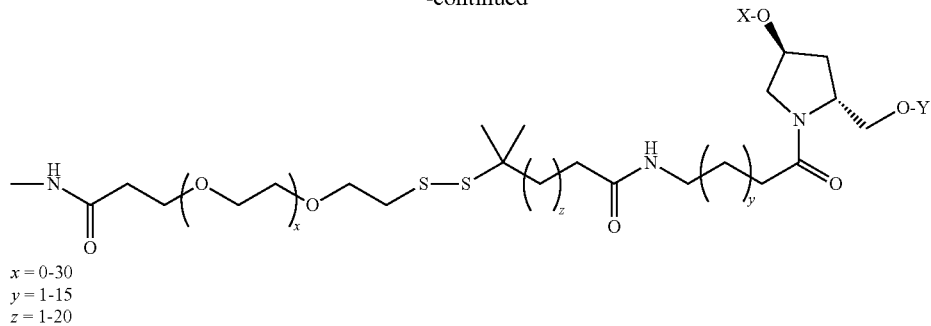

x = 0-30
y = 1-15
z = 1-20

In certain embodiments, the oligomeric compound described herein, including but not limited to tunable REVERSIR™ compounds and siRNAs, comprises a ligand of structure:

In certain embodiments, the oligomeric compound described herein, including but not limited to tunable REVERSIR™ compounds and siRNAs, comprises a ligand of structure:

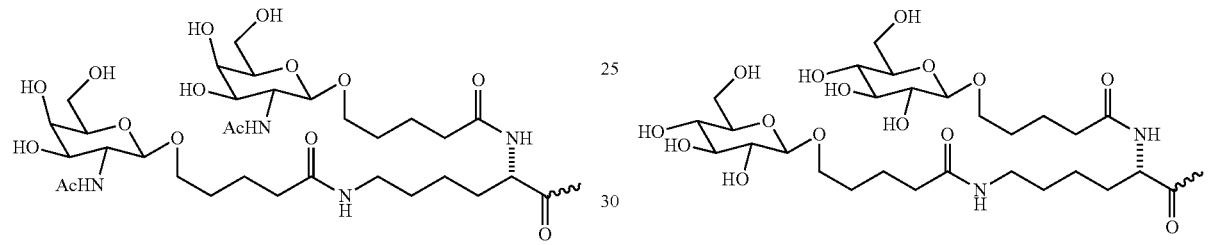

In certain embodiments, the oligomeric compound described herein, including but not limited to tunable REVERSIR™ compounds and siRNAs, comprises a ligand of structure:

In certain embodiments, the oligomeric compound described herein, including but not limited to tunable REVERSIR™ compounds and siRNAs, comprises a ligand of structure:

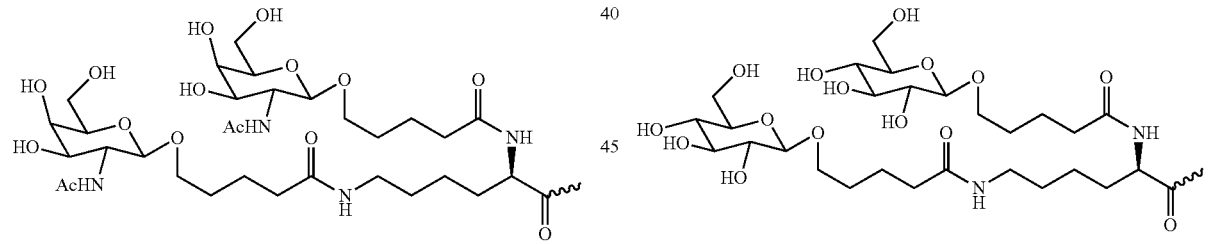

In certain embodiments, the oligomeric compound described herein, including but not limited to tunable REVERSIR™ compounds and siRNAs, comprises a ligand of structure:

In certain embodiments, the oligomeric compound described herein, including but not limited to tunable REVERSIR™ compounds and siRNAs, comprises a ligand of structure:

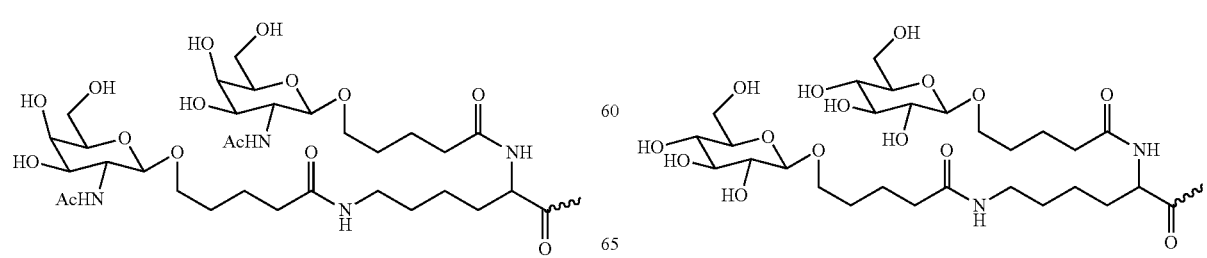

In certain embodiments, the oligomeric compound described herein, including but not limited to tunable REVERSIR™ compounds and siRNAs, comprises a ligand of structure:

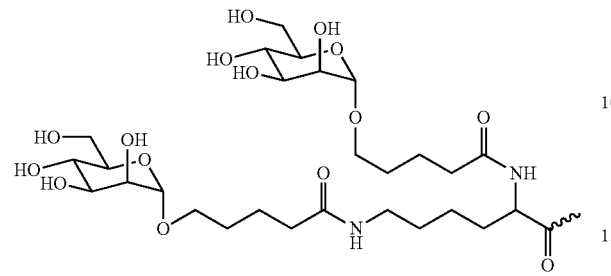

In certain embodiments, the oligomeric compound described herein, including but not limited to tunable REVERSIR™ compounds and siRNAs, comprises a ligand of structure:

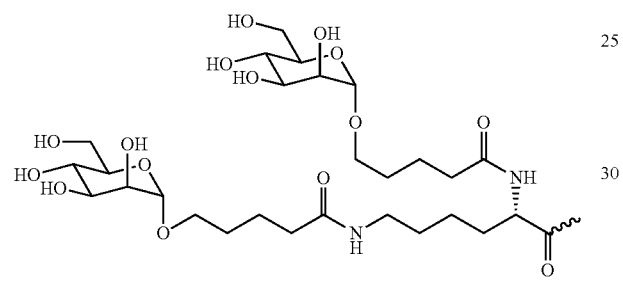

In certain embodiments, the oligomeric compound described herein, including but not limited to tunable REVERSIR™ compounds and siRNAs, comprises a ligand of structure:

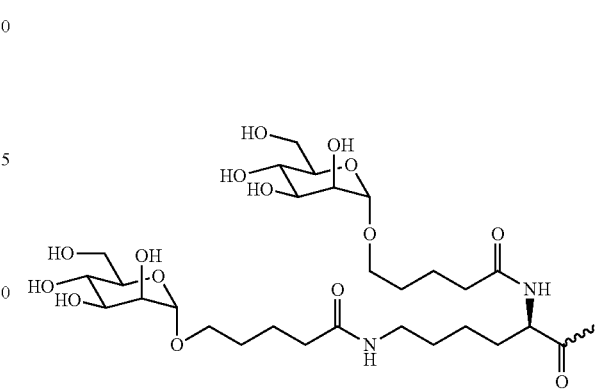

In certain embodiments, the oligomeric compound described herein, including but not limited to tunable REVERSIR™ compounds and siRNAs, comprises a monomer of structure:

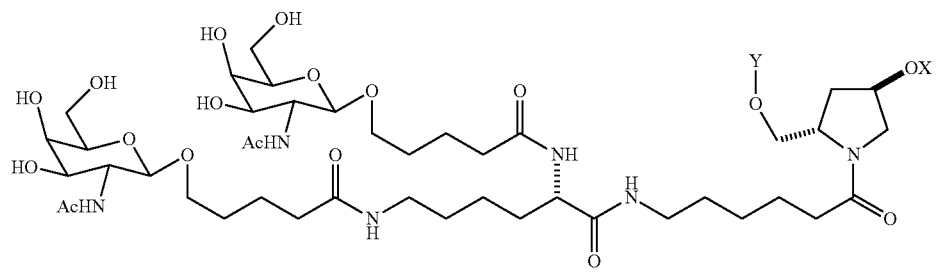

In certain embodiments, the oligomeric compound described herein, including but not limited to tunable REVERSIR™ compounds and siRNAs, comprises a monomer of structure:

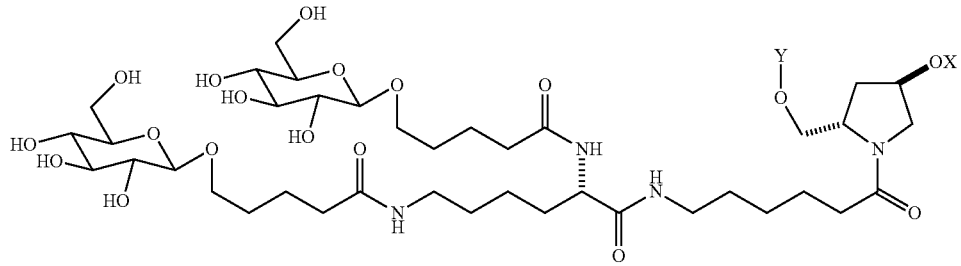

In certain embodiments, the oligomeric compound described herein, including but not limited to tunable REVERSIR™ compounds and siRNAs, comprises a monomer of structure:

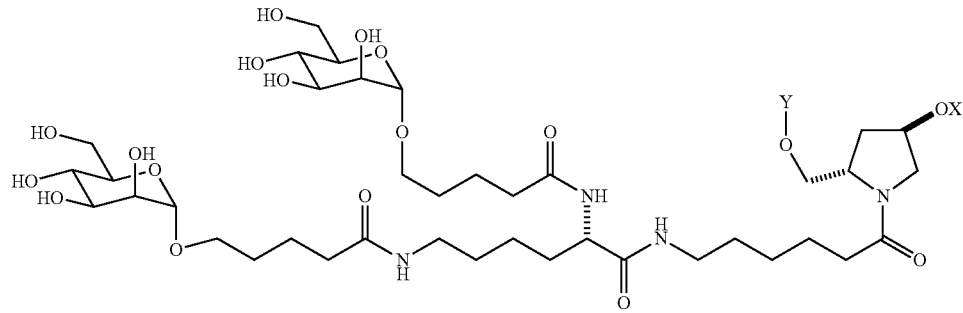

In certain embodiments, the oligomeric compound described herein, including but not limited to tunable REVERSIR™ compounds and siRNAs, comprises a monomer of structure:

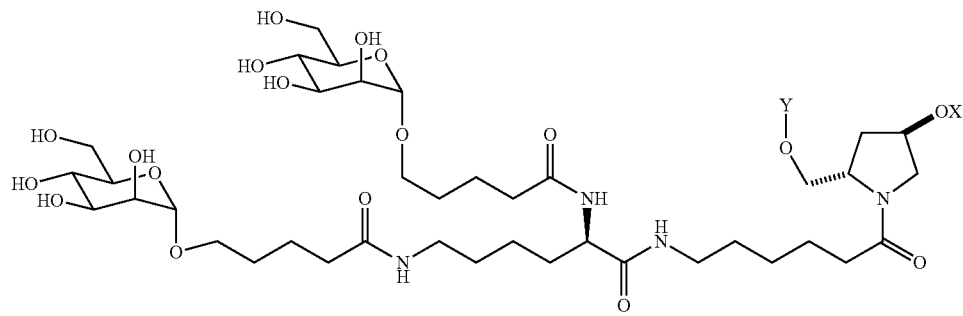

In certain embodiments, the oligomeric compound described herein, including but not limited to tunable REVERSIR™ compounds and siRNAs, comprises a monomer of structure:

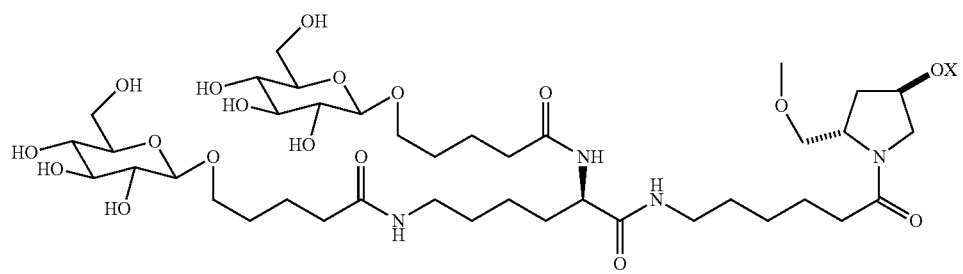

In certain embodiments, the oligomeric compound described herein, including but not limited to tunable REVERSIR™ compounds and siRNAs, comprises a monomer of structure:

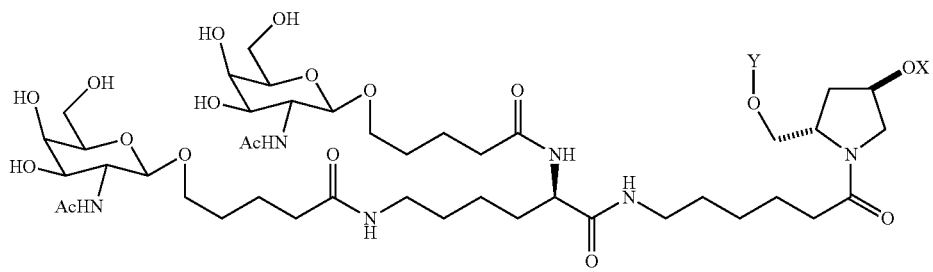

In some embodiments both $L^{2A}$ and $L^{2B}$ are different.
In some preferred embodiments both $L^{3A}$ and $L^{3B}$ are the same.
In some embodiments both $L^{3A}$ and $L^{3B}$ are different.
In some preferred embodiments both $L^{4A}$ and $L^{4B}$ are the same.
In some embodiments both $L^{4A}$ and $L^{4B}$ are different.
In some preferred embodiments all of $L^{5A}$, $L^{5B}$ and $L^{5C}$ are the same.
In some embodiments two of $L^{5A}$, $L^{5B}$ and $L^{5C}$ are the same.
In some embodiments $L^{5A}$ and $L^{5B}$ are the same.
In some embodiments $L^{5A}$ and $L^{5C}$ are the same.
In some embodiments $L^{5B}$ and $L^{5C}$ are the same.

In certain embodiments, the oligomeric compound described herein, including but not limited to tunable REVERSIR™ compounds and siRNAs, comprises a monomer of structure:

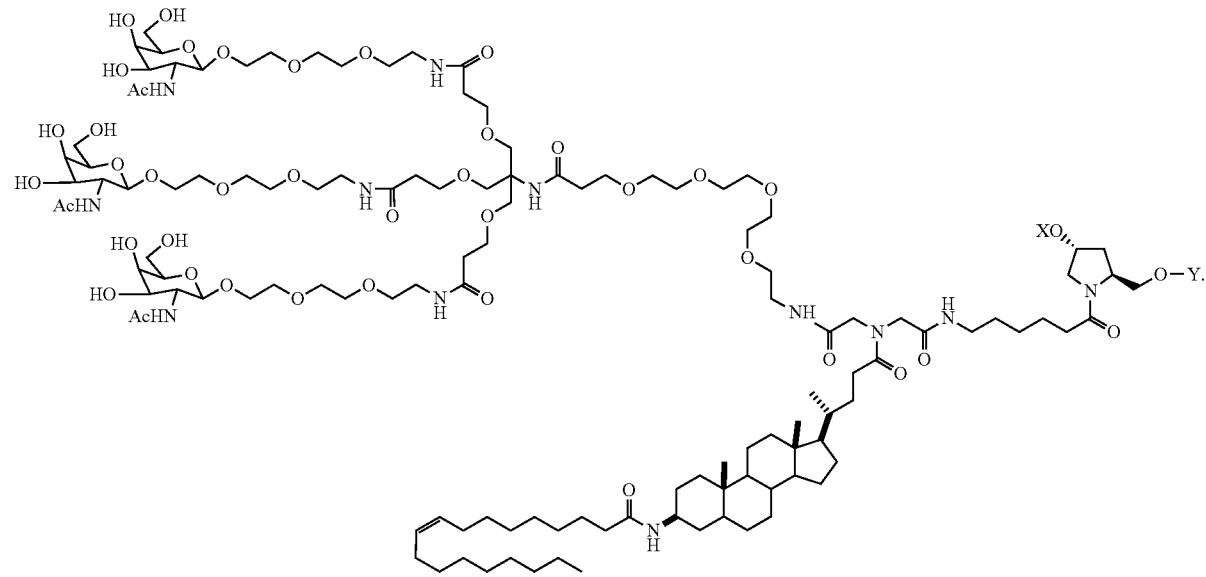

In certain embodiments, the oligomeric compound described herein, including but not limited to tunable REVERSIR™ compounds and siRNAs, comprises a monomer of structure:

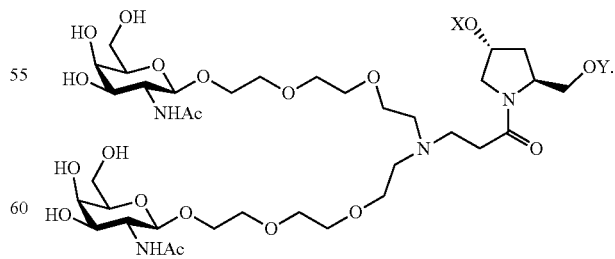

In certain embodiments, the oligomeric compound described herein, including but not limited to tunable REVERSIR™ compounds and siRNAs, comprises a monomer of structure:

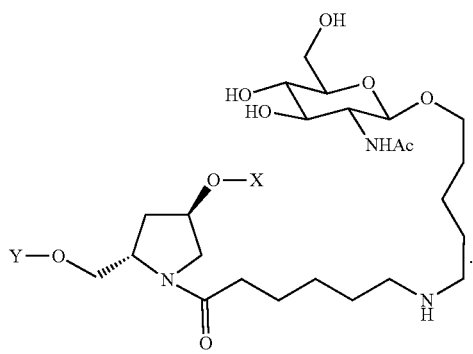

In certain embodiments, the oligomeric compound described herein, including but not limited to tunable REVERSIR™ compounds and siRNAs, comprises a monomer of structure:

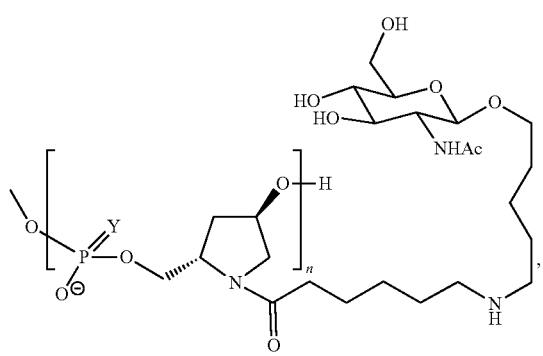

wherein Y is O or S and n is 3-6.

In certain embodiments, the oligomeric compound described herein, including but not limited to tunable REVERSIR™ compounds and siRNAs, comprises a monomer of structure:

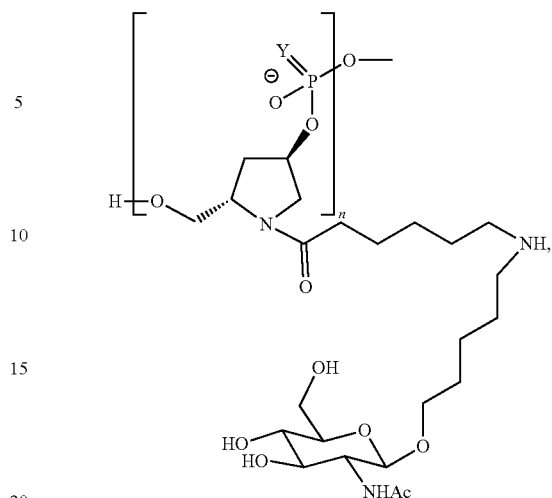

wherein Y is O or S and n is 3-6.

In certain embodiments, the oligomeric compound described herein, including but not limited to tunable REVERSIR™ compounds and siRNAs, comprises a monomer of structure:

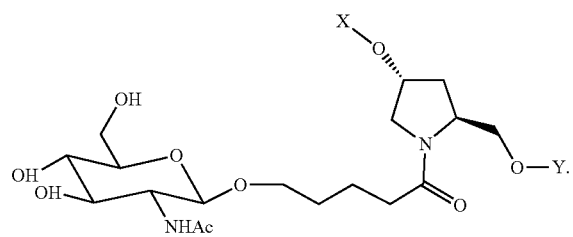

In certain embodiments, the oligomeric compound described herein, including but not limited to tunable REVERSIR™ compounds and siRNAs, comprises a monomer of structure:

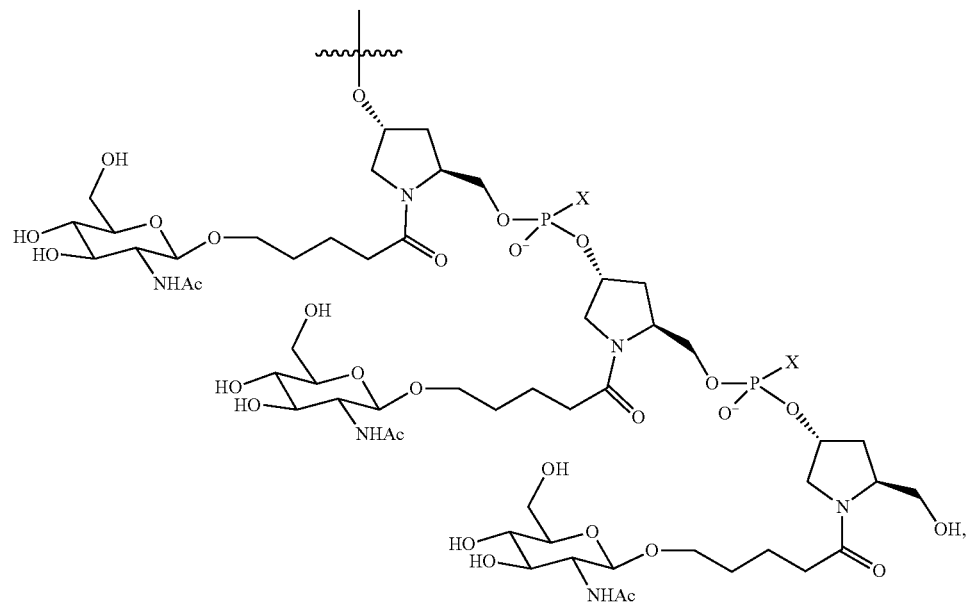

wherein X is O or S.

In certain embodiments, the oligomeric compound described herein, including but not limited to tunable REVERSIR™ compounds and siRNAs, comprises a monomer selected from the group consisting of:
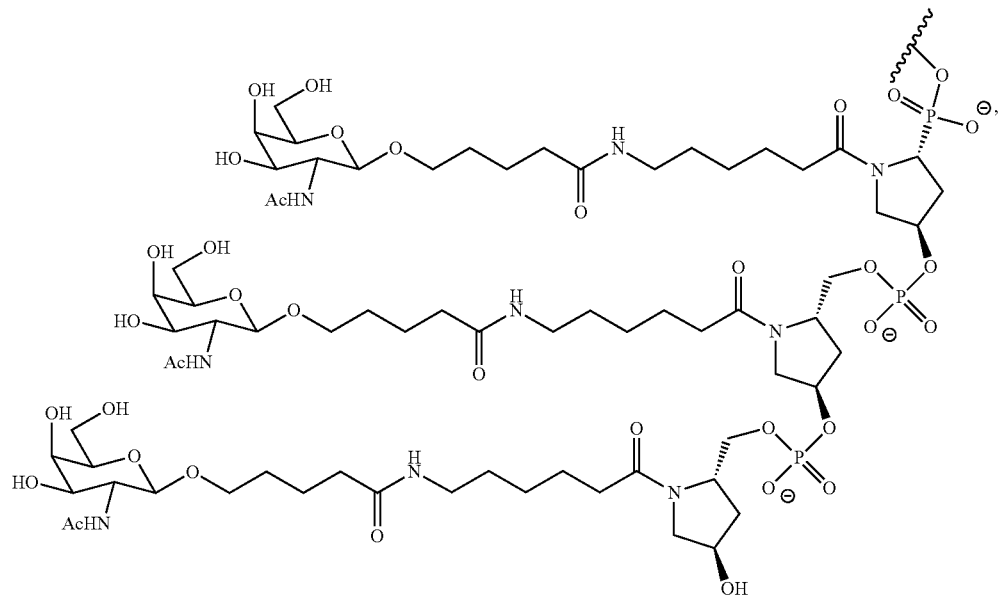
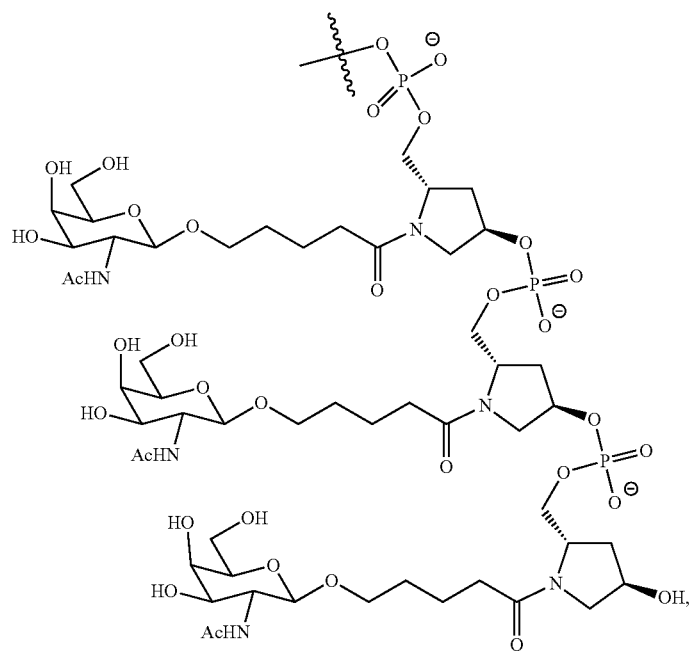

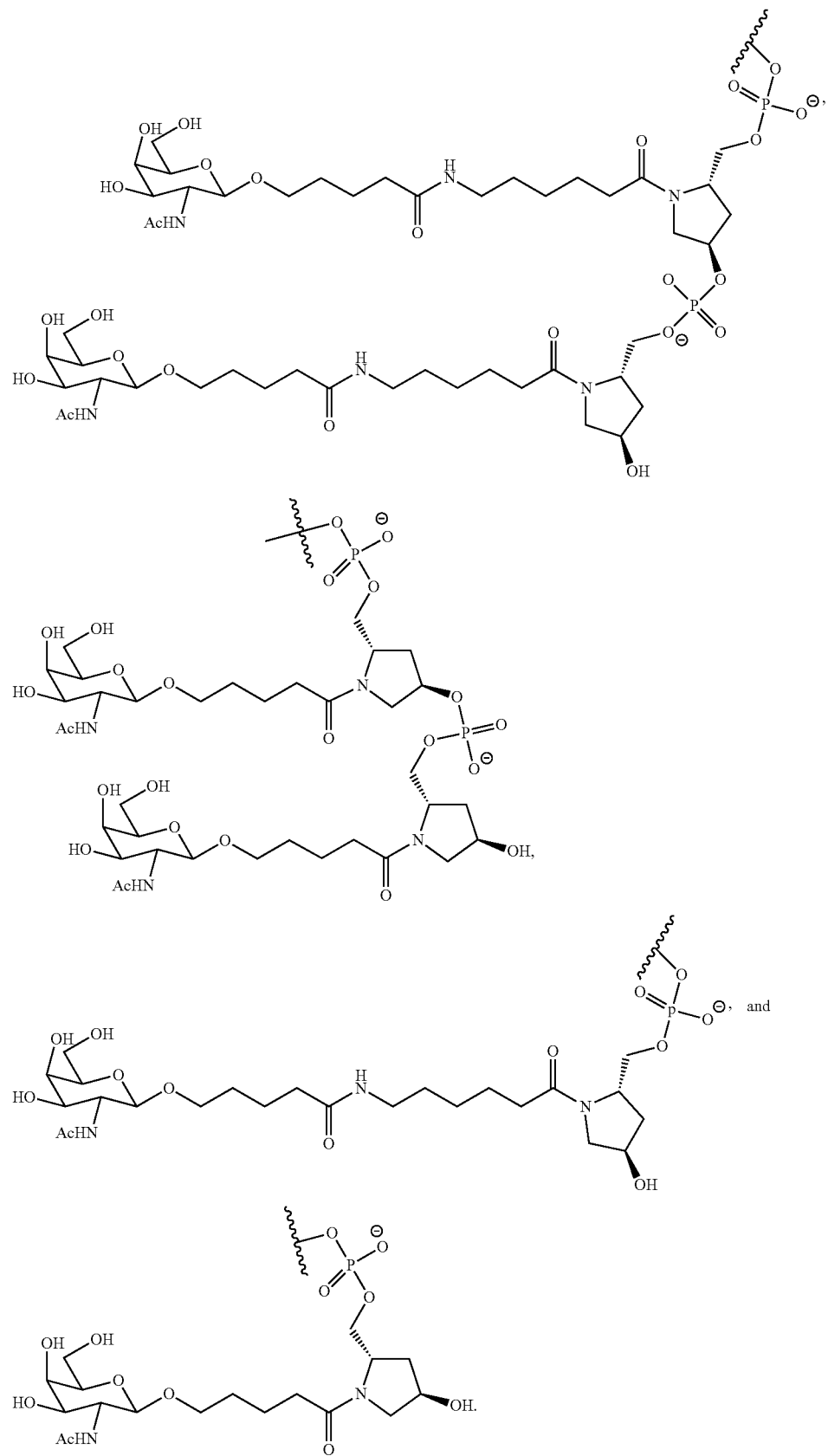

In certain embodiments, the oligomeric compound described herein, including but not limited to tunable REVERSIR™ compounds and siRNAs, comprises a monomer of structure:

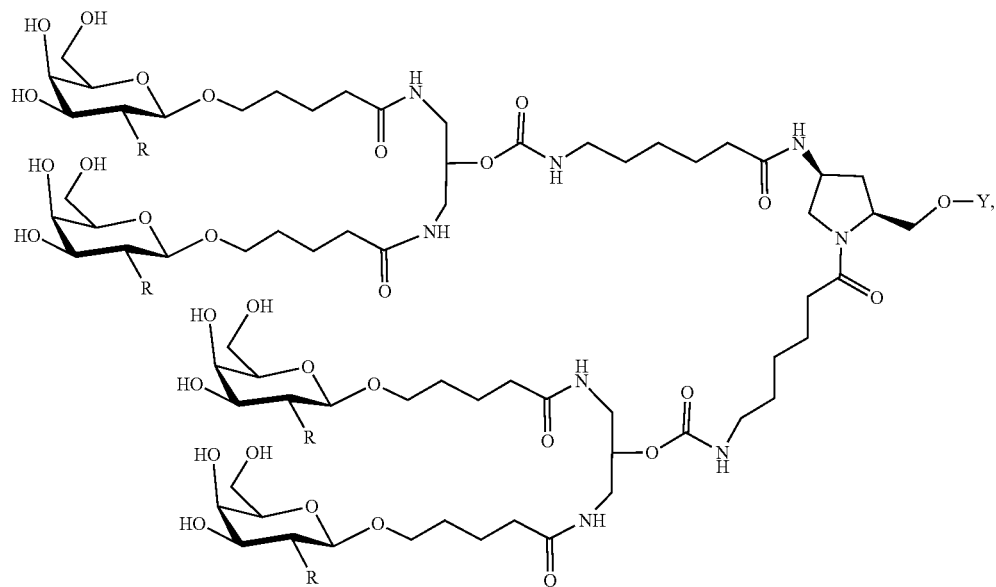

wherein R is OH or NHCOOH.

In certain embodiments, the oligomeric compound described herein, including but not limited to tunable REVERSIR™ compounds and siRNAs, comprises a monomer of structure:

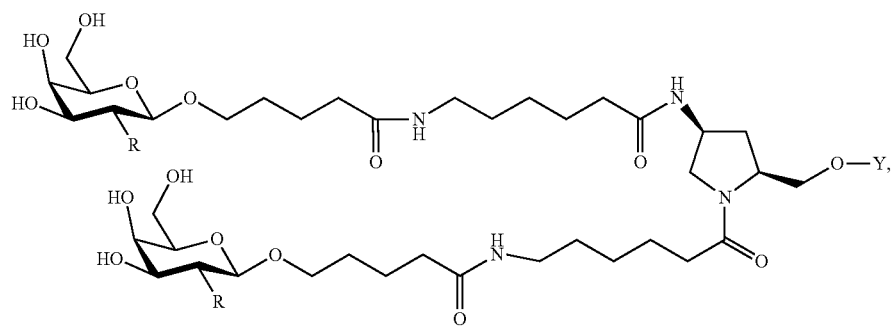

wherein R is OH or NHCOOH.

In certain embodiments, the oligomeric compound described herein, including but not limited to tunable REVERSIR™ compounds and siRNAs, comprises a monomer of structure:

Formula (VII)

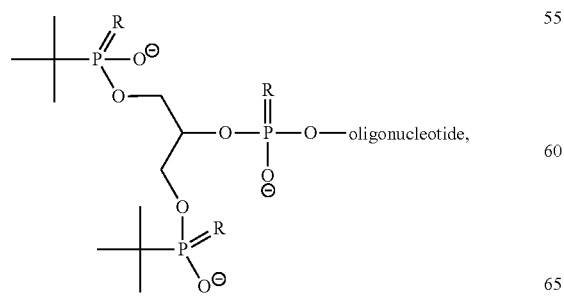

wherein R is O or S.

In certain embodiments, the oligomeric compound described herein, including but not limited to tunable REVERSIR™ compounds and siRNAs, comprises a monomer of structure:

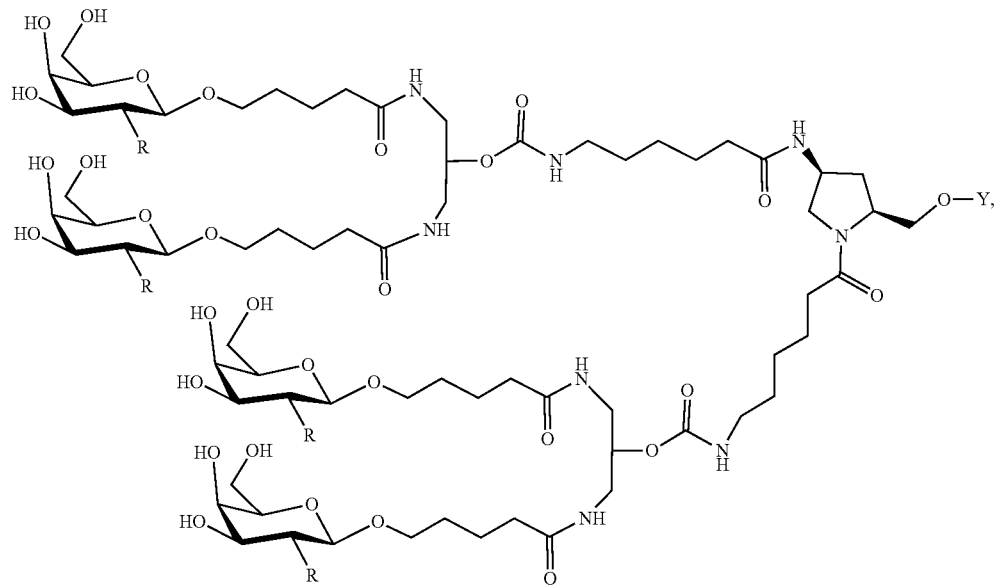

wherein R is OH or NHCOOH.

In certain embodiments, the oligomeric compound described herein, including but not limited to tunable REVERSIR™ compounds and siRNAs, comprises a monomer of structure:

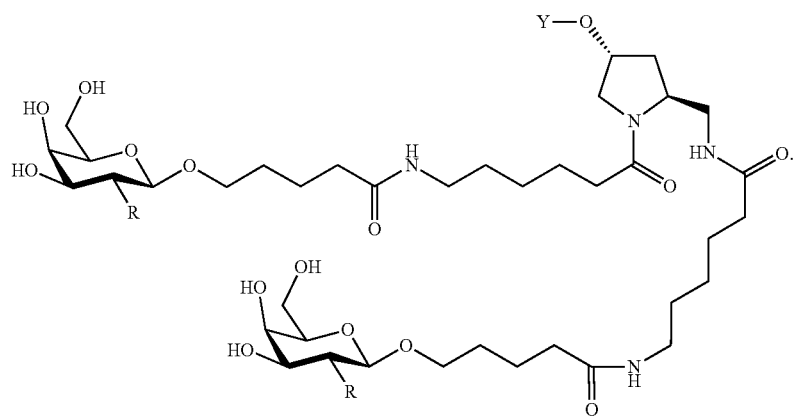

In certain embodiments, the oligomeric compound described herein, including but not limited to tunable REVERSIR™ compounds and siRNAs, comprises a monomer of structure:

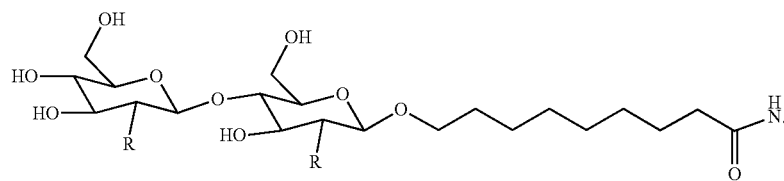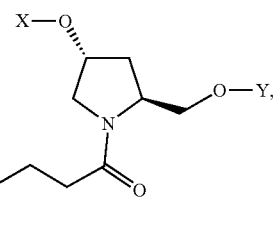

where in R is OH or NHCOOH.

In certain embodiments, the oligomeric compound described herein, including but not limited to tunable REVERSIR™ compounds and siRNAs, comprises a monomer of structure:

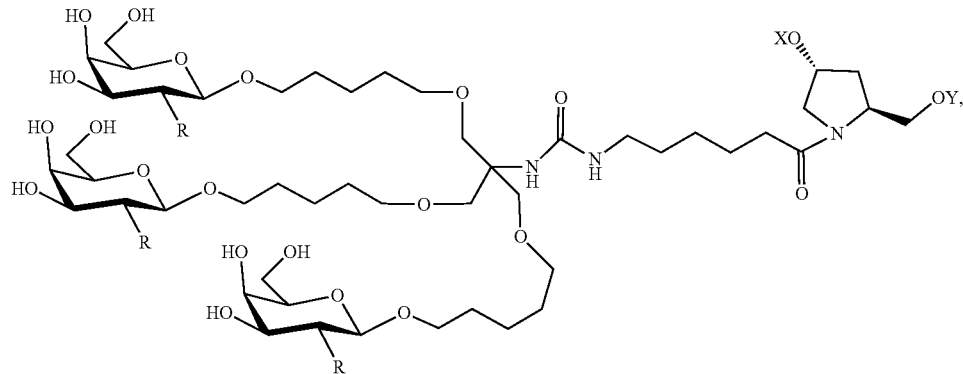

wherein R is OH or NHCOOH.

In certain embodiments, the oligomeric compound described herein, including but not limited to tunable REVERSIR™ compounds and siRNAs, comprises a monomer of structure:

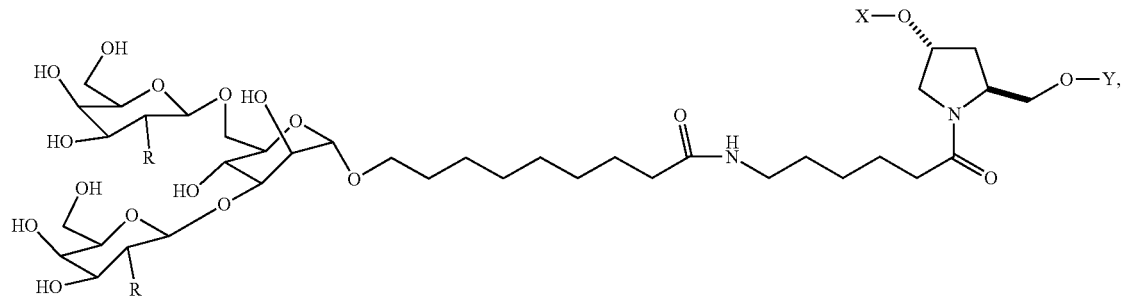

wherein R is OH or NHCOOH.

In certain embodiments, the oligomeric compound described herein, including but not limited to tunable REVERSIR™ compounds and siRNAs, comprises a monomer of structure:

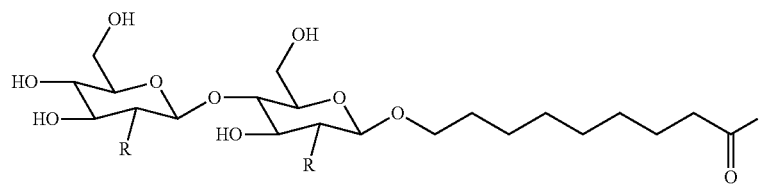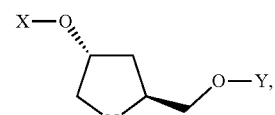

wherein R is OH or NHCOOH.

In certain embodiments, the oligomeric compound described herein, including but not limited to tunable REVERSIR™ compounds and siRNAs, comprises a monomer of structure:

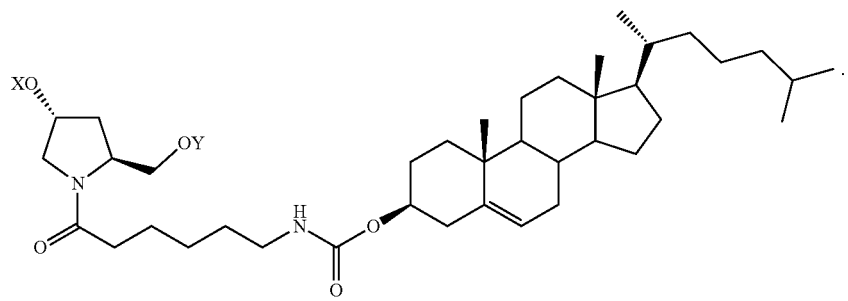

In the above described monomers, X and Y are each independently for each occurrence H, a protecting group, a phosphate group, a phosphodiester group, an activated phosphate group, an activated phosphite group, a phosphoramidite, a solid support, —P(Z')(Z")O-nucleotide, —P(Z') (Z")O-oligonucleotide, a lipid, a PEG, a steroid, a polymer, a nucleotide, a nucleotide, or an oligonucleotide; and Z' and Z" are each independently for each occurrence O or S.

In certain embodiments, the tunable REVERSIR™ compound is conjugated with a ligand of structure:

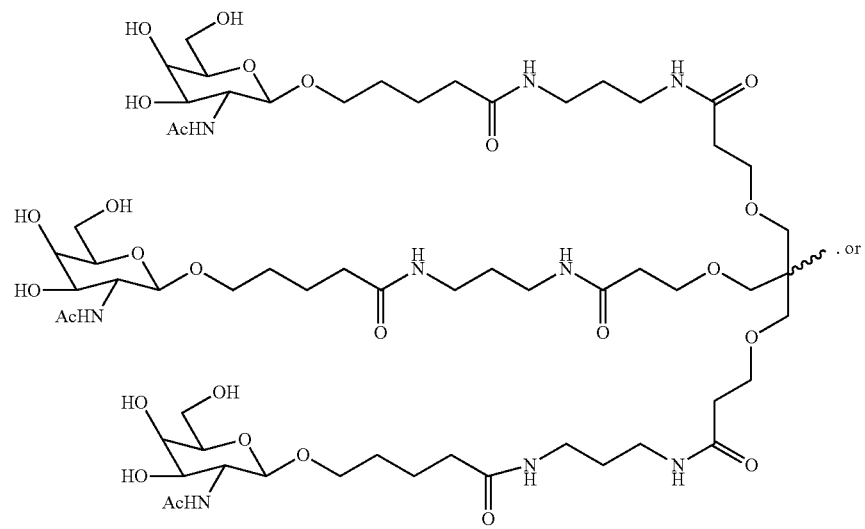

-continued
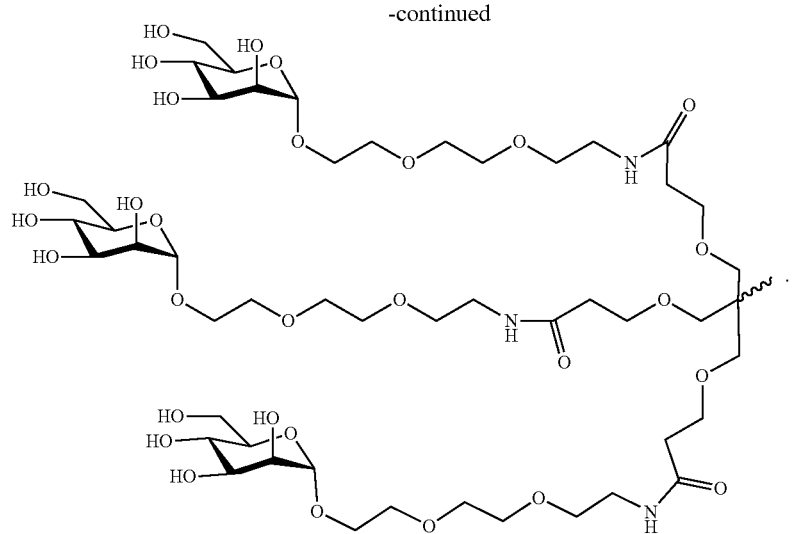
In certain embodiments, the conjugated siRNA comprises a ligand of structure:
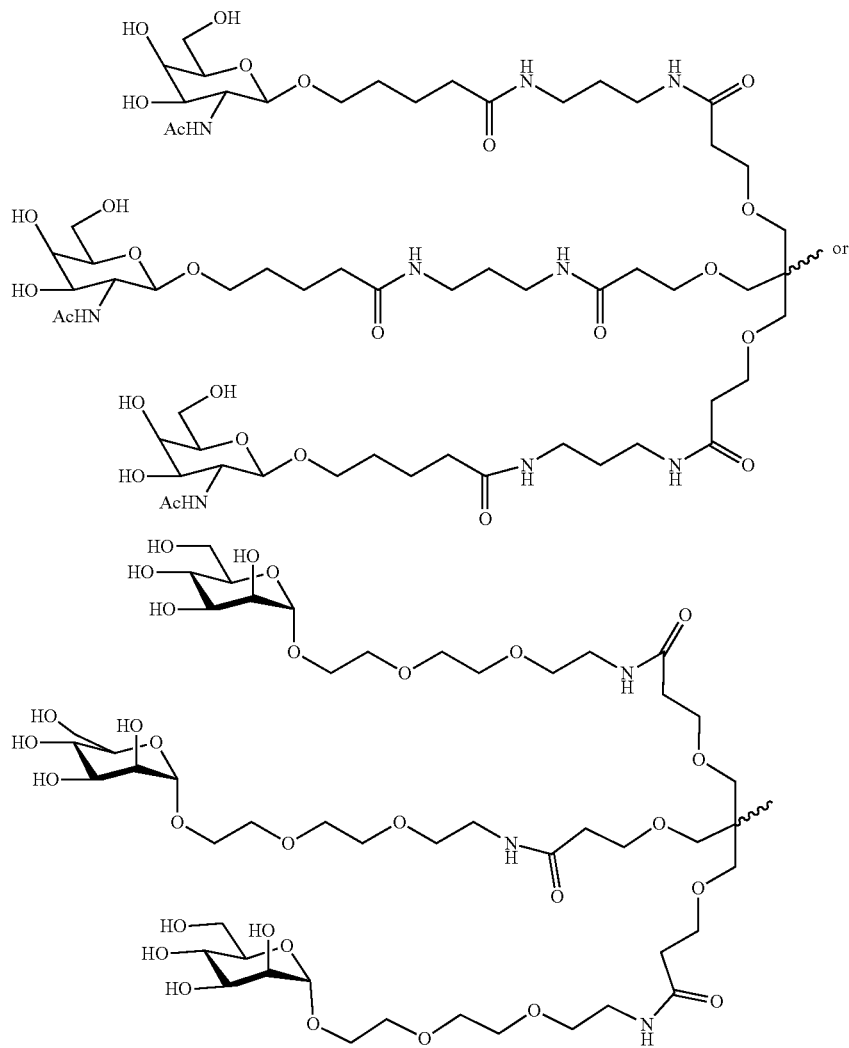

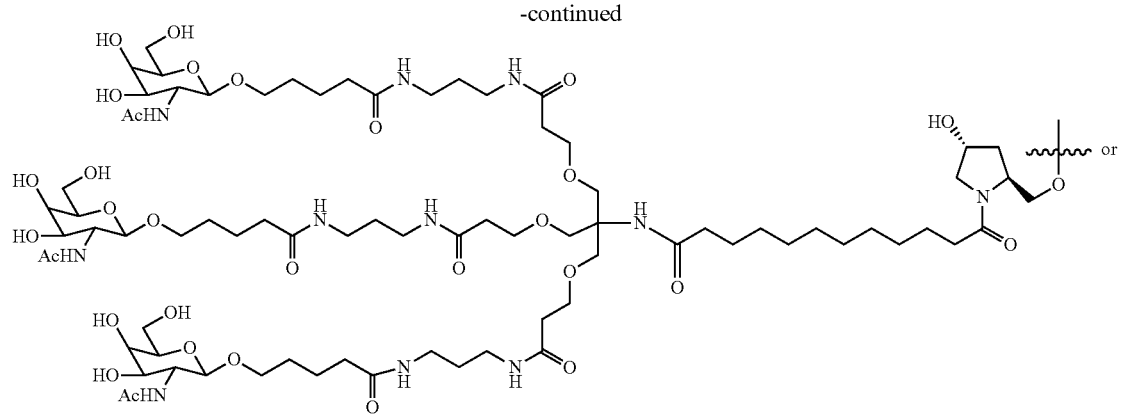
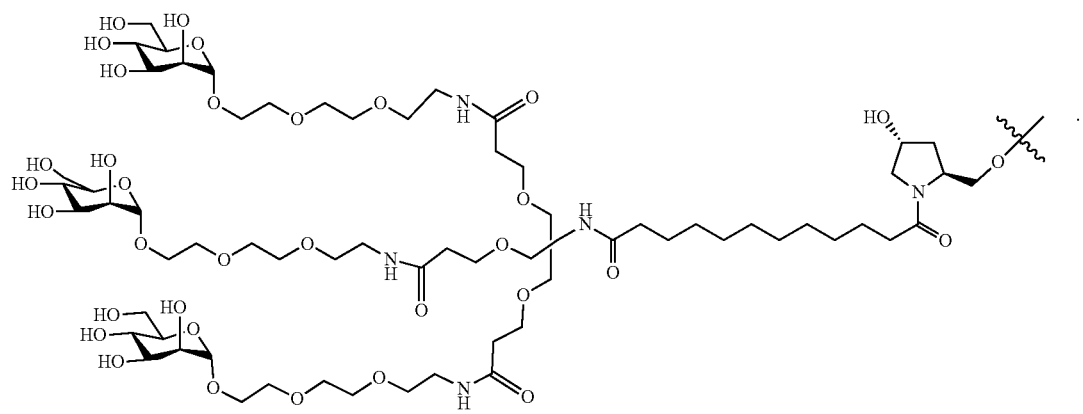
In certain embodiments, the tunable REVERSIR™ compound is conjugated with a ligand of structure:
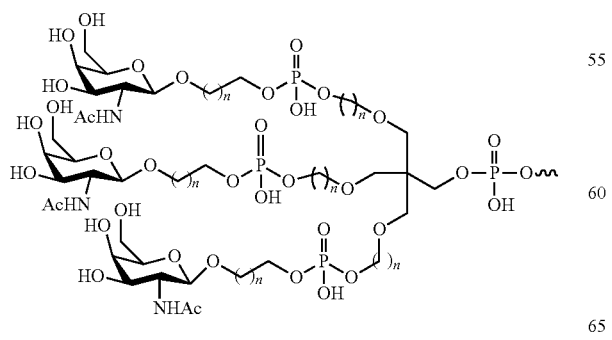
I
wherein each n is, independently, from 1 to 20.

In one example, the tunable REVERSIR™ compound is conjugated with a ligand of structure:

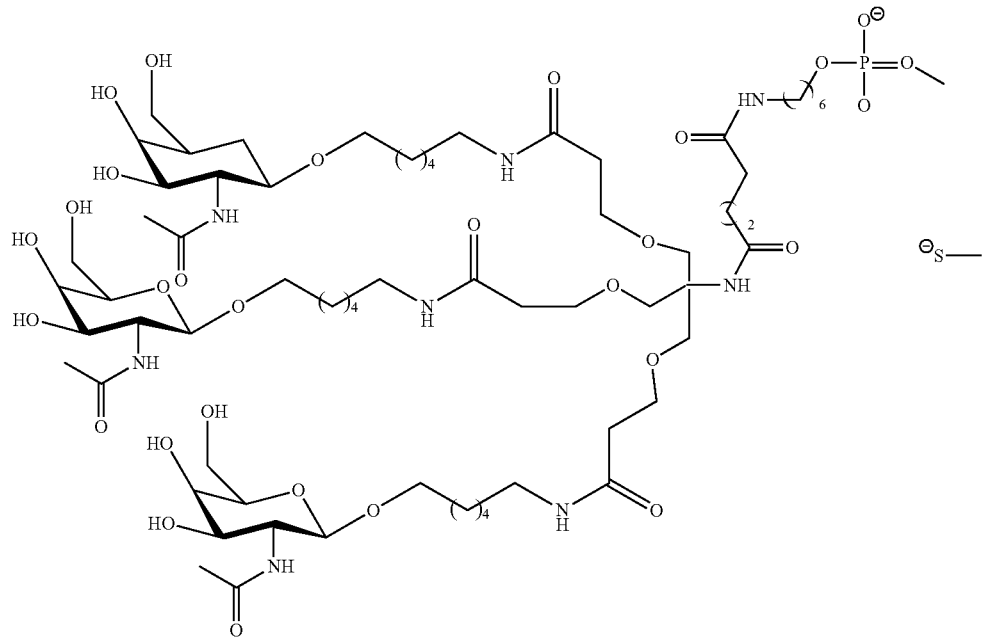

Synthesis of above described ligands and monomers is described, for example, in U.S. Pat. No. 8,106,022, content of which is incorporated herein by reference in its entirety.

Linking groups or bifunctional linking moieties such as those known in the art are amenable to the compounds provided herein. Linking groups are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted C2-C10 alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the ligand is conjugated with the oligomeric compound via a linker.

As used herein, the term "linker" means an organic moiety that connects two parts of a compound. Linkers typically comprise a direct bond or an atom such as oxygen or sulfur, a unit such as $NR^1$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In one embodiment, the linker is —[(P-Q"-R)$_q$—X—(P'-Q'''-R')$_{q'}$]$_{q''}$-T-, wherein: P, R, T, P', R' and T are each independently for each occurrence absent, CO, NH, O, S, OC(O), NHC(O), $CH_2$, $CH_2NH$, $CH_2O$; NHCH($R^a$)C(O), —C(O)—CH($R^a$)—NH—, CH=N—O,

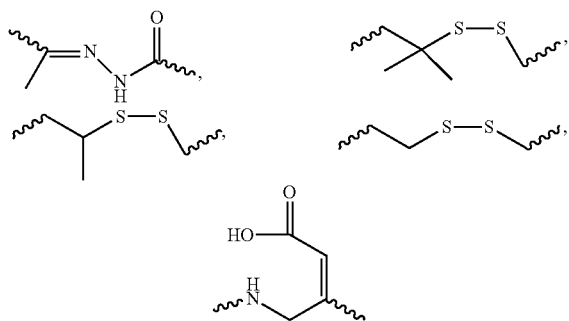

or heterocyclyl;
Q" and Q'" are each independently for each occurrence absent, —(CH$_2$)$_n$—, —C(R$^1$)(R$^2$)(CH$_2$)$_n$—, —(CH$_2$)$_n$C(R$^1$)(R$^2$)—, —(CH$_2$CH$_2$O)$_m$CH$_2$CH$_2$—, or —(CH$_2$CH$_2$O)$_m$CH$_2$CH$_2$NH—;
X is absent or a cleavable linking group;
R$^a$ is H or an amino acid side chain;
R$^1$ and R$^2$ are each independently for each occurrence H, CH$_3$, OH, SH or N(R$^N$)$_2$;
R$^N$ is independently for each occurrence H, methyl, ethyl, propyl, isopropyl, butyl or benzyl;
q, q' and q" are each independently for each occurrence 0-20 and wherein the repeating unit can be the same or different;
n is independently for each occurrence 1-20; and
m is independently for each occurrence 0-50.

In some embodiments, the linker comprises at least one cleavable linking group.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or C$_1$-C$_6$ alkyl and at least one R is C$_1$-C$_6$ alkyl such as CH$_3$ or CH$_2$CH$_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C1-C10 alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR A C(O)NHCHR B C(O)—, where R A and R B are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.-, 5.5, 5.0, or lower), or by agents such as enzymes that can act as a general acid.

In some embodiments, the linker is an oligonucleotide linker including, but not limited to, (N)$_n$; wherein N is independently a modified or unmodified nucleotide and n is 1-23. In some embodiments, n is 1-10, e.g., 1, 2, 3, 4, 5, 6, 7, 8, 9, or 10. In some embodiments, the oligonucleotide linker is selected from the group consisting of GNRA, (G)$_4$, (U)$_4$, and (dT)$_4$, wherein N is a modified or unmodified nucleotide and R is a modified or unmodified purine nucleotide. Some of the nucleotides in the linker can be involved in base-pair interactions with other nucleotides in the linker. It will be appreciated by one of skill in the art that any oligonucleotide chemical modifications or variations describe herein can be used in the oligonucleotide linker. In certain embodiments, the linker is dA.

Motifs

The present invention also includes oligomeric compounds which are chimeric oligomeric compounds. "Chimeric" oligomeric compounds or "chimeras," in the context of this invention, are oligomeric compounds which contain two or more chemically distinct regions, each made up of at least one monomer unit, i.e., a modified or unmodified nucleotide in the case of an oligonucleotide. Chimeric oligomeric compounds can be described as having a particular motif. In some embodiments, the motifs include, but are not limited to, an alternating motif, a gapped motif, a hemimer motif, a uniformly fully modified motif and a positionally modified motif. As used herein, the phrase "chemically distinct region" refers to an oligomeric region which is different from other regions by having a modification that is not present elsewhere in the oligomeric compound or by not having a modification that is present elsewhere in the oligomeric compound. An oligomeric compound can comprise two or more chemically distinct regions. As used herein, a region that comprises no modifications is also considered chemically distinct.

A chemically distinct region can be repeated within an oligomeric compound. Thus, a pattern of chemically distinct regions in an oligomeric compound can be realized such that a first chemically distinct region is followed by one or more second chemically distinct regions. This sequence of chemically distinct regions can be repeated one or more times. Preferably, the sequence is repeated more than one time. Both strands of a double-stranded oligomeric compound can comprise these sequences. Each chemically distinct region can actually comprise as little as a single monomers, e.g., nucleotides. In some embodiments, each chemically distinct region comprises 1, 2, 3, 4, 5, 6, 7, 8, 9, 10, 11, 12, 13, 14, 15, 16, 17 or 18 monomers, e.g., nucleotides.

In some embodiments, alternating nucleotides comprise the same modification, e.g. all the odd number nucleotides in a strand have the same modification and/or all the even number nucleotides in a strand have the similar modification to the first strand. In some embodiments, all the odd number nucleotides in an oligomeric compound have the same modification and all the even numbered nucleotides have a modification that is not present in the odd number nucleotides and vice versa.

When both strands of a double-stranded oligomeric compound comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other.

In some embodiments, the first strand has an alternating modification pattern wherein alternating nucleotides comprise a 2'-modification, e.g., 2'-O-Methyl modification. In some embodiments, the first strand comprises an alternating 2'-O-Methyl modification and the second strand comprises an alternating 2'-fluoro modification. In other embodiments, both strands of a double-stranded oligonucleotide comprise alternating 2'-O-methyl modifications.

When both strands of a double-stranded oligonucleotide comprise alternating 2'-O-methyl modifications, such 2'-modified nucleotides can be in complementary position in the duplex region. Alternatively, such 2'-modified nucleotides may not be in complementary positions in the duplex region.

In some embodiments, the oligonucleotide comprises two chemically distinct regions, wherein each region is 1,2, 3, 4, 5, 6, 7, 8,9 or 10 nucleotides in length.

In other embodiments, the oligomeric compound comprises three chemically distinct region. The middle region is about 5-15, (e.g., 5, 6, 7, 8, 9, 10, 11, 12, 13, 14 or 15) nucleotide in length and each flanking or wing region is independently 1-10 (e.g., 1, 2, 3, 4, 5, 6, 7, 8, 9 or 10) nucleotides in length. All three regions can have different modifications or the wing regions can be similarly modified to each other. In some embodiments, the wing regions are of equal length, e.g. 1, 2, 3, 4, 5, 6, 7, 8, 9 or 10 nucleotides long.

As used herein the term "alternating motif" refers to an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)nn-3' where A and B are monomelic subunits that have different sugar groups, each L is an internucleoside linking group, n is from about 4 to about 12 and nn is 0 or 1. This permits alternating oligomeric compounds from about 9 to about 26 monomer subunits in length. This length range is not meant to be limiting as longer and shorter oligomeric compounds are also amenable to the present invention. In one embodiment, one of A and B is a 2'-modified nucleoside as provided herein.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "type region" refers to a portion of an oligomeric compound wherein the nucleosides and internucleoside linkages within the region all comprise the same type of modifications; and the nucleosides and/or the internucleoside linkages of any neighboring portions include at least one different type of modification. As used herein the term "uniformly fully modified motif" refers to an oligonucleotide comprising a contiguous sequence of linked monomer subunits that each have the same type of sugar group. In one embodiment, the uniformly fully modified motif includes a contiguous sequence of nucleosides of the invention. In one embodiment, one or both of the 3' and 5'-ends of the contiguous sequence of the nucleosides provided herein, comprise terminal groups such as one or more unmodified nucleosides.

As used herein the term "hemimer motif" refers to an oligomeric compound having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomelic subunits) having uniform but different sugar groups and located on either the 3' or the 5' end of the oligomeric compound. In one embodiment, the hemimer motif comprises a contiguous sequence of from about 10 to about 28 monomer subunits of one type with from 1 to 5 or from 2 to about 5 monomer subunits of a second type located at one of the termini. In one embodiment, a hemimer is a contiguous sequence of from about 8 to about 20 (3-D-2'-deoxyribonucleosides having from 1-12 contiguous nucleosides of the invention located at one of the termini. In one embodiment, a hemimer is a contiguous sequence of from about 8 to about 20 (3-D-2'-deoxyribonucleosides having from 1-5 contiguous nucleosides of the invention located at one of the termini. In one embodiment, a hemimer is a contiguous sequence of from about 12 to about 18 β-D-2'-deoxyribo-nucleosides having from 1-3 contiguous nucleosides of the invention located at one of the termini. In one embodiment, a hemimer is a contiguous sequence of from about 10 to about 14 (3-D-2'-deoxyribonucleosides having from 1-3 contiguous nucleosides of the invention located at one of the termini.

As used herein the term "blockmer motif" refers to an oligonucleotide comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In one embodiment, blockmer oligonucleotides are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In one embodiment, each of the two or more regions have the same type of sugar group. In one embodiment, each of the two or more regions have a different type of sugar group. In one embodiment, positionally modified oligonucleotides are provided comprising a sequence of from 8 to 20 β-D-2'-deoxyribonucleosides that further includes two or three regions of from 2 to about 5 contiguous nucleosides of the invention. Positionally modified oligonucleotides are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In one embodiment, the external regions are small (each independently 1, 2, 3, 4 or about 5 monomer subunits) and the monomer subunits comprise non-naturally occurring sugar groups with the internal region comprising β-D-2'-deoxyribonucleosides. In one embodiment, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribo-nucleosides but can comprise non-naturally occurring sugar groups.

In one embodiment, the gapped oligomeric compounds comprise an internal region of 3-D-2'-deoxyribonucleosides with one of the external regions comprising nucleosides of the invention. In one embodiment, the gapped oligonucleotide comprise an internal region of β-D-2'-deoxyribo-nucleosides with both of the external regions comprising nucleosides of the invention. In one embodiment, the gapped oligonucleotide comprise an internal region of β-D-2'-deoxyribonucleosides with both of the external regions comprising nucleosides of the invention. In one embodiment, gapped oligonucleotides are provided herein wherein all of the monomer subunits comprise non-naturally occurring sugar groups. In one embodiment, gapped oligonucleotides are provided comprising one or two nucleosides of the invention at the 5'-end, two or three nucleosides of the invention at the 3'-end and an internal region of from 10 to 16 (3-D-2'-deoxyribonucleosides. In one embodiment, gapped oligonucleotides are provided comprising one nucleoside of the invention at the 5'-end, two nucleosides of the invention at the 3'-end and an internal region of from 10 to 16 (3-D-2'-deoxyribonucleosides. In one embodiment, gapped oligonucleotides are provided comprising two nucleosides of the invention at the 5'-end, two nucleosides of the invention at the 3'-end and an internal region of from 10 to 14 (3-D-2'-deoxyribonucleosides. In one embodiment, gapped oligonucleotides are provided that are from about 10 to about 21 monomer subunits in length. In one embodiment, gapped oligonucleotides are provided that are from about 12 to about 16 monomer subunits in length. In one embodiment, gapped oligonucleotides are provided that are from about 12 to about 14 monomer subunits in length.

In certain embodiments, the 5'-terminal monomer of an oligomeric compound of the invention comprises a phosphorous moiety at the 5'-end. In certain embodiments the 5'-terminal monomer comprises a 2'-modification. In certain such embodiments, the 2'-modification of the 5'-terminal monomer is a cationic modification. In certain embodiments, the 5'-terminal monomer comprises a 5'-modification. In certain embodiments, the 5'-terminal monomer comprises a 2'-modification and a 5'-modification. In certain embodiments, the 5'-terminal monomer is a 5'-stabilizing nucleoside. In certain embodiments, the modifications of the 5'-terminal monomer stabilize the 5'-phosphate. In certain embodiments, oligomeric compounds comprising modifications of the 5'-terminal monomer are resistant to exonucleases. In certain embodiments, oligomeric compounds comprising modifications of the 5'-terminal monomer have improved tunable REVERSIR™ properties. In certain such embodiments, oligomeric compound comprising modifications of the 5'-terminal monomer have improved association with a strand of the siRNA.

In certain embodiments, the 5'terminal monomer is attached to rest of the oligomeric compound a modified linkage. In certain such embodiments, the 5'terminal monomer is attached to rest of the oligomeric compound by a phosphorothioate linkage.

In certain embodiments, oligomeric compounds of the present invention comprise one or more regions of alternating modifications. In certain embodiments, oligomeric compounds comprise one or more regions of alternating nucleoside modifications. In certain embodiments, oligomeric compounds comprise one or more regions of alternating linkage modifications. In certain embodiments, oligomeric compounds comprise one or more regions of alternating nucleoside and linkage modifications.

In certain embodiments, oligomeric compounds of the present invention comprise one or more regions of alternating 2'-F modified nucleosides and 2'-OMe modified nucleosides. In certain such embodiments, such regions of alternating 2'F modified and 2' OMe modified nucleosides also comprise alternating linkages. In certain such embodiments, the linkages at the 3' end of the 2'-F modified nucleosides are phosphorothioate linkages. In certain such embodiments, the linkages at the 3'end of the 2'OMe nucleosides are phosphodiester linkages.

In certain embodiments, such alternating regions are: (2'-F)—(PS)-(2'-OMe)-(PO)

In certain embodiments, oligomeric compounds comprise 2, 3, 4, 5, 6, 7, 8, 9, 10, or 11 such alternating regions. Such regions may be contiguous or may be interrupted by differently modified nucleosides or linkages.

In certain embodiments, one or more alternating regions in an alternating motif include more than a single nucleoside of a type. For example, oligomeric compounds of the present invention may include one or more regions of any of the following nucleoside motifs:
ABA;
ABBA;
AABA;
AABBAA;
ABBABB;
AABAAB;
ABBABAABB;
ABABAA;
AABABAB;
ABABAA;
ABBAABBABABAA;
BABBAABBABABAA; or
ABABBAABBABABAA;
wherein A is a nucleoside of a first type and B is a nucleoside of a second type. In certain embodiments, A and B are each selected from 2'-F, 2'-OMe, LNA, DNA and MOE.

In certain embodiments, A is DNA. In certain embodiments B is DNA. In some embodiments, A is 4'-CH$_2$O-2'-LNA. In certain embodiments, B is 4'-CH$_2$O-2'-LNA. In certain embodiments, A is DNA and B is 4'-CH$_2$O-2'-LNA. In certain embodiments A is 4'-CH$_2$O-2'-LNA and B is DNA.

In certain embodiments, A is 2'-OMe. In certain embodiments B is 2'-OMe. In certain embodiments, A is 2'-OMe and B is 4'-CH$_2$O-2'-LNA. In certain embodiments A is 4'-CH$_2$O-2'-LNA and B is 2'-OMe. In certain embodiments, A is 2'-OMe and B is DNA. In certain embodiments A is DNA and B is 2'-OMe.

In certain embodiments, A is (S)-cEt. In some embodiments, B is (S)-cEt. In certain embodiments, A is 2'-OMe and B is (S)-cEt. In certain embodiments A is (S)-cEt and B is 2'-OMe. In certain embodiments, A is DNA and B is (S)-cEt. In certain embodiments A is (S)-cEt and B is DNA.

In certain embodiments, A is 2'-F. In certain embodiments B is 2'-F. In certain embodiments, A is 2'-F and B is 4'-CH$_2$O-2'-LNA. In certain embodiments A is 4'-CH$_2$O-2'-LNA and B is 2'-F. In certain embodiments, A is 2'-F and B is (S)-cEt. In certain embodiments A is (S)-cEt and B is 2'-F. In certain embodiments, A is 2'-F and B is DNA. In certain embodiments, A is DNA and B is 2'-F. In certain embodiments, A is 2'-OMe and B is 2'-F. In certain embodiments, A is DNA and B is 2'-OMe. In certain embodiments, A is 2'-OMe and B is DNA.

In certain embodiments, oligomeric compounds having such an alternating motif also comprise a 5' terminal nucleoside comprising a phosphate stabilizing modification. In certain embodiments, oligomeric compounds having such an alternating motif also comprise a 5' terminal nucleoside comprising a 2'-cationic modification. In certain embodiments, oligomeric compounds having such an alternating motif also comprise a 5' terminal modification.

Two-Two-Three Motifs

In certain embodiments, oligomeric compounds of the present invention comprise a region having a 2-2-3 motif. Such regions comprises the following motif:

5'-(E)$_w$-(A)$_2$-(B)$_x$-(A)$_2$-(C)$_y$-(A)$_3$-(D)$_z$ wherein: A is a first type of modified nucleoside;

B, C, D, and E are nucleosides that are differently modified than A, however, B, C, D, and E may have the same or different modifications as one another;

w and z are from 0 to 15;

x and y are from 1 to 15.

In certain embodiments, A is a 2'-OMe modified nucleoside. In certain embodiments, B, C, D, and E are all 2'-F modified nucleosides. In certain embodiments, A is a 2'-OMe modified nucleoside and B, C, D, and E are all 2'-F modified nucleosides.

In certain embodiments, the linkages of a 2-2-3 motif are all modified linkages. In certain embodiments, the linkages are all phosphorothioate linkages. In certain embodiments, the linkages at the 3'-end of each modification of the first type are phosphodiester.

In certain embodiments, Z is 0. In such embodiments, the region of three nucleosides of the first type are at the 3'-end of the oligonucleotide. In certain embodiments, such region is at the 3'-end of the oligomeric compound, with no additional groups attached to the 3' end of the region of three nucleosides of the first type. In certain embodiments, an oligomeric compound comprising an oligonucleotide where Z is 0, may comprise a terminal group attached to the 3'-terminal nucleoside. Such terminal groups may include additional nucleosides. Such additional nucleosides are typically non-hybridizing nucleosides.

In certain embodiments, Z is 1-3. In certain embodiments, Z is 2. In certain embodiments, the nucleosides of Z are 2'-MOE nucleosides. In certain embodiments, Z represents non-hybridizing nucleosides. To avoid confusion, it is noted that such non-hybridizing nucleosides might also be described as a 3'-terminal group with Z=0.

Combination Motifs

It is to be understood, that certain of the above described motifs and modifications can be combined. Since a motif may comprise only a few nucleosides, a particular oligomeric compound can comprise two or more motifs. By way of non-limiting example, in certain embodiments, oligomeric compounds can have two or more nucleotide motifs selected from LNAs, phosphorthioate linkages, 2'-OMe, conjugated ligand(s).

Oligomeric compounds having any of the various nucleoside motifs described herein, can have also have any linkage motif. For example, in the oligomeric compounds first 1, 2, 3, 4 or 5 at the 5'-end be modified intersugar linkages and first 4, 5, 6, 7 or 8 intersugar linkages at the 3'-end can be modified intersugar linkages. The central region of such modified oligomeric compound can have intersugar linkages based on the any of the other motifs described herein, for example, uniform, alternating, hemimer, gapmer, and the like. In some embodiments, the oligomeric compound comprise a phosphorothioate linkage between the first and second monomer at the 5'-terminus, alternating phosphorothioate/phosphodiester linkages in the central region and 6, 7, or 8 phosphorothioate linkages at the 3'-terminus.

It is to be noted that the lengths of the regions defined by a nucleoside motif and that of a linkage motif need not be the same.

In some embodiments, single-stranded oligomeric compounds or at least one strand of a double-stranded oligomeric compound, includes at least one of the following motifs:

(a) 5'-phosphorothioate or 5'-phosphorodithioate;
(b) a cationic modification of nucleotides 1 and 2 on the 5' terminal, wherein the cationic modification is at C5 position of pyrimidines and C2, C6, C8, exocyclic N2 or exocyclic N6 of purines;
(c) at least one G-clamp nucleotide in the first two terminal nucleotides at the 5' end and the other nucleotide having a cationic modification, wherein the cationic modification is at C5 position of pyrimidines or C2, C6, C8, exocyclic N2 or exocyclic N6 position of purines;
(d) at least one 2'-F modified nucleotide comprising a nucleobase base modification;
(e) at least one gem-2'-O-methyl/2'-F modified nucleotide comprising a nucleobase modification, preferably the methyl substituent is in the up configuration, e.g. in the arabinose configuration;
(f) a 5'-PuPu-3' dinucleotide at the 3' terminal wherein both nucleotides comprise a modified MOE at 2'-position as described in U.S. Patent Application Publication No. 20130130378, content of which is incorporated herein by reference in its entirety.
(g) a 5'-PuPu-3' dinucleotide at the 5' terminal wherein both nucleotides comprise a modified MOE at 2'-position as described in U.S. Patent Application Publication No. 20130130378;
(h) nucleotide at the 5' terminal having a modified MOE at 2'-position as described in U.S. Patent Application Publication No. 20130130378;
(i) nucleotide at the 5' terminal having a 3'-F modification;
(j) 5' terminal nucleotide comprising a 4'-substituent;
(k) 5' terminal nucleotide comprising a O4' modification;
(l) 3' terminal nucleotide comprising a 4'-substituent; and
(m) combinations thereof.

In some embodiments, both strands of a double-stranded oligomeric compound independently comprise at least one of the above described motifs. In some other embodiments, both strands of a double-stranded oligomeric compound comprise at least one at least one of the above described motifs, which motifs can be same or different or some combination of same and different.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of oligomeric compounds, such as those exemplified in the above tables, can be easily manipulated by lengthening or shortening one or more of the described regions, without disrupting the motif.

In some embodiments, oligomeric compound comprises two or more chemically distinct regions and has a structure as described in International Application No. PCT/US09/038433, filed Mar. 26, 2009, contents of which are herein incorporated in their entirety.

Synthesis, Purification and Analysis

Oligomerization of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds provided herein can be conveniently and routinely made through the well-known technique of solid phase synthesis. Equipment for such synthesis is sold by several vendors including, for example, Applied Biosystems (Foster City, Calif). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Methods of purification and analysis of oligomeric compounds are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

The oligomeric compounds of the invention can be prepared using solution-phase or solid-phase organic synthesis, or enzymatically by methods known in the art. Organic synthesis offers the advantage that the oligomeric strands comprising non-natural or modified nucleotides can be easily prepared. Any other means for such synthesis known in the art can additionally or alternatively be employed. It is also known to use similar techniques to prepare other oligomeric compounds, such as those comprising phosphorothioates, phosphorodithioates and alkylated derivatives of intersugar linkages. The double-stranded oligomeric compounds of the invention can be prepared using a two-step procedure. First, the individual strands of the double-stranded molecule are prepared separately. Then, the component strands are annealed.

Regardless of the method of synthesis, the oligomeric compounds can be prepared in a solution (e.g., an aqueous and/or organic solution) that is appropriate for formulation. For example, the oligomeric preparation can be precipitated and redissolved in pure double-distilled water, and lyophilized. The dried oligomeric compound can then be resuspended in a solution appropriate for the intended formulation process.

Teachings regarding the synthesis of particular modified oligomeric compounds can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having beta-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Compositions and Methods for Formulating Pharmaceutical Compositions

Oligomeric compounds can be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Oligomeric compounds, including siRNAs and/or tunable REVERSIR™ compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound and/or antidote compound and a pharmaceutically acceptable diluent. In certain embodiments, the pharmaceutically acceptable diluent is PBS.

Pharmaceutical compositions comprising oligomeric compounds encompass any pharmaceutically acceptable salts, esters, or salts of such esters. In certain embodiments, pharmaceutical compositions comprising oligomeric compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active oligomeric compound.

The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The oligomeric compounds can be delivered in a manner to target a particular tissue, such as the liver (e.g., the hepatocytes of the liver).

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention may be encapsulated within liposomes or may form complexes thereto, in particular to cationic liposomes. Alternatively, iRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference. There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contains a PEG moiety. Ilium et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534, 899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Liposome compositions can be prepared by a variety of methods that are known in the art. See e.g., U.S. Pat. Nos. 4,235,871; 4,737,323; 4,897,355 and 5,171,678; published International Applications WO 96/14057 and WO 96/37194; Felgner, P. L. et al., *Proc. Natl. Acad. Sci., USA* (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Lipid Particles

In some embodiments, the tunable REVERSIR™ can be fully encapsulated in a lipid formulation, e.g., a LNP, or other nucleic acid-lipid particle. The tunable REVERSIR™ encapsulated in the lipid formulation can be unconjugated or conjugated with a ligand (i.e., a conjugated tunable REVERSIR™)

As used herein, the term "LNP" refers to a stable nucleic acid-lipid particle. LNPs contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In some embodiments, the lipid to drug ratio (mass/mass ratio) (e.g., lipid to tunable REVERSIR™ ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.C1), 1,2-Dilinoleoyl-3-trimethylaminopropane chloride salt (DLin-TAP.C1), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxo1-5-amine (ALN100), (6Z,9Z,28Z,31Z)-heptatriaconta-6,9,28,31-tetraen-19-yl 4-(dimethyl amino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol, or a mixture thereof. The cationic lipid can comprise from about 20 mol % to about 50 mol % or about 40 mol % of the total lipid present in the particle.

In some embodiments, the compound 2,2-Dilinoleyl-4-dimethylaminoethyl-[1,3]-dioxolane can be used to prepare lipid-tunable REVERSIR™ nanoparticles. Synthesis of 2,2-Dilinoleyl-4-dimethylaminoethyl-[1,3]-dioxolane is described in International application no. PCT/US2009/061897, published as WO/2010/048536, which is herein incorporated by reference.

In some embodiments, the lipid-tunable REVERSIR™ particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 tunable REVERSIR™/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl (C16), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

Additional exemplary lipid-tunable REVERSIR™ formulations are described in Table 1 below.

TABLE 1

Exemplary lipid tunable REVERSIR formulations*

| Formulation | Ionizable/Cationic Lipid | cationic lipid/non-cationic lipid/cholesterol/PEG-lipid conjugate Lipid:tunable REVERSIR ratio |
|---|---|---|
| LNP_DLinDMA | 1,2-Dilinolenyloxy-N,N-dimethylaminopropane (DLinDMA) | DLinDMA/DPPC/Cholesterol/PEG-cDMA (57.1/7.1/34.4/1.4) lipid:tunable REVERSIR~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:tunable REVERSIR~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:tunable REVERSIR~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:tunable REVERSIR~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:tunable REVERSIR~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:tunable REVERSIR~11:1 |

TABLE 1-continued

Exemplary lipid tunable REVERSIR formulations*

| Formulation | Ionizable/Cationic Lipid | cationic lipid/non-cationic lipid/cholesterol/PEG-lipid conjugate Lipid:tunable REVERSIR ratio |
|---|---|---|
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:tunable REVERSIR 10:1 |
| LNP10 | (3aR,5s,6aS)-N,N-dimethyl-2,2-di((9Z, 12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:tunable REVERSIR 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:tunable REVERSIR 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200> | Tech G1/DSPC/Cholesterol/PEG-DMG 50/10/38.5/1.5 Lipid:tunable REVERSIR 10:1 |
| LNP13 | XTC | XTC/DSPC/Chol/PEG-DMG 50/10/38.5/1.5 Lipid:tunable REVERSIR: 33:1 |
| LNP14 | MC3 | MC3/DSPC/Chol/PEG-DMG 40/15/40/5 Lipid:tunable REVERSIR: 11:1 |
| LNP15 | MC3 | MC3/DSPC/Chol/PEG-DSG/GalNAc-PEG-DSG 50/10/35/4.5/0.5 Lipid:tunable REVERSIR: 11:1 |
| LNP16 | MC3 | MC3/DSPC/Chol/PEG-DMG 50/10/38.5/1.5 Lipid:tunable REVERSIR: 7:1 |
| LNP17 | MC3 | MC3/DSPC/Chol/PEG-DSG 50/10/38.5/1.5 Lipid:tunable REVERSIR: 10:1 |
| LNP18 | MC3 | MC3/DSPC/Chol/PEG-DMG 50/10/38.5/1.5 Lipid:tunable REVERSIR: 12:1 |
| LNP19 | MC3 | MC3/DSPC/Chol/PEG-DMG 50/10/35/5 Lipid:tunable REVERSIR: 8:1 |
| LNP20 | MC3 | MC3/DSPC/Chol/PEG-DPG 50/10/38.5/1.5 Lipid:tunable REVERSIR: 10:1 |
| LNP21 | C12-200 | C12-200/DSPC/Chol/PEG-DSG 50/10/38.5/1.5 Lipid:tunable REVERSIR: 7:1 |
| LNP22 | XTC | XTC/DSPC/Chol/PEG-DSG 50/10/38.5/1.5 Lipid:tunable REVERSIR: 10:1 |
| LNPX | (13Z,16Z)-N,N-dimethyl-3-nonyldocosa-13,16-dien-1-amine | (13Z,16Z)-N,N-dimethyl-3-nonyldocosa-13,16-dien-1-amine/DSPC/Chol/PEG-DSG 50/10/38.5/1.5 Lipid:tunable REVERSIR: 10:1 |
| LNPY | Biodegradable lipid | Biodegradable lipid/DSPC/Chol/PEG-DSG 50/10/38.5/1.5 Lipid:tunable REVERSIR: 10:1 |

*The tunable REVERSIR can be an unconjugated or conjugated with a ligand (i.e. conjugated tunable REVERSIR).

Abbreviations in Table 1 include the following: DSPC: distearoylphosphatidylcholine; DPPC: dipalmitoylphosphatidylcholine; PEG-DMG: PEG-didimyristoyl glycerol (C14-PEG, or PEG-C14) (PEG with avg mol wt of 2000); PEG-DSG: PEG-distyryl glycerol (C18-PEG, or PEG-C18) (PEG with avg mol wt of 2000); PEG-cDMA: PEG-carbamoyl-1,2-dimyristyloxypropylamine (PEG with avg mol wt of 2000).

DLinDMA (1,2-Dilinolenyloxy-N,N-dimethylaminopropane) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference.

Biodegradable lipid comprising formulations are described, e.g., PCT Publications No. WO2011/153493, filed Jun. 3, 2011 and WO/2013/086354, filed Dec. 7, 2012, the entire contents of which are hereby incorporated by reference.

(13Z,16Z)—N,N-dimethyl-3-nonyldocosa-13,16-dien-1-amine comprising formulations are described, e.g., in PCT Publications No. WO/2012/040184, filed Sep. 20, 2011, the entire contents of which are hereby incorporated by reference.

The oligomeric compounds of the invention can be prepared and formulated as micelles. As used herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

In some embodiments, the formulations comprises micelles formed from an oligonucleotide of the invention and at least one amphiphilic carrier, in which the micelles have an average diameter of less than about 100 nm, preferably. More preferred embodiments provide micelles having an average diameter less than about 50 nm, and even more preferred embodiments provide micelles having an average diameter less than about 30 nm, or even less than about 20 nm.

Micelle formulations can be prepared by mixing an aqueous solution of the oligonucleotide composition, an alkali metal $C_8$ to $C_{22}$ alkyl sulphate, and an amphiphilic carrier. The amphiphilic carrier can be added at the same time or after addition of the alkali metal alkyl sulphate. Micelles will form with substantially any kind of mixing of the ingredients but vigorous mixing in order to provide smaller size micelles.

The oligomeric compounds of the present invention can be prepared and formulated as emulsions. As used herein, "emulsion" is a heterogenous system of one liquid dispersed in another in the form of droplets.

Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials is also included in emulsion formulations and contributes to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In some embodiments, the compositions are formulated as microemulsions. As used herein, "microemulsion" refers to a system of water, oil and amphiphile which is a single optically isotropic and thermodynamically stable liquid solution. Microemuslions also include thermodynamically stable, isotropically clear dispersions of two immiscible liquids that are stabilized by interfacial films of surface-active molecules.

A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, contents of which are herein incorporated by reference in their entirety.

The oligomeric compounds of the present invention can be prepared and formulated as lipid particles, e.g., formulated lipid particles (FLiPs) comprising (a) an oligonucleotide of the invention, where said oligonucleotide has been conjugated to a lipophile and (b) at least one lipid component, for example an emulsion, liposome, isolated lipoprotein, reconstituted lipoprotein or phospholipid, to which the conjugated oligonucleotide has been aggregated, admixed or associated. The stoichiometry of oligonucleotide to the lipid component can be 1:1. Alternatively the stoichiometry can be 1:many, many:1 or many:many, where many is two or more.

The FLiP can comprise triacylglycerols, phospholipids, glycerol and one or several lipid-binding proteins aggregated, admixed or associated via a lipophilic linker molecule with an oligonucleotide. Surprisingly, it has been found that due to said one or several lipid-binding proteins in combination with the above mentioned lipids, the FLiPs show affinity to liver, gut, kidney, steroidogenic organs, heart, lung and/or muscle tissue. These FLiPs can therefore serve as carrier for oligonucleotides to these tissues. For example, lipid-conjugated oligonucleotides, e.g., cholesterol-conjugated oligonucleotides, bind to HDL and LDL lipoprotein particles which mediate cellular uptake upon binding to their respective receptors thus directing oligonucleotide delivery into liver, gut, kidney and steroidogenic organs, see Wolfrum et al. Nature Biotech. (2007), 25:1145-1157.

The FLiP can be a lipid particle comprising 15-25% triacylglycerol, about 0.5-2% phospholipids and 1-3% glycerol, and one or several lipid-binding proteins. FLiPs can be a lipid particle having about 15-25% triacylglycerol, about 1-2% phospholipids, about 2-3% glycerol, and one or several lipid-binding proteins. In some embodiments, the lipid particle comprises about 20% triacylglycerol, about 1.2% phospholipids and about 2.25% glycerol, and one or several lipid-binding proteins.

Another suitable lipid component for FLiPs is lipoproteins, for example isolated lipoproteins or more preferably reconstituted lipoprotieins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins). Methods of producing reconstituted lipoproteins are known in the art, for example see A. Jones, Experimental Lung Res. 6, 255-270 (1984), U.S. Pat. Nos. 4,643,988 and 5,128,318, PCT publication WO87/02062, Canadian Pat. No. 2,138, 925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

One preferred lipid component for FLiP is Intralipid. Intralipid® is a brand name for the first safe fat emulsion for human use. Intralipid® 20% (a 20% intravenous fat emulsion) is made up of 20% soybean oil, 1.2% egg yolk phospholipids, 2.25% glycerin, and water for injection. It is further within the present invention that other suitable oils, such as safflower oil, can serve to produce the lipid component of the FLiP.

FLiP can range in size from about 20-50 nm or about 30-50 nm, e.g., about 35 nm or about 40 nm. In some embodiments, the FLiP has a particle size of at least about 100 nm. FLiPs can alternatively be between about 100-150 nm, e.g., about 110 nm, about 120 nm, about 130 nm, or about 140 nm, whether characterized as liposome- or emulsion-based. Multiple FLiPs can also be aggregated and delivered together, therefore the size can be larger than 100 nm.

The process for making the lipid particles comprises the steps of: (a) mixing a lipid components with one or several lipophile (e.g. cholesterol) conjugated oligonucleotides that can be chemically modified; and (b) fractionating this mixture. In some embodiments, the process comprises the additional step of selecting the fraction with particle size of 30-50 nm, preferably of about 40 nm in size.

Some exemplary lipid particle formulations amenable to the invention are described in U.S. patent application Ser. No. 12/412,206, filed Mar. 26, 2009, content of which is herein incorporated by reference in its entirety.

In some embodiments, the oligomeric compounds can be formulated in yeast cell wall particles ("YCWP"). A yeast cell wall particle comprises an extracted yeast cell wall exterior and a core, the core comprising a payload (e.g., oligonucleotides). Exterior of the particle comprises yeast glucans (e.g. beta glucans, beta-1,3-glucans, beta-1,6-glucans), yeast mannans, or combinations thereof. Yeast cell wall particles are typically spherical particles about 1-4 µm in diameter.

Preparation of yeast cell wall particles is known in the art, and is described, for example in U.S. Pat. Nos. 4,992,540; 5,082,936; 5,028,703; 5,032,401; 5,322,841; 5,401,727; 5,504,079; 5,607,677; 5,741,495; 5,830,463; 5,968,811; 6,444,448; and 6,476,003, U.S. Pat. App. Pub. Nos. 2003/0216346 and 2004/0014715, and Int. App. Pub. No. WO 2002/12348, contents of which are herein incorporated by reference in their entirety. Applications of yeast cell like particles for drug delivery are described, for example in U.S. Pat. Nos. 5,032,401; 5,607,677; 5,741,495; and 5,830,463, and U.S. Pat. Pub Nos. 2005/0281781 and 2008/0044438, contents of which are herein incorporated by reference in their entirety. U.S. Pat. App. Pub. No. 2009/0226528, contents of which are herein incorporated by reference, describes formulation of nucleic acids with yeast cell wall particles for delivery of oligonucleotide to cells.

Exemplary formulations for oligomeric compounds are described in U.S. Pat. Nos. 4,897,355; 4,394,448; 4,235, 871; 4,231,877; 4,224,179; 4,753,788; 4,673,567; 4,247, 411; 4,814,270; 5,567,434; 5,552,157; 5,565,213; 5,738, 868; 5,795,587; 5,922,859; 6,077,663; 7,906,484; and 8,642,076; PCT Publication No. WO2009/132131 and U.S. Pat. Pub. Nos. 2006/0240093, 2007/0135372, 2011/0117125, 2009/0291131, 2012/0316220, 2009/0163705 and 2013/0129785, contents of all of which is herein incorporated by reference in its entirety. Behr (1994) Bioconjugate Chem. 5:382-389, and Lewis et al. (1996) PNAS 93:3176-3181), also describe formulations for oligonucleotides that are amenable to the invention, contents of which are herein incorporated by reference in their entirety.

siRNA

As used herein, the term "siRNA" refers to an agent that mediates the targeted cleavage of an RNA transcript. These agents associate with a cytoplasmic multi-protein complex known as RNAi-induced silencing complex (RISC). Agents that are effective in inducing RNA interference are also referred to as siRNA, RNAi agent, or iRNA agent, herein. As used herein, the term siRNA includes microRNAs and pre-microRNAs.

As used herein, the term "siRNA" refers to an agent that mediates the targeted cleavage of an RNA transcript. These agents associate with a cytoplasmic multi-protein complex known as RNAi-induced silencing complex (RISC). Agents that are effective in inducing RNA interference are also referred to as siRNA, dsRNA, RNAi agent, or iRNA agent herein.

As used herein, the terms "siRNA activity" and "RNAi activity" refer to gene silencing by an siRNA.

As used herein, "gene silencing" by a RNA interference molecule refers to a decrease in the mRNA level in a cell for a target gene by at least about 5%, at least about 10%, at least about 20%, at least about 30%, at least about 40%, at least about 50%, at least about 60%, at least about 70%, at least about 80%, at least about 90%, at least about 95%, at least about 99% up to and including 100%, and any integer in between of the mRNA level found in the cell without the presence of the miRNA or RNA interference molecule. In one preferred embodiment, the mRNA levels are decreased by at least about 70%, at least about 80%, at least about 90%, at least about 95%, at least about 99%, up to and including 100% and any integer in between 5% and 100%.

As used herein the term "modulate gene expression" means that expression of the gene, or level of RNA molecule or equivalent RNA molecules encoding one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

As used herein, gene expression modulation happens when the expression of the gene, or level of RNA molecule or equivalent RNA molecules encoding one or more proteins or protein subunits is at least 5%, 10%, 20%, 30%, 40%, 50%, 60%, 70%, 80%, 90%, 100%, 2-fold, 3-fold, 4-fold, 5-fold or more different from that observed in the absence of the siRNA, e.g., RNAi agent. The % and/or fold difference can be calculated relative to the control or the non-control, for example, $$\% \text{ difference} = \frac{[\text{expression with siRNA} - \text{expression without siRNA}]}{\text{expression without siRNA}}$$

or $$\% \text{ difference} = \frac{[\text{expression with siRNA} - \text{expression without siRNA}]}{\text{expression without siRNA}}$$

As used herein, the term "inhibit", "down-regulate", or "reduce" in relation to gene expression, means that the expression of the gene, or level of RNA molecules or equivalent RNA molecules encoding one or more proteins or protein subunits, or activity of one or more proteins or protein subunits, is reduced below that observed in the absence of modulator. The gene expression is down-regulated when expression of the gene, or level of RNA molecules or equivalent RNA molecules encoding one or more proteins or protein subunits, or activity of one or more proteins or protein subunits, is reduced at least 10% lower relative to a corresponding non-modulated control, and preferably at least 10%, 20%, 30%, 40%, 50%, 60%, 70%, 80%, 90%, 95%, 98%, 99% or most preferably, 100% (i.e., no gene expression).

As used herein, the term "increase" or "up-regulate" in relation to gene expression, means that the expression of the gene, or level of RNA molecules or equivalent RNA molecules encoding one or more proteins or protein subunits, or activity of one or more proteins or protein subunits, is increased above that observed in the absence of modulator. The gene expression is up-regulated when expression of the gene, or level of RNA molecules or equivalent RNA molecules encoding one or more proteins or protein subunits, or activity of one or more proteins or protein subunits, is increased at least 10% relative to a corresponding non-modulated control, and preferably at least 10%, 20%, 30%, 40%, 50%, 60%, 70%, 80%, 90%, 95%, 98%, 100%, 1.1-fold, 1.25-fold, 1.5-fold, 1.75-fold, 2-fold, 3-fold, 4-fold, 5-fold, 10-fold, 50-fold, 100-fold or more.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "reduced" or "reduce" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The skilled person is well aware that double-stranded oligonucleotides comprising a duplex structure of between 20 and 23, but specifically 21, base pairs have been hailed as particularly effective in inducing RNA interference (Elbashir et al., EMBO 2001, 20:6877-6888). However, others have found that shorter or longer double-stranded oligonucleotides can be effective as well.

The double-stranded oligonucleotides comprise two oligonucleotide strands that are sufficiently complementary to hybridize to form a duplex structure. Generally, the duplex structure is between 15 and 30, more generally between 18 and 25, yet more generally between 19 and 24, and most generally between 19 and 21 base pairs in length. In some embodiments, longer double-stranded oligonucleotides of between 25 and 30 base pairs in length are preferred. In some embodiments, shorter double-stranded oligonucleotides of between 10 and 15 base pairs in length are preferred. In another embodiment, the double-stranded oligonucleotide is at least 21 nucleotides long.

In some embodiments, the double-stranded oligonucleotide comprises a sense strand and an antisense strand, wherein the antisense RNA strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 21 nucleotides in length.

The phrase "antisense strand" as used herein, refers to an oligomeric compound that is substantially or 100% complementary to a target sequence of interest. The phrase "antisense strand" includes the antisense region of both oligomeric compounds that are formed from two separate strands, as well as unimolecular oligomeric compounds that are capable of forming hairpin or dumbbell type structures. The terms "antisense strand" and "guide strand" are used interchangeably herein.

The phrase "sense strand" refers to an oligomeric compound that has the same nucleotide sequence, in whole or in part, as a target sequence such as a messenger RNA or a sequence of DNA. The terms "sense strand" and "passenger strand" are used interchangeably herein.

By "specifically hybridizable" and "complementary" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol. LII pp.* 123-133; Frier et al., 1986, *Proc. Nat. Acad. Sci. USA* 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9,10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleotide units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

The term "off-target" and the phrase "off-target effects" refer to any instance in which an siRNA against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of an siRNA.

In some embodiments, the double-stranded region of a double-stranded oligomeric compound is equal to or at least, 10, 11, 12, 13, 14, 15, 16, 17, 18, 19, 20, 21, 22, 23, 23, 24, 25, 26, 27, 28, 29, or 30 nucleotide pairs in length.

In some embodiments, the antisense strand of a double-stranded oligomeric compound is equal to or at least 14, 15, 16, 17, 18, 19, 20, 21, 22, 23, 23, 24, 25, 26, 27, 28, 29, or 30 nucleotides in length.

In some embodiments, the sense strand of a double-stranded oligomeric compound is equal to or at least 10, 11, 12, 13, 14, 15, 16, 17, 18, 19, 20, 21, 22, 23, 23, 24, 25, 26, 27, 28, 29, or 30 nucleotides in length.

In some embodiments, one strand has at least one stretch of 1-5 single-stranded nucleotides in the double-stranded region. By "stretch of single-stranded nucleotides in the double-stranded region" is meant that there is present at least one nucleotide base pair at both ends of the single-stranded stretch. In some embodiments, both strands have at least one stretch of 1-5 (e.g., 1, 2, 3, 4, or 5) single-stranded nucleotides in the double stranded region. When both strands have a stretch of 1-5 (e.g., 1, 2, 3, 4, or 5) single-stranded nucleotides in the double stranded region, such single-stranded nucleotides can be opposite to each other (e.g., a stretch of mismatches) or they can be located such that the second strand has no single-stranded nucleotides opposite to the single-stranded oligonucleotides of the first strand and vice versa (e.g., a single-stranded loop). In some embodiments, the single-stranded nucleotides are present within 8 nucleotides from either end, for example 8, 7, 6, 5, 4, 3, or 2 nucleotide from either the 5' or 3' end of the region of complementarity between the two strands.

In some embodiments, each strand of the double-stranded oligonucleotide has a ZXY structure, such as is described in PCT Publication No. 2004080406, content of which is hereby incorporated in its entireties.

In certain embodiment, the two strands of double-stranded oligomeric compound can be linked together. The two strands can be linked to each other at both ends, or at one end only. By linking at one end is meant that 5'-end of first strand is linked to the 3'-end of the second strand or 3'-end of first strand is linked to 5'-end of the second strand. When the two strands are linked to each other at both ends, 5'-end of first strand is linked to 3'-end of second strand and 3'-end of first strand is linked to 5'-end of second strand. The two strands can be linked together by an oligonucleotide linker including, but not limited to, $(N)_n$; wherein N is independently a modified or unmodified nucleotide and n is 3-23. In some embodiments, n is 3-10, e.g., 3, 4, 5, 6, 7, 8, 9, or 10. In some embodiments, the oligonucleotide linker is selected from the group consisting of GNRA, (G)4, (U)4, and (dT)4, wherein N is a modified or unmodified nucleotide and R is a modified or unmodified purine nucleotide. Some of the nucleotides in the linker can be involved in base-pair interactions with other nucleotides in the linker. The two strands can also be linked together by a non-nucleosidic linker, e.g. a linker described herein. It will be appreciated by one of skill in the art that any oligonucleotide chemical modifications or variations describe herein can be used in the oligonucleotide linker.

Hairpin and dumbbell type oligomeric compounds will have a duplex region equal to or at least 14, 15, 15, 16, 17, 18, 19, 29, 21, 22, 23, 24, or 25 nucleotide pairs. The duplex region can be equal to or less than 200, 100, or 50, in length. In some embodiments, ranges for the duplex region are 15-30, 17 to 23, 19 to 23, and 19 to 21 nucleotides pairs in length.

The hairpin oligomeric compounds can have a single strand overhang or terminal unpaired region, in some embodiments at the 3', and in some embodiments on the antisense side of the hairpin. In some embodiments, the overhangs are 1-4, more generally 2-3 nucleotides in length. The hairpin oligomeric compounds that can induce RNA interference are also referred to as "shRNA" herein.

In certain embodiments, two oligomeric strands specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA duplex.

Modulation of Target Expression

In certain embodiments, a target nucleic acid is a mRNA. In certain such embodiments, siRNAs are designed to modulate that target mRNA or its expression. In certain embodiments, designing an antisense compound to a target nucleic acid molecule can be a multistep process. Typically the process begins with the identification of a target protein, the activity of which is to be modulated, and then identifying the nucleic acid the expression of which yields the target protein. In certain embodiments, designing of an antisense compound results in an antisense compound that is hybridizable to the targeted nucleic acid molecule. In certain embodiments, the antisense compound is an antisense oligonucleotide or antisense oligonucleoside. In certain embodiments, an antisense compound and a target nucleic acid are complementary to one another. In certain such embodiments, an antisense compound is perfectly complementary to a target nucleic acid. In certain embodiments, an antisense compound includes one mismatch. In certain embodiments, an antisense compound includes two mismatches. In certain embodiments, an antisense compound includes three or more mismatches.

Modulation of expression of a target nucleic acid can be achieved through alteration of any number of nucleic acid functions. In certain embodiments, the functions of RNA to be modulated include, but are not limited to, translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. Thus, in one embodiment modulation of expression can mean increase or decrease in target RNA or protein levels. In another embodiment modulation of expression can mean an increase or decrease of one or more RNA splice products, or a change in the ratio of two or more splice products.

In certain embodiments, the siRNA is a conjugated siRNA. As used herein, the term "conjugated siRNA" refers to an RNAi agent that is conjugated with a ligand. For Example, an RNAi agent conjugated with a ligand described herein.

In some other embodiments, the siRNA is an unconjugated siRNA. As used herein, the term "unconjugated siRNA" refers to an RNAi agent that is not conjugated with a ligand, e.g., a ligand described herein.

In one aspect, the invention relates to a double-stranded RNA (dsRNA) agent, i.e., siRNA, for inhibiting the expression of a target gene. The dsRNA agent comprises a sense strand and an antisense strand, each strand having 14 to 40 nucleotides. The dsRNA agent is represented by formula (I):

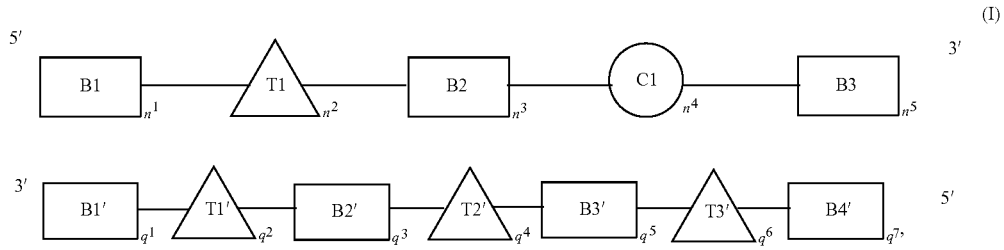

(I)

In formula (I), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In one embodiment, B1, B2, B3, B1', B2', B3', and B4' each contain 2'-OMe modifications.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In one embodiment, C1 has thermally destabilizing modification selected from the group consisting of: i) mismatch with the opposing nucleotide in the antisense strand; ii) abasic modification selected from the group consisting of:

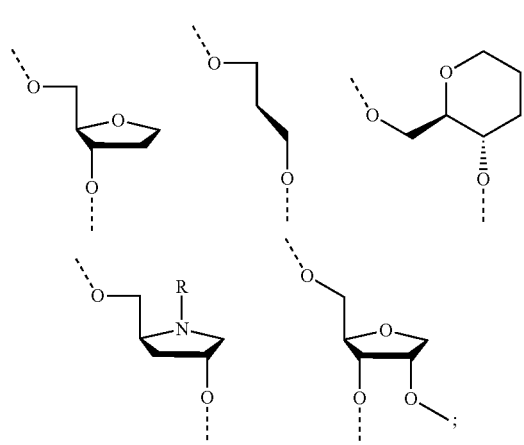

and iii) sugar modification selected from the group consisting of:

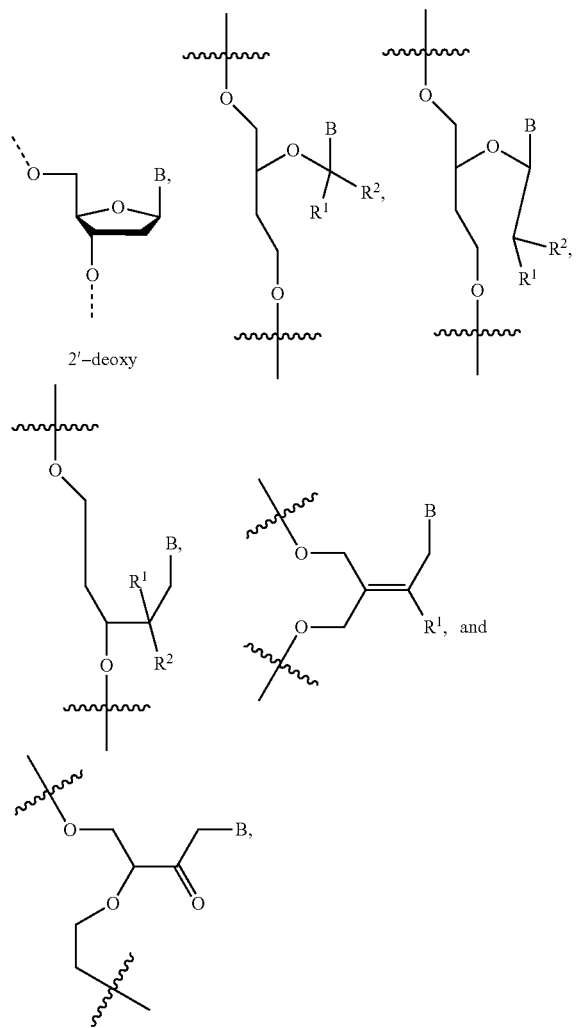

wherein B is a modified or unmodified nucleobase, $R^1$ and $R^2$ independently are H, halogen, OR, or alkyl; and $R^3$ is H, alkyl, cycloalkyl, aryl, aralkyl, heteroaryl or sugar. In one embodiment, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

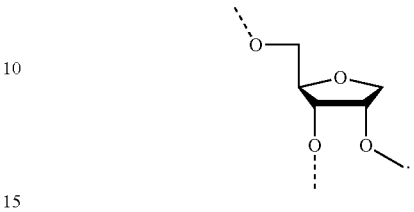

T1, T1', T2', and T3' each independently represent a nucleotide comprising a modification providing the nucleotide a steric bulk that is less or equal to the steric bulk of a 2'-OMe modification. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In one embodiment, T1 is DNA. In one embodiment, T1' is DNA, RNA or LNA. In one embodiment, T2' is DNA or RNA. In one embodiment, T3' is DNA or RNA.

$n^1$, $n^3$, and $q^1$ are independently 4 to 15 nucleotides in length.

$n^5$, $q^3$, and $q^7$ are independently 1-6 nucleotide(s) in length.

$n^4$, $q^2$, and $q^6$ are independently 1-3 nucleotide(s) in length.

$q^5$ is independently 0-10 nucleotide(s) in length.

$n^2$ and $q^4$ are independently 0-3 nucleotide(s) in length. Alternatively, $n^4$ is 0-3 nucleotide(s) in length.

In one embodiment, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$, $q^2$, and $q^6$ are each 1.

In one embodiment, $n^2$, $n^4$, $q^2$, and $q^6$ are each 1.

In one embodiment, C1 is at position 14-17 of the 5'-end of the sense strand, when the sense strand is 19-22 nucleotides in length, and $n^4$ is 1.

In one embodiment, T3' starts at position 2 from the 5' end of the antisense strand. In one example, T3' is at position 2 from the 5' end of the antisense strand and $q^6$ is equal to 1.

In one embodiment, T1' starts at position 14 from the 5' end of the antisense strand. In one example, T1' is at position 14 from the 5' end of the antisense strand and $q^2$ is equal to 1

In one embodiment, T1' and T3' are separated by 11 nucleotides in length (i.e. not counting the T1' and T3' nucleotides.

In one embodiment, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In one embodiment, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In one embodiment, T1 is at cleavage site of the sense strand. In one example, T1 is at position 11 from the 5' end of the sense strand, when the sense strand is 19-22 nucleotides in length, and $n^2$ is 1.

In one embodiment, T2' starts at position 6 from the 5' end of the antisense strand. In one example, T2' is at positions 6-10 from the 5' end of the antisense strand, and $q^4$ is 1.

In one embodiment, B1 is 2'-OMe or 2'-F, n t is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, n t is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, n t is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1.

In one embodiment, B1 is 2'-OMe or 2'-F, n t is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, B1 is 2'-OMe or 2'-F, n t is 8, T1 is 2'F, $n^2$ is 3, B2 is 2'-OMe, n 3 is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, 100%, 95%, 90%, 85%, 80%, 75%, 70%, 65%, 60%, 55%, 50%, 45%, 40%, 35% or 30% of the dsRNA agent of the invention is modified.

In one embodiment, each of the sense and antisense strands of the dsRNA agent is independently modified with acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-0-dimethylaminoethoxyethyl (2'-O-DMAEOE), 2'-O-aminopropyl (2'-O-AP), or 2'-ara-F.

In one embodiment, each of the sense and antisense strands of the dsRNA agent contains at least two different modifications.

In one embodiment, the dsRNA agent of Formula (I) further comprises 3' and/or 5' overhang(s) of 1-10 nucleotides in length. In one example, dsRNA agent of formula (I) comprises a 3' overhang at the 3'-end of the antisense strand and a blunt end at the 5'-end of the antisense strand. In another example, the dsRNA agent has a 5' overhang at the 5'-end of the sense strand.

In one embodiment, the dsRNA agent of the invention does not contain any 2'-F modification.

In one embodiment, the sense strand and/or antisense strand of the dsRNA agent comprises one or more blocks of phosphorothioate or methylphosphonate internucleotide linkages. In one example, the sense strand comprises one block of two phosphorothioate or methylphosphonate internucleotide linkages. In one example, the antisense strand comprises two blocks of two phosphorothioate or methylphosphonate internucleotide linkages. For example, the two blocks of phosphorothioate or methylphosphonate internucleotide linkages are separated by 16-18 phosphate internucleotide linkages.

In one embodiment, each of the sense and antisene strands of the dsRNA agent has 15-30 nucleotides. In one example, the sense strand has 19-22 nucleotides, and the antisense strand has 19-25 nucleotides. In another example, the sense strand has 21 nucleotides, and the antisense strand has 23 nucleotides.

In one embodiment, the nucleotide at position 1 of the 5'-end of the antisense strand in the duplex is selected from the group consisting of A, dA, dU, U, and dT. In one embodiment, at least one of the first, second, and third base pair from the 5'-end of the antisense strand is an AU base pair.

In one embodiment, the antisense strand of the dsRNA agent of the invention is 100% complementary to a target RNA to hybridize thereto and inhibits its expression through RNA interference. In another embodiment, the antisense strand of the dsRNA agent of the invention is at least 95%, at least 90%, at least 85%, at least 80%, at least 75%, at least 70%, at least 65%, at least 60%, at least 55%, or at least 50% complementary to a target RNA.

In one aspect, the invention relates to a dsRNA agent capable of inhibiting the expression of a target gene. The dsRNA agent comprises a sense strand and an antisense strand, each strand having 14 to 40 nucleotides. The sense strand contains at least one thermally destabilizing nucleotide, wherein at at least one said thermally destabilizing nucleotide occurs at or near the site that is opposite to the seed region of the antisense strand (i.e., at position 2-8 of the 5'-end of the antisense strand), For example, the thermally destabilizing nucleotide occurs between positions 14-17 of the 5'-end of the sense strand when the sense strand is 21 nucleotides in length. The antisense strand contains at least two modified nucleic acids that are smaller than a sterically demanding 2'-OMe modification. Preferably, the two modified nucleic acids that is smaller than a sterically demanding 2'-OMe are separated by 11 nucleotides in length. For example, the two modified nucleic acids are at positions 2 and 14 of the 5' end of the antisense strand.

In one embodiment, the sense strand sequence of the dsRNA agent is represented by formula (Is):

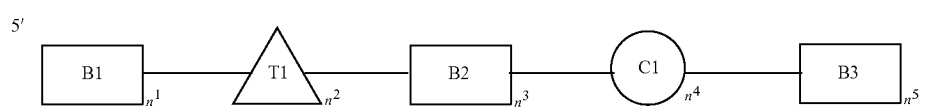

wherein:
B1, B2, and B3 each independently represent a nucleotide containing a modification selected from the group consisting of 2'-Oalkyl, 2'-substituted alkoxy, 2'-substituted alkyl, 2'-halo, ENA, and BNA/LNA;
C1 is a thermally destabilizing nucleotide (e.g., acyclic nucleotide such as UNA or GNA, mismatch, abasic, or DNA) placed at the opposite of the antisense seed region (i.e., positions 2-8 of the 5'-end of the antisense strand);
T1 represents a nucleotide comprising a chemical modification at the 2' position or equivalent position in a non-ribose, acyclic or backbone that provide the nucleotide a less steric bulk than a 2'-OMe modification; for example, T1 is selected from the group consisting of DNA, RNA, LNA, 2'-F, and 2'-F-5'-methyl;
$n^1$ or $n^3$ is independently 4 to 15 nucleotides in length;
$n^5$ is 1-6 nucleotide(s) in length;
$n^4$ is 1-3 nucleotide(s) in length; and
$n^2$ is 0-3 nucleotide(s) in length.

In one embodiment, the sense strand sequence having 19, 20, 21, or 22 nucleotides in length of the dsRNA agent is represented by formula (Is):

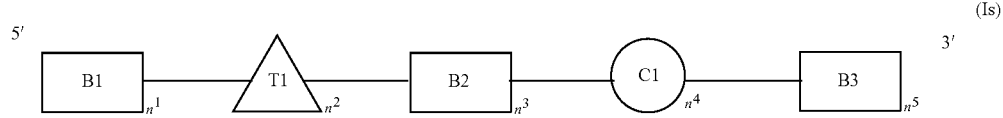

wherein:
B1, B2, and B3 each independently represent a nucleotide containing a modification selected from the group consisting of 2'-Oalkyl, 2'-substituted alkoxy, 2'-substituted alkyl, 2'-halo, ENA, and BNA/LNA;
C1 is a thermally destabilizing nucleotide (e.g., acyclic nucleotide such as UNA or GNA, mismatch, abasic, or DNA) placed at the opposite of the antisense seed region (i.e., positions 2-8 of the 5'-end of the antisense strand);
T1 represents a nucleotide comprising a chemical modification selected from the group consisting of DNA, RNA, LNA, 2'-F, and 2'-F-5'-methyl;
$n^1$ or $n^3$ is independently 4 to 15 nucleotides in length;
$n^5$ is 1-6 nucleotide(s) in length;
$n^4$ is 1-3 nucleotide(s) in length; and
$n^2$ is 0-3 nucleotide(s) in length.

In one embodiment, the dsRNA agent of formula (Is) further comprises 3' and/or 5' overhang(s) of 1-10 nucleotides in length. In one example, the dsRNA agent of formula (Is) comprises a 5' overhang.

In one embodiment, C1 comprises one thermally destabilizing nucleotide at position 14, 15, 16 or 17 from the 5'-end of the sense strand. For example, C1 is an acyclic nucleotide (e.g., UNA or GNA), mismatch, abasic, or DNA. In one specific example, C1 is a GNA.

In one embodiment, T1 comprises a DNA, RNA, LNA, 2'-F, or 2'-F-5'-methyl at position 11 from the 5'-end of the sense strand.

In one embodiment, the dsRNA agent of the invention comprises a sense strand (Is), wherein C1 is an acyclic nucleotide (e.g., UNA or GNA), mismatch, abasic, or DNA; and T1 comprises a DNA, RNA, LNA, 2'-F, or 2'-F-5'-methyl at position 11 from the 5'-end of the sense strand.

In one embodiment, the antisense strand sequence of the dsRNA agent is represented by formula (Ia):

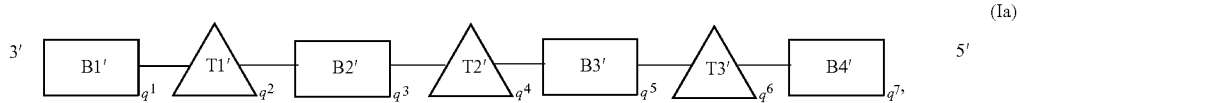

(Ia)

wherein:
B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;

T1', T2', and T3' each independently represent a nucleotide comprising a chemical modification at the 2' position or equivalent position in a non-ribose, acyclic or backbone that provide the nucleotide a less steric bulk than a 2'-OMe modification; for example, T1', T2', and T3' each are independently selected from the group consisting of DNA, RNA, LNA, 2'-F, and 2'-F-5'-methyl;

$q^1$ is independently 4 to 15 nucleotides in length;
$q^3$ or $q^7$ is independently 1-6 nucleotide(s) in length;
$q^2$ or $q^6$ is independently 1-3 nucleotide(s) in length;
$q^4$ is independently 0-3 nucleotide(s) in length; and
$q^5$ is independently 0-10 nucleotide(s) in length.

In one embodiment, the antisense strand sequence having 19, 20, 21, 22, 23, 24, or 25 nucleotides in length of the dsRNA agent is represented by formula (Ia):

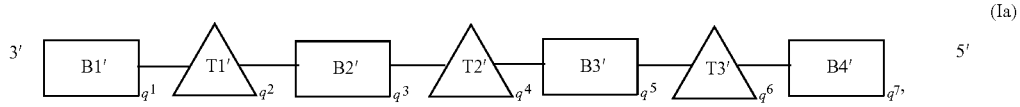

(Ia)

wherein:
B1', B2', B3', and B4' each independently represent a nucleotide containing a modification selected from the group consisting of 2'-O-alkyl, 2'-substituted alkoxy, 2'-substituted alkyl, 2'-halo, ENA, and BNA/LNA;

T1', T2', and T3' each independently represent a nucleotide comprising a chemical modification selected from the group consisting of DNA, RNA, LNA, 2'-F, and 2'-F-5'-methyl;

$q^1$ is independently 4 to 15 nucleotides in length;
$q^3$ or $q^7$ is independently 1-6 nucleotide(s) in length;
$q^2$ or $q^6$ is independently 1-3 nucleotide(s) in length;
$q^4$ is independently 0-3 nucleotide(s) in length; and
$q^5$ is independently 0-10 nucleotide(s) in length.

In one embodiment, dsRNA of formula (Ia) further comprises 3' and/or 5' overhang(s) of 1-10 nucleotides in length. In one example, dsRNA of formula (Ia) comprises a 3' overhang.

In one embodiment, the invention relates to a double-stranded RNA (dsRNA) agent for inhibiting the expression of a target gene. The dsRNA agent comprises a sense strand and an antisense strand, each strand having 14 to 40 nucleotides:

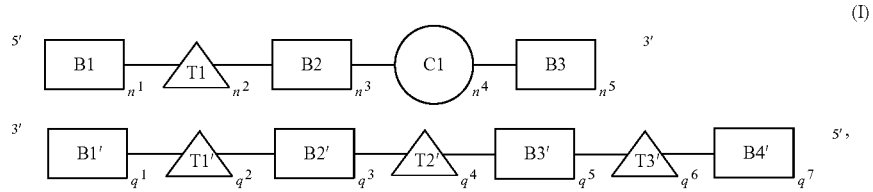

(I)

wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;

C1 is an acyclic nucleotide (e.g., UNA or GNA);
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has 3' and/or 5' overhang(s) of 1-10 nucleotides in length of the antisense and/or sense strand(s).

In one embodiment, the invention relates to a double-stranded RNA (dsRNA) agent for inhibiting the expression of a target gene. The dsRNA agent comprises a sense strand and an antisense strand, each strand having 14 to 40 nucleotides:

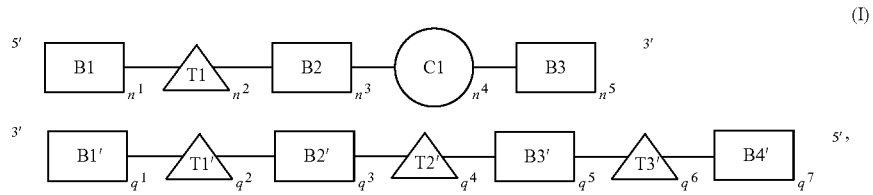

(I)

wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;
C1 is an acyclic nucleotide (e.g., UNA or GNA);
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 3' overhang of 2 nucleotides in length at the 3'-end of the antisense.

In one embodiment, the invention relates to a double-stranded RNA (dsRNA) agent for inhibiting the expression of a target gene. The dsRNA agent comprises a sense strand and an antisense strand, each strand having 15-30 nucleotides:

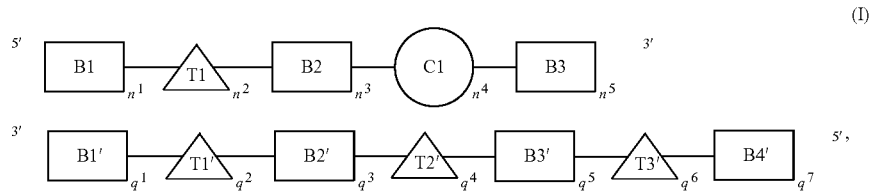

(I)

wherein:
B1, B2, B3, B1', B2', B3', and B4' each independently represent a nucleotide containing a modification 2'-OMe;
C1 is an acyclic nucleotide GNA;
T1, T1', T2', and T3' each are independently DNA or RNA;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 3' overhang of 1-6 nucleotides in length at the 3'-end of the antisense.

In one embodiment, the invention relates to a double-stranded RNA (dsRNA) agent for inhibiting the expression of a target gene. The dsRNA agent comprises a sense strand and an antisense strand, each strand having 19-23 nucleotides:

(I)

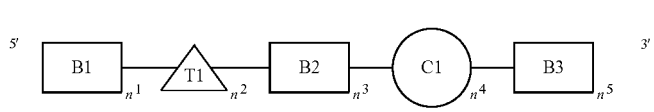

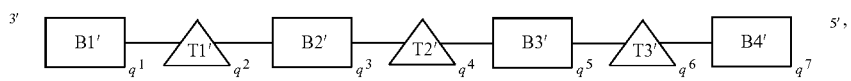

wherein:
B1, B2, B3, B1', B2', B3', and B4' each independently represent a nucleotide containing a 2'-OMe modification;
C1 is an acyclic nucleotide GNA;
T1, T1', T2', and T3' are independently DNA or RNA;
$n^1$, $n^3$, q t, or $q^3$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$, $q^4$ or $q^5$ is independently 0-3 nucleotide(s) in length;
$q^5$ is independently 0-10 nucleotide(s) in length; and
wherein the dsRNA agent has a 3' overhang of 2 nucleotides in length at the 3'-end of the antisense.

In one embodiment, the invention relates to a double-stranded RNA (dsRNA) agent for inhibiting the expression of a target gene. The dsRNA agent comprises a sense strand and an antisense strand, each strand having 14 to 40 nucleotides:

(I)

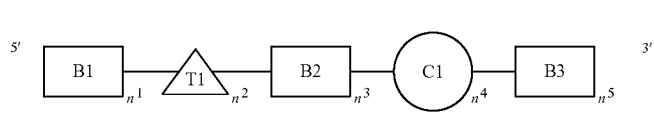

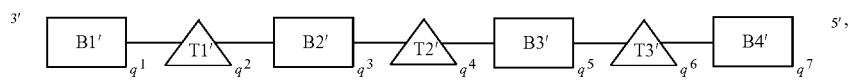

wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;
C1 is an acyclic nucleotide (e.g., UNA or GNA);
T1, T1', T2', and T3' each independently represent a nucleotide comprising a chemical modification selected from the group consisting of DNA, RNA, LNA, 2'-F, and 2'-F-5'-methyl;
$n^1$, $n^3$, or $q^1$ is independently 4 to 15 nucleotides in length;
$n^5$, $q^3$ or $q^7$ is independently 1-6 nucleotide(s) in length;
$n^4$, $q^2$ or $q^6$ is independently 1-3 nucleotide(s) in length;
$n^2$ or $q^4$ is independently 0-3 nucleotide(s) in length;
$q^5$ is independently 0-10 nucleotide(s) in length; and
wherein the dsRNA agent has a 5' overhang of 1-10 nucleotides in length at the 5'-end of the sense.

In one embodiment, the invention relates to a double-stranded RNA (dsRNA) agent for inhibiting the expression of a target gene. The dsRNA agent comprises a sense strand and an antisense strand, each strand having 14 to 40 nucleotides:

(I)

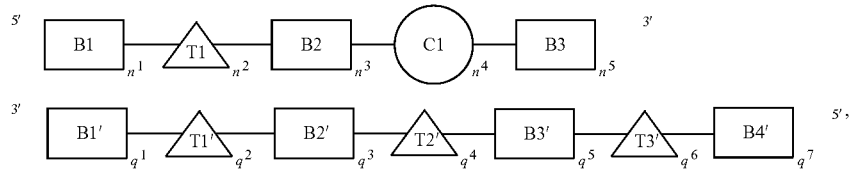

wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;

C1 is an acyclic nucleotide (e.g., UNA or GNA);

T1, T1', T2', and T3' each independently represent a nucleotide comprising a chemical modification selected from the group consisting of DNA, RNA, LNA, 2'-F, and 2'-F-5'-methyl;

$n^1$, $n^3$, or $q^1$ is independently 4 to 15 nucleotides in length;

$n^5$, $q^3$ or $q^7$ is independently 1-6 nucleotide(s) in length;

$n^4$, $q^2$ or $q^6$ is independently 1-3 nucleotide(s) in length;

$n^2$ or $q^4$ is independently 0-3 nucleotide(s) in length;

$q^5$ is independently 0-10 nucleotide(s) in length; and wherein the dsRNA agent has a 5' overhang of 1-6 nucleotides in length at the 5'-end of the sense.

In one embodiment, the invention relates to a double-stranded RNA (dsRNA) agent for inhibiting the expression of a target gene. The dsRNA agent comprises a sense strand and an antisense strand, each strand having 14 to 40 nucleotides:

wherein the dsRNA agent has a 5' overhang of 1-10 nucleotides in length at the 5'-end of the sense and a 3' overhang of 1-10 nucleotides in length at the 5'-end of the antisense strand.

Thermally Destabilizing Modifications

The dsRNA agent can be optimized for RNA interference by increasing the propensity of the dsRNA duplex to disassociate or melt (decreasing the free energy of duplex association) by introducing a thermally destabilizing modification in the sense strand at a site opposite to the seed region of the antisense strand (i.e., at positions 2-8 of the 5'-end of the antisense strand). This modification can increase the propensity of the duplex to disassociate or melt in the seed region of the antisense strand.

The thermally destabilizing modifications can include abasic modification; mismatch with the opposing nucleotide in the opposing strand; and sugar modification such as 2'-deoxy modification or acyclic nucleotide, e.g., unlocked nucleic acids (UNA) or glycerol nucleic acid (GNA).

(I)

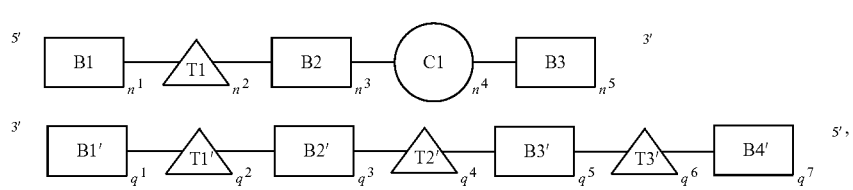

wherein:
B1, B2, B3, B1', B2', B3', and B4' each independently represent a nucleotide containing a modification selected from the group consisting of 2'-Oalkyl, 2'-substituted alkoxy, 2'-substituted alkyl, 2'-halo, ENA, and BNA/LNA;

C1 is an acyclic nucleotide (e.g., UNA or GNA);

T1, T1', T2', and T3' each independently represent a nucleotide comprising a chemical modification selected from the group consisting of DNA, RNA, LNA, 2'-F, and 2'-F-5'-methyl;

$n^1$, $n^3$, or $q^1$ is independently 4 to 15 nucleotides in length;

$n^5$, $q^3$ or $q^7$ is independently 1-6 nucleotide(s) in length;

$n^4$, $q^2$ or $q^6$ is independently 1-3 nucleotide(s) in length;

$n^2$ or $q^4$ is independently 0-3 nucleotide(s) in length;

$q^5$ is independently 0-10 nucleotide(s) in length; and

Exemplified abasic modifications are:

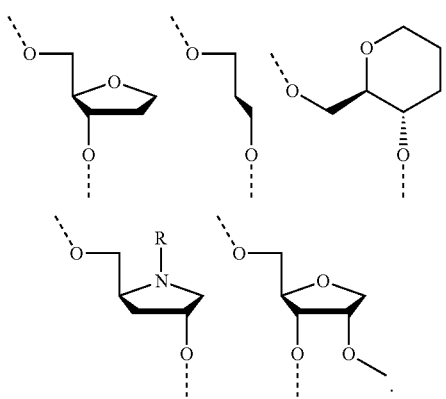

Exemplified sugar modifications are:

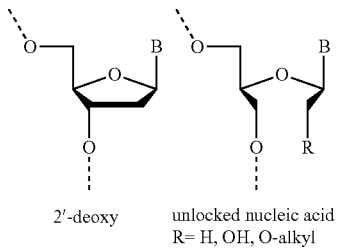

2'-deoxy unlocked nucleic acid
R= H, OH, O-alkyl

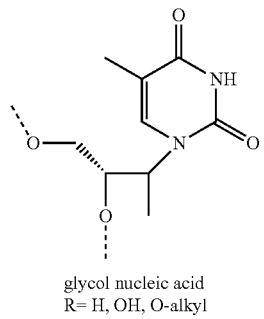

glycol nucleic acid
R= H, OH, O-alkyl

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent and/or at least one of ribose carbons or oxygen (e.g., C1', C2', C3', C4' or O4') are independently or in combination absent from the nucleotide. In some embodiments, acyclic nucleotide is

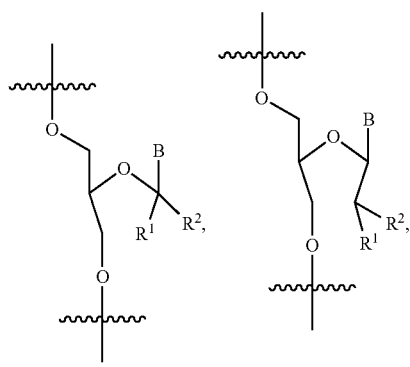

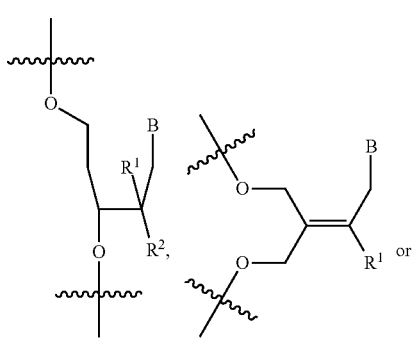

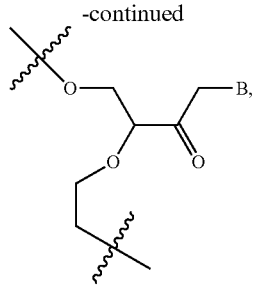

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

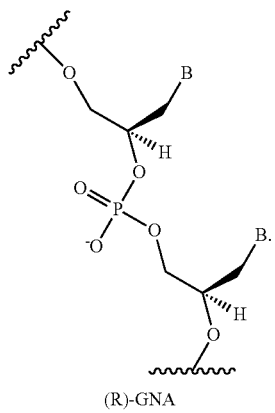

(R)-GNA

The thermally destabilizing modification can be mismatches (i.e., noncomplementary base pairs) between the thermally destabilizing nucleotide and the opposing nucleotide in the opposite strand within the dsRNA duplex. Exemplary mismatch basepairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA agent contains at least one nucleobase in the mismatch pairing that is a 2'-deoxy nucleobase; e.g., the 2'-deoxy nucleobase is in the sense strand.

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

Nucleobase modifications with impaired or completely abolished capability to form hydrogen bonds with bases in the opposite strand have been evaluated for destabilization of the central region of the dsRNA duplex as described in WO 2010/0011895, which is herein incorporated by reference in its entirety. Exemplary nucleobase modifications are:

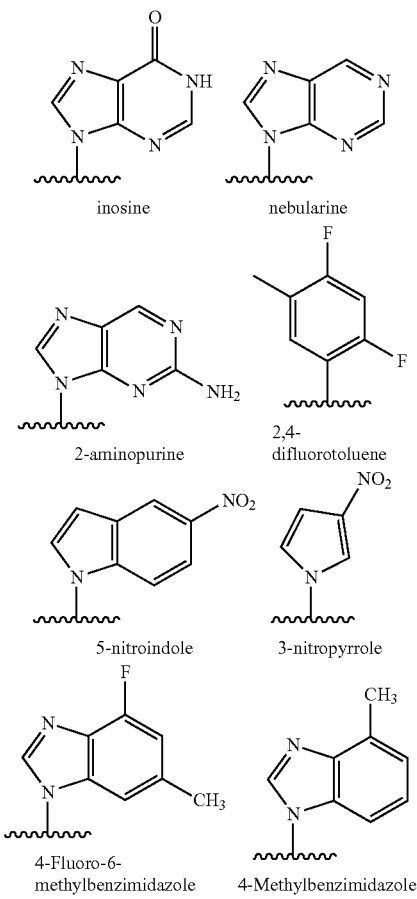

Exemplary phosphate modifications known to decrease the thermal stability of dsRNA duplexes compared to natural phosphodiester linkages are:

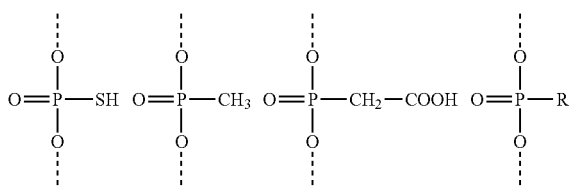

-continued

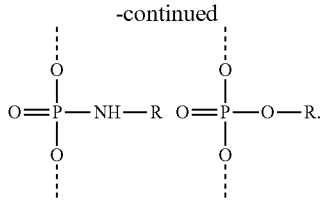

R = alkyl

In one embodiment, the dsRNA agent of the invention can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA agent of the invention can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

In one embodiment, the dsRNA agent is a multimer containing at least two duplexes represented by formula (I), wherein said duplexes are connected by a linker. The linker can be cleavable or non-cleavable. Optionally, said multimer further comprise a ligand. Each of the dsRNA agent can target the same gene or two different genes; or each of the dsRNA agent can target same gene at two different target sites.

In one embodiment, the dsRNA agent is a multimer containing three, four, five, six or more duplexes represented by formula (I), wherein said duplexes are connected by a linker.

The linker can be cleavable or non-cleavable. Optionally, said multimer further comprises a ligand. Each of the dsRNA agent can target the same gene or two different genes; or each of the dsRNA agent can target same gene at two different target sites.

In one embodiment, two dsRNA agent represented by formula (I) are linked to each other at the 5' end, and one or both of the 3' ends of the are optionally conjugated to to a ligand. Each of the dsRNA can target the same gene or two different genes; or each of the dsRNA can target same gene at two different target sites.

Various publications described multimeric siRNA and can all be used with the dsRNA of the invention. Such publications include WO2007/091269, U.S. Pat. No. 7,858,769, WO2010/141511, WO2007/117686, WO2009/014887 and WO2011/031520 which are hereby incorporated by their entirely.

The dsRNA agent that contains conjugations of one or more carbohydrate moieties to a dsRNA agent can optimize one or more properties of the dsRNA agent. In many cases, the carbohydrate moiety will be attached to a modified subunit of the dsRNA agent. E.g., the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one embodiment the dsRNA agent of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

The double-stranded RNA (dsRNA) agent of the invention may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In one embodiment dsRNA agents of the invention are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), (OH)2(O)P-5'-CH2-), 5'-alkyletherphosphonates (R=alkylether=methoxymethyl (MeOCH2-), ethoxymethyl, etc., e.g. RP(OH)(O)—O-5'-).

In one example, the modification can in placed in the antisense strand of a dsRNA agent.

Tunable REVERSIR™ Compounds

In certain instances it is desirable to inhibit siRNA activity. For example, in certain embodiments where the siRNA target is an mRNA, it is may be desirable to inhibit siRNA activity and thereby restore expression of a target protein. For example, certain siRNAs have been used therapeutically. In certain such uses, siRNAs are long-acting. In certain instances, such long acting siRNAs are desirable, for their convenience. In such instances, though, it can also be desirable to have a means to reverse the activity of an siRNA. For example, a patient may respond poorly to treatment or receive too high a dose. In such an instance, a reverser compound can be administered to at least partially reduce the RNAi activity of the siRNA. In certain embodiments, the long-lasting effect of siRNA makes waiting for that effect to slowly diminish through natural clearance an unattractive option.

By way of example, and without limiting the present invention, certain siRNAs are useful for inhibiting blood clotting factors (e.g., Factor II (prothrombin), Factor VII, Factor IX, etc.). Such siRNAs have therapeutic potential as anticoagulants. Long half-lives make such siRNAs particularly attractive, however, if a patient receives too high a dose, has surgery (where anti-coagulation is undesirable) or otherwise desires a decrease in the anti-coagulant effect, a reverser compound to the anti-coagulant siRNA can be administered. Such tunable REVERSIR™ compound will restore coagulation function more quickly than simply waiting for natural clearance of the siRNA. This example is provided for illustrative purposes. Many siRNAs have been designed to a vast number of targets, including without limitation, a vast number of messenger RNA (mRNA) targets and pre-mRNA targets, as well as a vast number of non-coding RNA targets. tunable REVERSIR™ compounds provided herein are suitable for any siRNA, regardless of the target or mechanism of the siRNA compound.

In certain embodiments, the invention provides tunable REVERSIR™ compounds to an siRNA targeted to an mRNA. In certain such embodiments, the target mRNA encodes a protein involved in metabolism. In certain such embodiments, the target mRNA encodes a protein involved in cardiac function. In certain embodiments, the target mRNA encodes a protein involved in blood-clotting. Exemplary siRNA compounds targeting any of a variety of target proteins are known in the art. Further, methods for preparing siRNA against a target gene are well known in the art and readily available to one of skill in the art.

Without limitations, target genes for siRNAs include, but are not limited to genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Specific exemplary target genes for the siRNAs include, but are not limited to, AT3, AGT, ALAS1, Factor XI, Factor XII, CC3, CC5, TMPR, HAO1, AGT, C5, CCR-5, PDGF beta gene; Erb-B gene, Src gene; CRK gene; GRB2 gene; RAS gene; MEKK gene; JNK gene; RAF gene; Erk1/2 gene; PCNA(p21) gene; MYB gene; c-MYC gene; JUN gene; FOS gene; BCL-2 gene; Cyclin D gene; VEGF gene; EGFR gene; Cyclin A gene; Cyclin E gene; WNT-1 gene; beta-catenin gene; c-MET gene; PKC gene; NFKB gene; STAT3 gene; survivin gene; Her2/Neu gene; topoisomerase I gene; topoisomerase II alpha gene; p73 gene; p21(WAF1/CIP1) gene, p27(KIP1) gene; PPM1D gene; caveolin I gene; MIB I gene; MTAI gene; M68 gene; tumor suppressor genes; p53 gene; DN-p63 gene; pRb tumor suppressor gene; APC1 tumor suppressor gene; BRCA1 tumor suppressor gene; PTEN tumor suppressor gene; MLL fusion genes, e.g., MLL-AF9, BCR/ABL fusion gene; TEL/AML1 fusion gene; EWS/FLI1 fusion gene; TLS/FUS1 fusion gene; PAX3/FKHR fusion gene; AML1/ETO fusion gene; alpha v-integrin gene; Flt-1 receptor gene; tubulin gene; Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, 1-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCAT gene, SCA8 gene, allele gene found in loss of heterozygosity (LOH) cells, one allele gene of a polymorphic gene and combinations thereof.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in duploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific modulation of one allele of an essential gene with a composition of the invention.

In certain embodiments, the invention provides tunable REVERSIR™ compound to an siRNA that modulates a micro-RNA.

Tunable REVERSIR™ compounds are oligomeric compounds. Accordingly, in certain embodiments, tunable REVERSIR™ compounds comprise, for example and without limitation, any of the modifications and motifs described in the discussion herein for oligomeric compounds.

In certain embodiments, motifs are designed with consideration given to both the siRNA and the tunable REVERSIR™ compound. In certain embodiments, a tunable REVERSIR™ compound could comprise 4 or more contiguous DNA-like monomers. In certain embodiments, the resulting RNA/DNA duplex could activate RNase H, resulting in cleavage of the RNA-like antisense compound. In certain embodiments, tunable REVERSIR™ activity does not depend on enzymatic activity. In certain such embodiments, compounds designed without regard for enzymatic compatibility may incorporate modifications to improve other attributes. For example, certain motifs yield oligomeric compounds with high affinity for a target nucleic acid, but that are unable to elicit enzymatic cleavage of that target. Such motifs may be useful for tunable REVERSIR™ compounds in embodiments where cleavage of the siRNA is not necessary.

In certain embodiments, one strand of the siRNA, e.g., the strand complementary to tunable REVERSIR™ compound, and corresponding tunable REVERSIR™ compound are the same length. In some embodiments, one strand of the siRNA, e.g., the strand complementary to tunable REVERSIR™ compound, and corresponding tunable REVERSIR™ compound are different lengths. In some embodiments, the tunable REVERSIR™ compound is shorter than the corresponding complementary strand from the siRNA. In some embodiments, the tunable REVERSIR™ compound is shorter by 1, 2, 3, 4, 5, 6, 7, 8, 9, 10 or more nucleotides than the corresponding complementary strand from the siRNA.

In certain embodiments, antisense strand of the siRNA and corresponding tunable REVERSIR™ compound are the same length. In some embodiments, antisense strand of the siRNA and corresponding tunable REVERSIR™ compound are different lengths. In some embodiments, the tunable REVERSIR™ compound is shorter than the corresponding complementary antisense strand from the siRNA. In some embodiments, the tunable REVERSIR™ compound is shorter by 1, 2, 3, 4, 5, 6, 7, 8, 9, 10 or more nucleotides than the corresponding complementary antisense strand from the siRNA.

In certain embodiments, sense strand of the siRNA and corresponding tunable REVERSIR™ compound are the same length. In some embodiments, sense strand of the siRNA and corresponding tunable REVERSIR™ compound are different lengths. In some embodiments, the tunable REVERSIR™ compound is shorter than the corresponding complementary sense strand from the siRNA. In some embodiments, the tunable REVERSIR™ compound is shorter by 1, 2, 3, 4, 5, 6, 7, 8, 9, 10 or more nucleotides than the corresponding complementary sense strand from the siRNA.

In certain embodiments, an siRNA and a tunable REVERSIR™ compound are administered to a patient. In certain such embodiments, pharmaceutical compositions comprising an siRNA and those comprising a tunable REVERSIR™ compound comprise the same formulation. In certain embodiments, pharmaceutical compositions comprising an siRNA and those comprising a tunable REVERSIR™ compound comprise different formulations. In certain embodiments an siRNA and a tunable REVERSIR™ compound are administered by the same route. In certain embodiments an siRNA and a tunable REVERSIR™ compound are administered by different routes. For example, in certain embodiments, an siRNA is administered orally and a tunable REVERSIR™ compound is administered by injection. In certain embodiments, the dosages of the siRNA and the tunable REVERSIR™ compound are the same. In certain embodiments, the dosages of the siRNA and the tunable REVERSIR™ compound are different.

In certain embodiments, the safety profiles of the siRNA and the tunable REVERSIR™ compound are similar. In certain embodiments, such toxicity profiles are different. For example, in certain embodiments, an siRNA can be intended for chronic administration and the tunable REVERSIR™ compound is only intended for acute use as needed. In such embodiments, the tolerance for toxic side-effects of the tunable REVERSIR™ compound can be higher. Accordingly, modifications and motifs that may be too toxic for use in an siRNA can be acceptable in a tunable REVERSIR™ compound. For example, in certain embodiments, oligomeric compounds comprising one or more LNA nucleotide have been shown to have high affinity for a target nucleic acid, but in certain embodiments have been shown to cause safety findings or toxicity findings at relatively low concentrations. For certain siRNAs, where chronic administration is intended, certain such compounds comprising LNA may not be suitable. However, in embodiments where a tunable REVERSIR™ compound is not intended for chronic administration, but rather for acute administration when siRNA activity is problematic, such LNA modifications in an antidote compound are acceptable. The increased affinity of LNA can improve the tunable REVERSIR™ effect and since the tunable REVERSIR™ compound is only administered as a single administration or for a short period of time, and possibly when the patient is in distress, the increased toxicity of LNA may be justified. Other high affinity, but potentially toxic modifications are also known.

In certain embodiments, activity of siRNA is counteracted by a non-oligomeric tunable REVERSIR™. For example, in certain embodiments, when the target nucleic acid is a target mRNA encoding a protein it is desirable to reduce the activity of siRNA and to increase in the amount of the target protein (e.g., target protein amount has gone too low, or circumstances have changed resulting in the desire to restore target protein amount). In such embodiments, one can simply administer the target protein itself. Such administration will immediately reverse the siRNA activity of target protein reduction. However, it can also be desirable to administer an oligomeric tunable REVERSIR™ compound according to the present invention. For example, the target protein may have a short half-life in the animal. Accordingly, to maintain the restored target protein concentration would require repeated administration of target protein until the siRNA has cleared and normal protein expression is restored. In certain such embodiments, it is still desirable to administer an tunable REVERSIR™ compound to shorten the duration of the siRNA activity. In certain embodiments an oligomeric tunable REVERSIR™ compound is co-administered with a non-oligomeric tunable REVERSIR™. In certain such embodiments, the non-oligomeric tunable REVERSIR™ is a target protein. In certain embodiments, the non-oligomeric tunable REVERSIR™ compound is a protein having similar physiological effect as a target protein or that stimulates expression of the target protein.

In certain embodiments, the activity of siRNA is counteracted by oligomeric tunable REVERSIR™ compound according to the present invention. In certain embodiments, at a later timepoint following the time of administration of oligomeric tunable REVERSIR™ compound, the oligomeric tunable REVERSIR™ compound's action of reducing the activity of an siRNA is counteracted by the administration of the same siRNA.

In certain embodiments, the action of tunable REVERSIR™ compound allows on-drug and off-drug control of the therapeutic action of an siRNA drug, where the sequence of on-drug and off-drug action of the siRNA can be performed by the sequential administration of the tunable REVERSIR™, preceeded and/or followed by the administration of the therapeutic siRNA.

Research Tools

In certain instances, siRNAs have been used as research tools. For example, researchers investigating the function of a particular gene product can design siRNAs to reduce the amount of that gene product present in a cell or an animal and observe phenotypic changes in the cell or animal. In certain embodiments, the present invention provides methods for reducing the amount of a gene product in a cell or animal through RNAi and then reducing that RNAi activity, thereby restoring the inhibited gene product. In certain embodiments, investigators can use such techniques to characterize proteins or untranslated nucleic acids. In certain embodiments, investigators can vary the amount of time between siRNA and tunable REVERSIR™ compounds administration. In certain embodiments, such experiments are used to investigate kinetics and/or turnover of gene products and/or certain cellular functions.

As described herein, the invention provides methods comprising administering to a subject a siRNA followed by administering a tunable REVERSIR™ compound or composition comprising same. Without limitation, the siRNA and the tunable REVERSIR™ compound can be conjugated or unconjugated. Further, the siRNA and the tunable REVERSIR™ compound can be independently encapsulated in a lipid formulation, e.g., a LNP, or other nucleic acid-lipid particle. Moreover, the siRNA and the tunable REVERSIR™ compound can be administered, independently, via any appropriate route or mode of administration. For example, the siRNA and the tunable REVERSIR™ compound can be independently administered via intravenous administration (IV) or via subcutaneous administration (SC).

Accordingly, in some embodiments, the invention provides methods comprising administering to a subject an unconjugated siRNA followed by administering a conjugated tunable REVERSIR™ compound, wherein the tunable REVERSIR™ compound is encapsulated in a lipid formulation, e.g., a LNP, or other nucleic acid-lipid particle, and wherein the tunable REVERSIR™ compound is administered via intravenous administration.

In some other embodiments, the invention provides methods comprising administering to a subject an unconjugated siRNA followed by administering a conjugated tunable REVERSIR™ compound, wherein the tunable REVERSIR™ compound is encapsulated in a lipid formulation and the tunable REVERSIR™ compound is administered via subcutaneous administration.

In yet some other embodiments, the invention provides methods comprising administering to a subject a conjugated siRNA followed by administering a conjugated tunable REVERSIR™ compound, wherein the tunable REVERSIR™ compound is encapsulated in a lipid formulation and the tunable REVERSIR™ compound is administered via intravenous administration.

In still some other embodiments, the invention provides methods comprising administering to a subject a conjugated siRNA followed by administering a conjugated tunable REVERSIR™ compound, wherein the tunable REVERSIR™ compound is encapsulated in a lipid formulation and the tunable REVERSIR™ compound is administered via subcutaneous administration.

While the above described embodiments specify conjugated tunable REVERSIR™ compounds, unconjugated tunable REVERSIR™ compounds can also be used. Thus, in some embodiments, the invention provides methods comprising administering to a subject an unconjugated siRNA followed by administering an unconjugated tunable REVERSIR™ compound, wherein the tunable REVERSIR™ compound is encapsulated in a lipid formulation and the tunable REVERSIR™ compound is administered via intravenous administration. In some other embodiments, the invention provides methods comprising administering to a subject an unconjugated siRNA followed by administering an unconjugated tunable REVERSIR™ compound, wherein the tunable REVERSIR™ compound is encapsulated in a lipid formulation and the tunable REVERSIR™ compound is administered via subcutaneous administration. In yet some other embodiments, the invention provides methods comprising administering to a subject a conjugated siRNA followed by administering an unconjugated tunable REVERSIR™ compound, wherein the tunable REVERSIR™ compound is encapsulated in a lipid formulation and the tunable REVERSIR™ compound is administered via intravenous administration.

In still some other embodiments, the invention provides methods comprising administering to a subject a conjugated siRNA followed by administering an unconjugated tunable REVERSIR™ compound, wherein the tunable REVERSIR™ compound is encapsulated in a lipid formulation and the tunable REVERSIR™ compound is administered via subcutaneous administration.

Kits

In certain embodiments, the present invention provides kits comprising one or more siRNAs and one or more corresponding tunable REVERSIR™ compound. In certain embodiments, such kits are intended for therapeutic application. In certain embodiments, such kits are intended for research use.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

The nucleotide sequences set forth in the sequence listing and Examples, are independent of any modification to a sugar moiety, a monomeric linkage, or a nucleobase. As such, oligomeric compounds defined by a SEQ ID NO can comprise, independently, one or more modifications to a sugar moiety, an internucleoside or internucleotide linkage, or a nucleobase.

Exemplary embodiments of the various aspects disclosed herein can be described by one or more of the following numbered paragraphs:

1. A tunable REVERSIR™ compound comprising 8 or 9 modified nucleotides, wherein at least three of the modified nucleotides are high affinity monomers and one of the high affinity monomers is base paired with the 6th nucleotide from the 5'-end of the target strand of the siRNA.
2. The tunable REVERSIR™ compound of paragraph 1, wherein the high affinity monomer is an LNA.
3. The tunable REVERSIR™ compound of paragraph 2, wherein the compound comprises three or four LNA nucleotides.
4. The tunable REVERSIR™ compound of any one of paragraphs 1-3, wherein the compound is a single-stranded oligonucleotide that is at least 90% complementary to the antisense strand.
5. The tunable REVERSIR™ compound of any one of paragraphs 1-4, wherein the compound is fully complementary to the antisense strand.
6. The tunable REVERSIR™ compound of any one of paragraphs 1-5, wherein the compound comprises at least one modified internucleotide linkage.
7 The tunable REVERSIR™ compound of paragraph 6, wherein internucleotide linkage is a phosphorothioate.
8. The tunable REVERSIR™ compound of paragraph 7, wherein the compound comprises not more than three or four phosphorothioate modifications.
9. The tunable REVERSIR™ compound of any one of paragraphs 1-8, wherein the compound is conjugated with a ligand.

10. The tunable REVERSIR™ compound of paragraph 9, wherein the ligand is

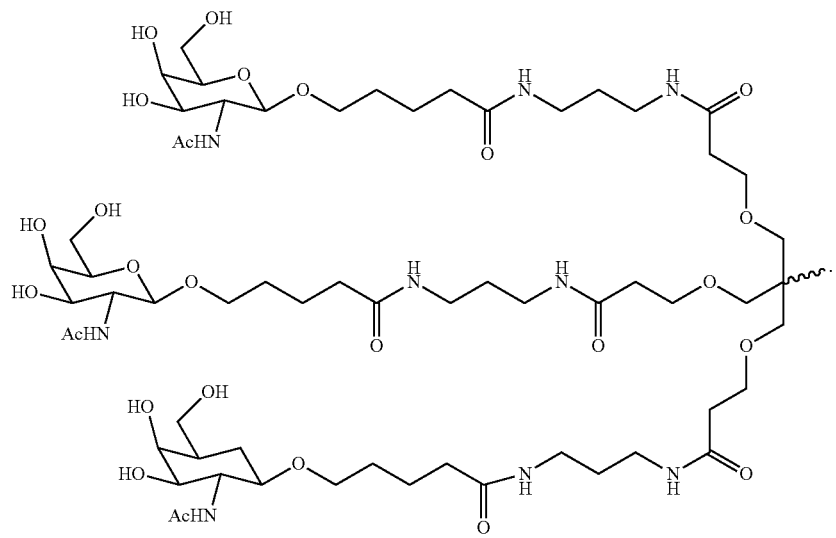

11. The tunable REVERSIR™ compound of paragraph 9, wherein the ligand is conjugated to 3'-terminus of the compound.
12. The tunable REVERSIR™ compound of any one of paragraphs 1-11, wherein the modified oligonucleotide is conjugated with a ligand and the ligand is conjugated to a nucleotide with a deoxy sugar in the tunable REVERSIR™ compound.
13. The tunable REVERSIR™ compound of paragraph 12, wherein said deoxy sugar is a 2'-deoxy ribose.
14. The tunable REVERSIR™ compound of any one of paragraphs 1-13, wherein the siRNA is targeted to an mRNA, a pre-mRNA, a micro-RNA a pre-micro-RNA.
15. The tunable REVERSIR™ compound of any one of paragraphs 1-14, wherein the siRNA is conjugated with a ligand.
16. A kit comprising a tunable REVERSIR™ compound of any one of paragraphs 1-15.
17. A kit comprising a siRNA and a tunable REVERSIR™ compound of any one of paragraphs 1-15.
18. A method or a system for assessing the efficacy and safety of a pharmaceutical composition for use in the treatment or prophylaxis of a disease, the method comprising the steps of:
   (1) treating all subjects with the pharmaceutical composition for a first treatment time frame,
   (2) deriving mRNA level and/or physiological outcome measures for the all subjects,
   (3) separating the responder members of the treated subjects from the non-responder members,
   (4) randomizing and stratifying members of the responders into at least two further sub-groups,
   (5) continue treating members of one sub-group in (4) with the pharmaceutical composition, and treating members of the other sub-group with a REVERSIR™ compound described in any one of paragraphs 1-15 for a second treatment timeframe,
   (6) deriving mRNA level and/or physiological outcome measures for the sub-groups,
   (7) comparing the outcomes at (6) with the outcomes at (2),
   (8) using the comparison in (7) to derive an efficacy and safety measures for the pharmaceutical composition.
19. A method or a system for assessing the efficacy and safety of a pharmaceutical composition for use in the treatment or prophylaxis of a disease, the system comprising the steps of:
   (1) stratifying a subject group into at least two sub-groups,
   (2) treating members of one sub-group with the pharmaceutical composition for a first treatment timeframe, and treating members of a second sub-group with a blinded placebo,
   (3) deriving mRNA level, and/or biomarker and/or physiological outcome measures for the sub-groups,
   (4) treating members of the treated sub-group with a tunable REVERSIR™ compound described in any one of paragraphs 1-15, and treating members of the other blinded placebo sub-group with the pharmaceutical composition for a second treatment timeframe,
   (5) deriving mRNA level and/or physiological outcome measures for the sub-groups,
   (6) comparing the outcomes at (5) with the outcomes at (3),
   (7) using the comparison in (6) to derive an efficacy and safety measures for the pharmaceutical composition.
20. The method or system as in paragraph 18 or paragraph 19, wherein the disorder is caused by an aberrant expression of a target gene.
21. The method or system as in paragraph 20, wherein the pharmaceutical composition is an oligonucleotide.
22. The method or system as in paragraph 21, wherein the oligonucleotide is an antisense or a siRNA.
23. The method or system as in paragraph 21, wherein the oligonucleotide provided a durable pharmacodynamics.
24. The method or system as in paragraph 18, wherein the tunable REVERSIR™ compound described in any one of paragraphs 1-15 is used to equalize and enable randomized withdrawal of the treated members.
25. The method or system as in paragraph 18, wherein the administration of the tunable REVERSIR™ compound of claim 1 is blinded with placebo administration of the pharmaceutical composition.

26. The method or system as in paragraph 18 or paragraph 19, wherein the tunable REVERSIR™ compound describe in any one of paragraphs 1-15 induces a washout in the treated sub-group.
27. The method or system as in paragraph 18, wherein the tunable REVERSIR™ compound described in any one of paragraphs 1-15 resets the baseline of the RNAi acidity.
28. The method or system as in paragraph 19, wherein the siRNA can be redose after at least one, two, three, or four weeks after tunable REVERSIR™ treatment.
29. The method or system as in paragraph 20, wherein the target gene is selected from the group consisting of TTR, AGT, ALAS-1, G01, AT3, Factor XI, Factor XII, CC3, CC5, AAT, Eg5, PCSK9, TPX2, apoB, SAA, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-I gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21 (WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.
30. The method or system as in paragraph 18, wherein the first timeframe is until the completion of an open-label study or a single blinded study.
31. The method or system as in paragraph 18, wherein the second timeframe is about one one week to one month, two months, three months, four months, five months, or six months.
32. The method or system as in paragraph 18, wherein the second timeframe is until the completion of a clinical study.
33. A method or system as in any one of the proceeding numbered paragraphs, wherein the method or system constitutes a clinical trial or system for performing a clinical trial for testing the pharmaceutical.
34. A method or system as in any one of the proceeding paragraphs s, wherein the method or system is to assess a treatment regime employing the pharmaceutical for its efficacy.

EXAMPLES

Example 1: Oligonucleotide Synthesis

All oligonucleotides were prepared on a MerMade 192 synthesizer on a 1 μmole scale using custom GalNAc supports.[11] LNA phosphoramidites were purchased from Exiqon. All phosphoramidites were used at a concentration of 100 mM in 100% acetonitrile, 9:1 acetonitrile:DMF (2'-OMe-C, 2'-OMe-U), or 1:1 DCM:acetonitrile (LNA-5-Me-C) with a standard protocol for 2-cyanoethyl phosphoramidites and ETT activator, except that the coupling time was extended to 400 seconds. Phosphate oxidation to phosphate or sulfurization to phosphorothioate was achieved using a solution of 50 mM iodine in 9:1 acetonitrile:water or 100 mM 1,2,4-dithiazole-5-thione (DDTT) in 9:1 pyridine:acetonitrile, respectively. After the trityl-off synthesis, columns were incubated with 150 μL of 40% aqueous methylamine for 30 min at room temperature and the solution was drained via vacuum into a 96-well plate. After repeating the incubation and draining with a fresh portion of aqueous methylamine, the plate containing crude oligonucleotides solution was sealed and shaken at 60° C. for an additional 30 min to completely remove all protecting groups. Precipitation of the crude oligonucleotides was accomplished via the addition of 1.2 mL of 9:1 acetonitrile:EtOH to each well, followed by incubation at −20° C. overnight. The plate was then centrifuged at 3000 RPM for 45 min at 4° C., the supernatant removed from each well, and the pellets resuspended in 950 μL of 20 mM aqueous NaOAc. For those Tunable REVERSIR™ molecules which did not precipitate (shorter than ~10 nucleotides), they were concentrated in vacuo and redissolved in 1.0 mL of 20 mM aqueous NaOAc. Each crude solution was finally desalted over a GE Hi-Trap desalting column (Sephadex G25 Superfine) using water to elute the final oligonucleotide products. The identities and purities of all oligonucleotides were confirmed by ESI-MS and IEX HPLC, respectively.

Example 2: In Vivo TTR Gene Silencing Experiments in Wild-Type Mice

All procedures were conducted by certified laboratory personnel using protocols consistent with local, state and federal regulations, as applicable, and approved by the (i) Institutional Animal Care and Use Committee; (ii) AAALAC (Association for Assessment and Accreditation of Laboratory Animal Care International)—accreditation number: 001345. C57BL/6 female mice, aged 6-8 weeks acquired from Charles River Laboratories (n=3 per group) were dosed subcutaneously at a volume of 10 μL GalNAc conjugate (siRNA AD-57727 or Tunable REVERSIR™) per gram of body weight. Control group was dosed with phosphate buffered saline (PBS). Serum samples were collected and analyzed for siRNA activity for specific target proteins as described below. Serum TTR protein was quantified by ELISA from serum isolated from whole blood. ELISA was performed according to manufacturer protocol (ALPCO, 41-PALMS-E01) after a 3025-fold dilution of the serum samples. Data were normalized to pre-bleed TTR levels. Group averages are depicted with ±SD. All samples were assayed in duplicate and each data point is the average of all the mice within each cohort (n=3).

Example 3: The Base Pair Between the Nucleotide in Position g6 in the Guide (Antisense) Strand of the Target siRNA and the Complementary Nucleotide in the Tunable REVERSIR™ Compound has an Impact on Tunable REVERSIR™ Potency TTR-siRNA-GalNAc conjugate (AD-57727) was subcutaneously (SC) administered in wild type mice on Day 0 at a dose of 3 mg/kg, followed by SC administration of tunable REVERSIR™ compounds at a dose of 0.1 mg/kg on Day 7. Following tunable REVERSIR™ administration, serum bleeds were collected on Days 9, 11, and 14 and the TTR protein levels were analyzed and are plotted in FIG. 1. The results showed that introduction of an LNA modification in the tunable REVERSIR™ nucleotide opposite nucleotide g6 of the guide (antisense) strand of the target siRNA impaired high potency of the tunable REVERSIR™ agent. The g6-LNA-paired tunable REVERSIR™ agent A-146092.1 with a total of 5 LNA modified nucleotides showed total reversal of TTR levels in serum by Day 11. When the LNA modification was removed from the nucleotide base-paired with the target's nucleotide g6, in a different 5 LNA tunable REVERSIR™ (A-146131.1), reversal of TTR levels to only 40% was achieved, relative to the no tunable REVERSIR™ PBS control group, when using the same tunable REVERSIR™ dose.

Figure 2:
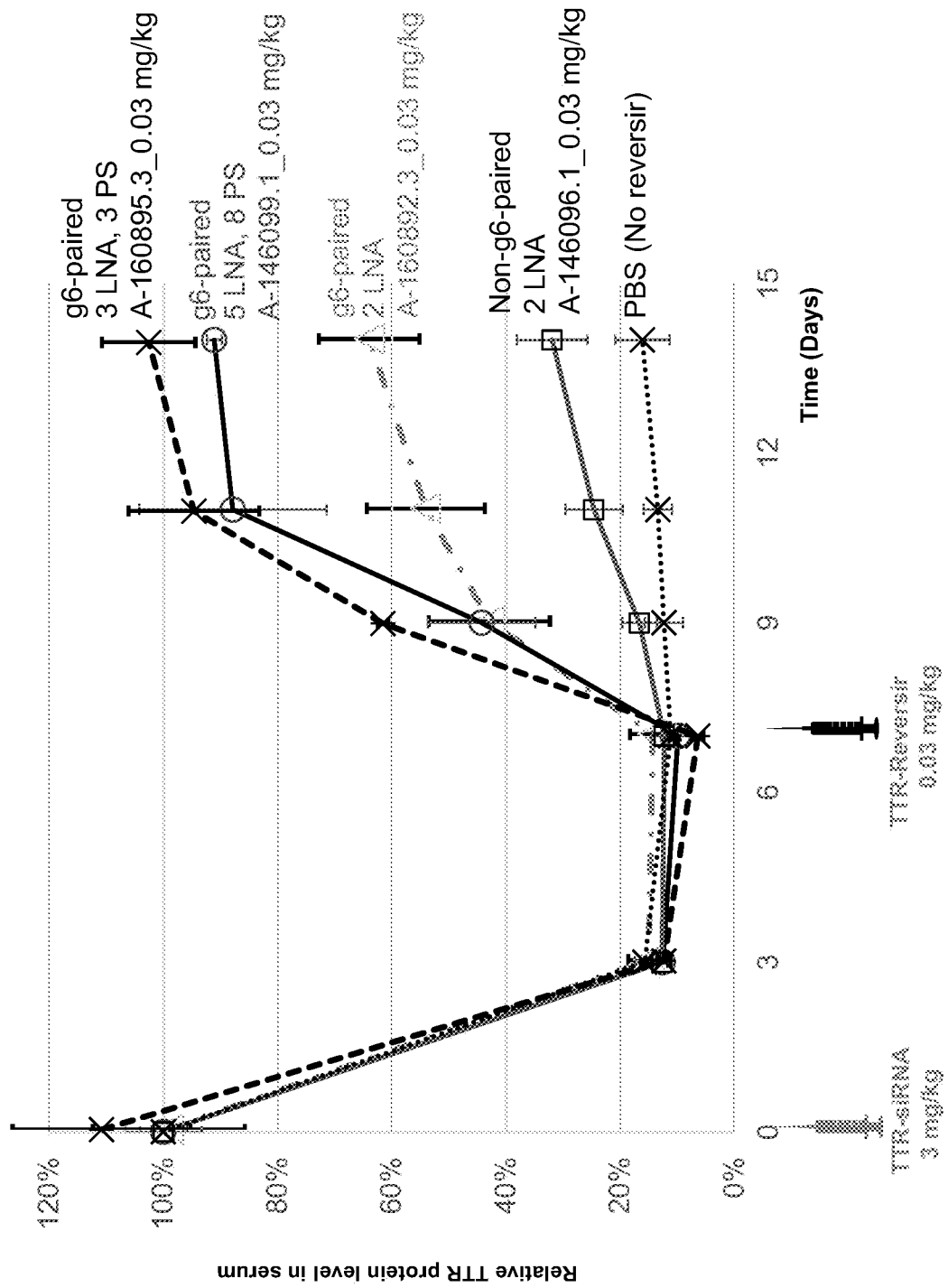
FIG. 2 shows in vivo activity of exemplary 9-mer tunable REVERSIR™ compounds targeting TTR siRNAs and having different potencies of RNAi activity reversal based on base pairing with position g6 in the guide siRNA strand.

Example 4: Correct Positioning of LNA Modifications in the Modified Nucleotides of a Tunable REVERSIR™ Agent Allows Reduction of the Number of LNAs in Tunable REVERSIR™ while Preserving Highly Potent Tunable REVERSIR™ Compounds TTR-siRNA-GalNAc conjugate (AD-57727) was subcutaneously (SC) administered in wild type mice on Day 0 at a dose of 3 mg/kg, followed by SC administration of different tunable REVERSIR™ molecules at a dose of 0.03 mg/kg on Day 7. Following tunable REVERSIR™ administration, serum bleeds were collected on Days 9, 11, and 14 and the TTR protein levels were analyzed and are plotted in FIG. 2. The results showed that introduction of an LNA modification in the tunable REVERSIR™ position paired with g6 even in a tunable REVERSIR™ with only 2 LNAs (A-160892.3) conferred significant reversal (40%) of TTR levels in mouse serum. In comparison, the tunable REVERSIR™ of the same sequence and same 2 LNA content, but positioned at non-g6-paired nucleotides (A-146096.1) showed almost no reversal of TTR levels (FIG. 2), relative to the no tunable REVERSIR™ PBS control group, when using the same tunable REVERSIR™ dose. In addition, maintaining the tunable REVERSIR™ position opposite g6 as an LNA base-pair with the target, provided equally potent tunable REVERSIR™ agents with either 3 LNAs (A-160895.3) or 5 LNAs (A-146099.1), where both tunable REVERSIR™ compounds showed total reversal of TTR levels in serum by Day 11, relative to the no REVERSIR™ PBS control group (FIG. 2).

Figure 3:
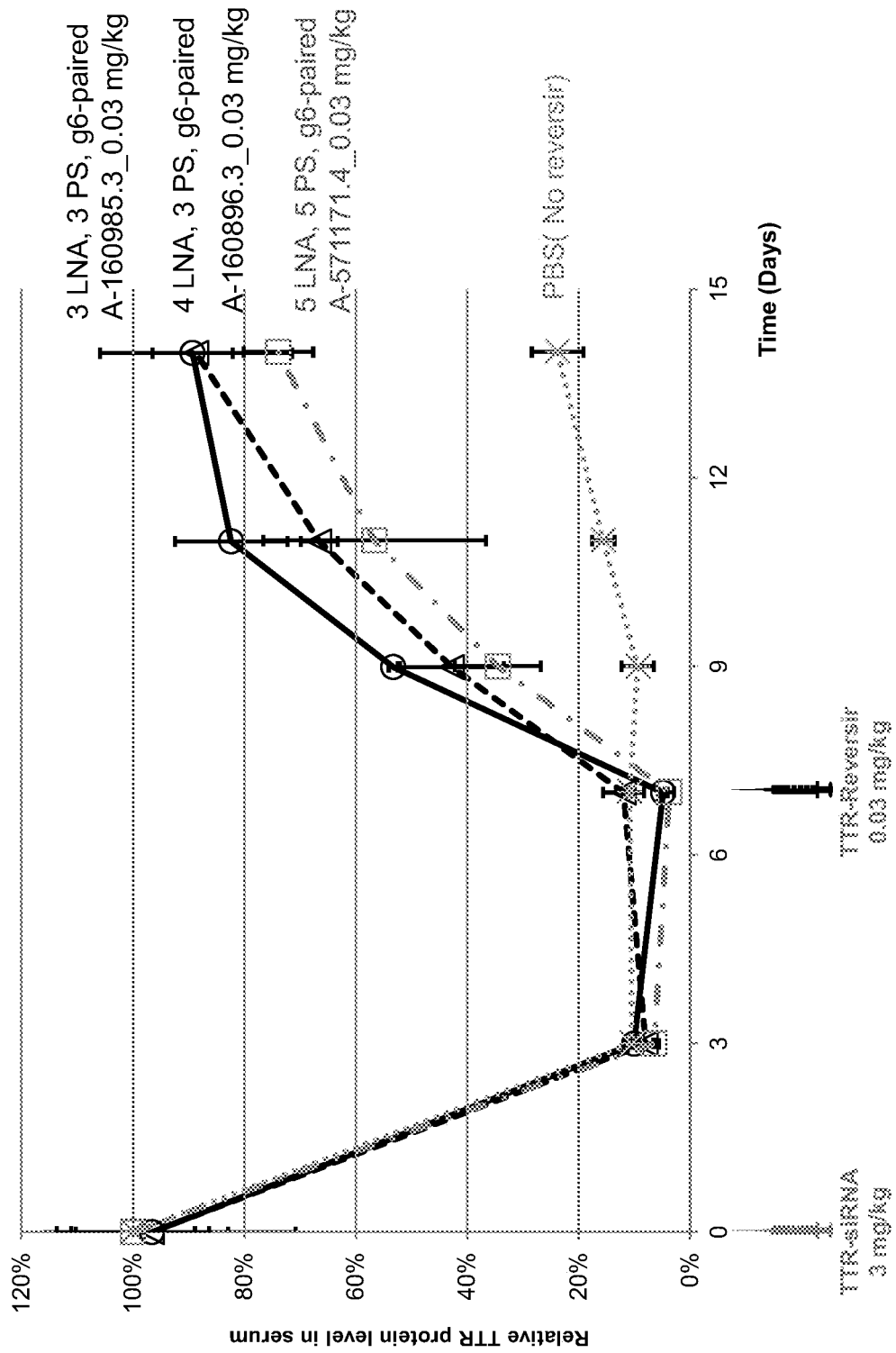
FIG. 3 shows in vivo activity of exemplary 9-mer tunable REVERSIR™ compounds targeting TTR siRNAs and having different content of Locked Nucleic Acids (LNA) nucleotides and phosphorothioate (PS) backbone modifications.

Example 5: G6-Paired LNA Tunable REVERSIR™ Agent with Reduced Number of LNAs in Tunable REVERSIR™ Maintains High Potency of Target Reversal in Mice TTR-siRNA-GalNAc conjugate (AD-57727) was subcutaneously (SC) administered in wild type mice on Day 0 at a dose of 3 mg/kg, followed by SC administration of different tunable REVERSIR™ molecules at a dose of 0.03 mg/kg on Day 7. Following tunable REVERSIR™ administration, serum bleeds were collected on Days 9, 11, and 14 and the TTR protein levels were analyzed and are plotted in FIG. 3. The results showed that maintaining the tunable REVERSIR™ position opposite g6 as an LNA base-pair with the target, provided potent tunable REVERSIR™ agents with either 3 LNAs (A-160895.3), 4 LNAs (A-160896.3) or 5 LNAs (A-571171.4), where all three tunable REVERSIR™ compounds showed high reversal of TTR levels in serum by Day 11 (>60%), relative to the no REVERSIR™ PBS control group (FIG. 3).

Figure 4:
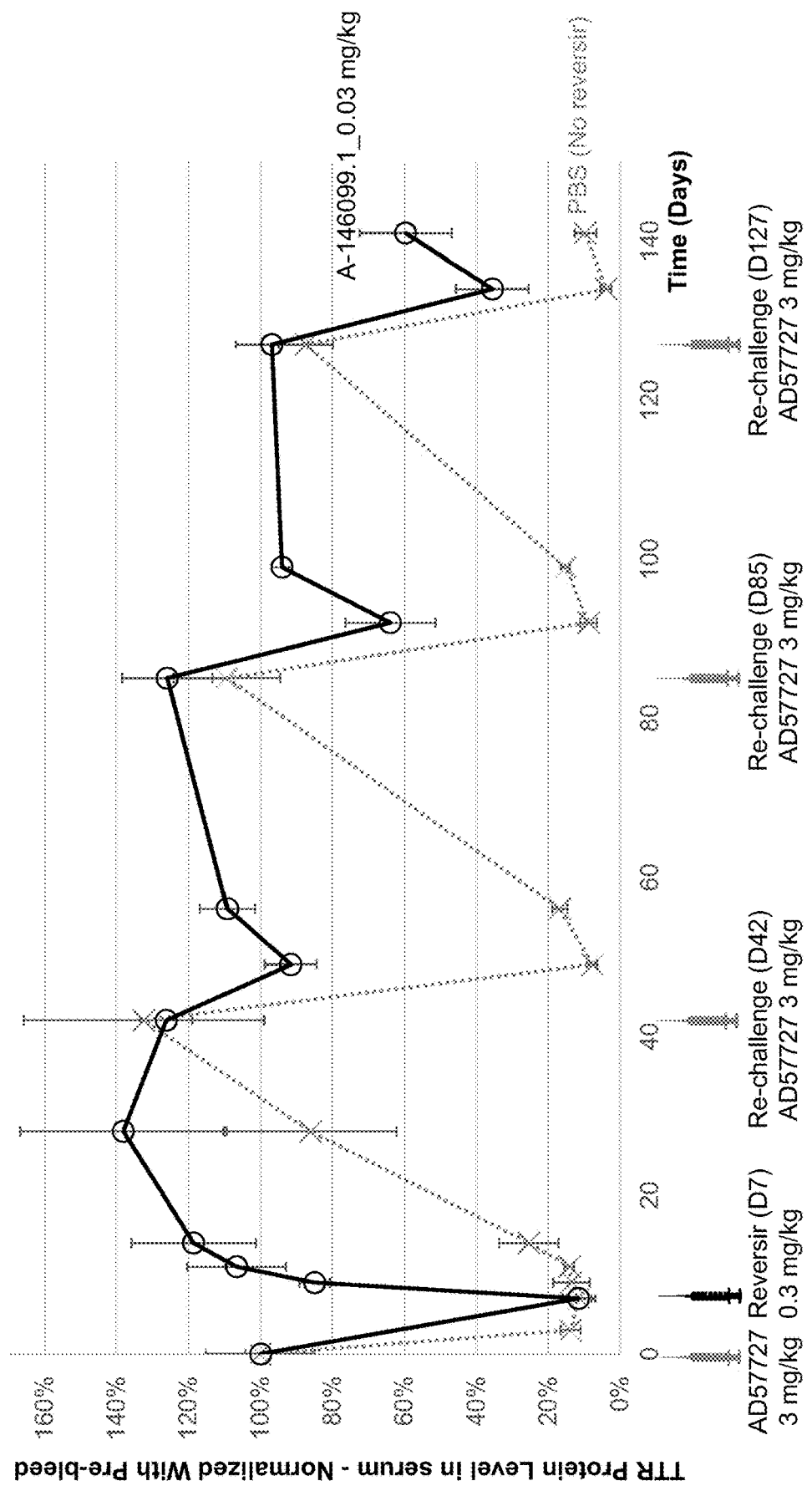
FIG. 4 shows in vivo activity of an exemplary REVERSIR™ compound with long duration of RNAi activity reversal against multiple re-challenging of the TTR-siRNA agent.

Example 6: REVERSIR™ Agent with 5 LNAs Exhibits High Duration of Target Reversal Action in Mice Even after Multiple Re-Challenges with an siRNA-GalNAc Conjugate TTR-siRNA-GalNAc conjugate (AD-57727) was subcutaneously (SC) administered in wild type mice on Day 0 at a dose of 3 mg/kg, followed by SC administration of the 5 LNA, 8 PS 9-mer REVERSIR™ molecule (A-146099.1) at a dose of 0.3 mg/kg on Day 7. Following REVERSIR™ administration, serum bleeds were collected on Days 9, 11, 14, 28 and 42. The TTR protein levels were analyzed and are plotted in FIG. 4 showing full recovery to baseline TTR levels of the REVERSIR™ group by Day 11 and of the no REVERSIR™ PBS group by Day 42. At Day 42, the TTR-siRNA-GalNAc conjugate (AD-57727) was re-challenged with a SC dose of 3 mg/kg, and serum bleeds were collected on Days 49, 56 and 85. After the re-challenging on Day 42, the REVERSIR™ group showed no significant change from the baseline levels of TTR in serum, whereas the no REVERSIR™ PBS group demonstrated full knock-down of TTR levels by Day 49. A second re-challenge with 3 mg/kg of AD-57727 was attempted on Day 85, and serum bleeds were collected on Days 92, 98 and 127. Following the Day 85 AD-57727 dosing, the TTR levels in the REVERSIR™ group were reduced from baseline (100%) to 70% by Day 92, but quickly recovered back to baseline by Day 98, while the PBS group exhibited the full cycle of TTR knock-down and recovery by Day 127 (FIG. 4). Finally, a third re-challenge was attempted on Day 127 with 3 mg/kg of AD-57727, and serum bleeds were collected on Days 134 and 141. Following the Day 127 AD-57727 dosing, the TTR levels in the REVERSIR™ group were further reduced from baseline (100%) to 40% on Day 134, but again quickly recovered back to baseline by Day 141, relative to the no REVERSIR™ PBS control group (FIG. 4). This experiment demonstrated that high content of LNA (5 LNA) and high PS content (8 PS) in REVERSIR™ compounds entails high potency of reversal combined with extreme duration of activity (at 0.3 mg/kg REVERSIR™ dose) with stable baseline TTR levels in mice serum, for up to 120 Days, which cannot be effectively re-dosed and re-challenged with the siRNA agent, even after multiple re-administrations of the siRNA agent at a higher 3 mg/kg dose (FIG. 4).

Figure 5:
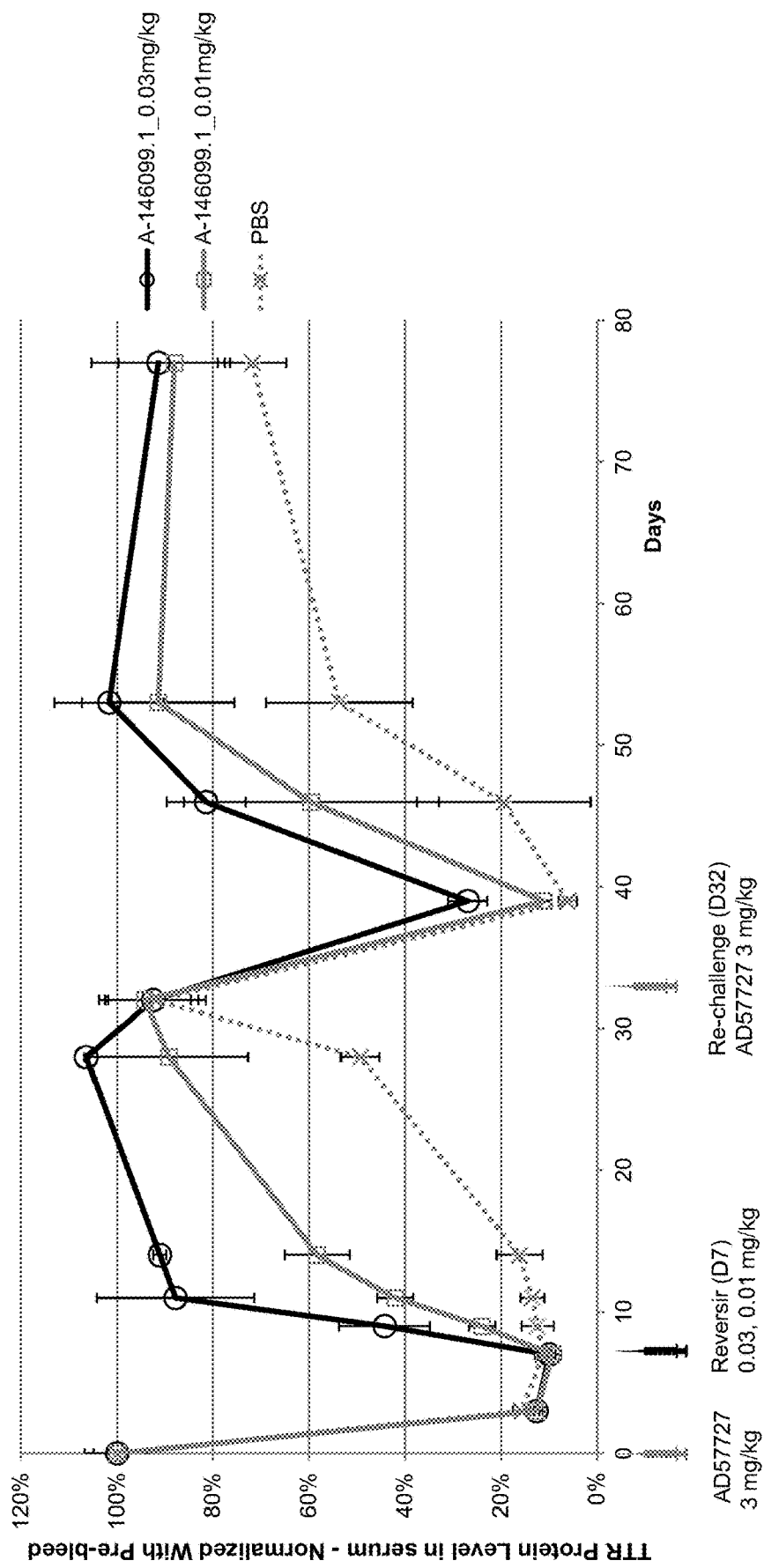
FIG. 5 shows in vivo activity at different doses of an exemplary REVERSIR™ compound with long duration of RNAi activity reversal against single re-challenging of the TTR-siRNA agent.

Example 7: REVERSIR™ Agent with 5 LNAs Exhibits High Duration of Target Reversal Action in Mice Even at Lower Doses of REVERSIR™ Demonstrating that Tunable Duration of REVERSIR™ Cannot be Controlled by Tuning the REVERSIR™ Dose Only TTR-siRNA-GalNAc conjugate (AD-57727) was subcutaneously (SC) administered in wild type mice on Day 0 at a dose of 3 mg/kg, followed by SC administration of the 5 LNA, 8 PS 9-mer REVERSIR™ molecule (A-146099.1) at two doses of 0.03 and 0.01 mg/kg on Day 7. Following the REVERSIR™ administration, serum bleeds were collected on Days 9, 11, 14, 28 and 32. The TTR protein levels were analyzed and are plotted in FIG. 5, showing by Day 11 a full recovery (100%) to baseline TTR levels for the REVERSIR™ group dosed at 0.03 mg/kg and a incomplete, partial (40%) recovery of TTR levels for the REVERSIR™ group dosed at 0.01 mg/kg. On Day 32, the TTR-siRNA-GalNAc conjugate (AD-57727) was re-challenged with a single SC dose of 3 mg/kg, and serum bleeds were collected on Days 39, 46 and 75. After the re-challenging on Day 32, the two-doses tunable REVERSIR™ groups showed reduction (to 40-20%) from the baseline levels of TTR in serum, but quickly recovered back to baseline by Day 46, relative to the no REVERSIR™ PBS control group (FIG. 5). This experiment demonstrated that high content of LNA (5 LNA) and high PS content (8 PS) in REVERSIR™ dosed at a dose of 0.03 mg/kg entails high potency of reversal combined with high duration of activity which was partially re-challenged with the siRNA agent but showed recovery significantly faster than that of the PBS control group (FIG. 5). In addition, the rechallenging profile for the same REVERSIR™ compound, dosed at 0.01 mg/kg showed the similar recovery profile with again quicker recovery of target levels, while showing significantly lower potency of reversal on Days 11 (40%) and 14 (60%), relative to the 0.03 mg/kg REVERSIR™ dose group (100% by Day 11). This experiment showed that dose alone cannot control tunable duration and effective re-challenging of high LNA and high PS content non-tunable REVERSIR™ compounds.

Figure 6:
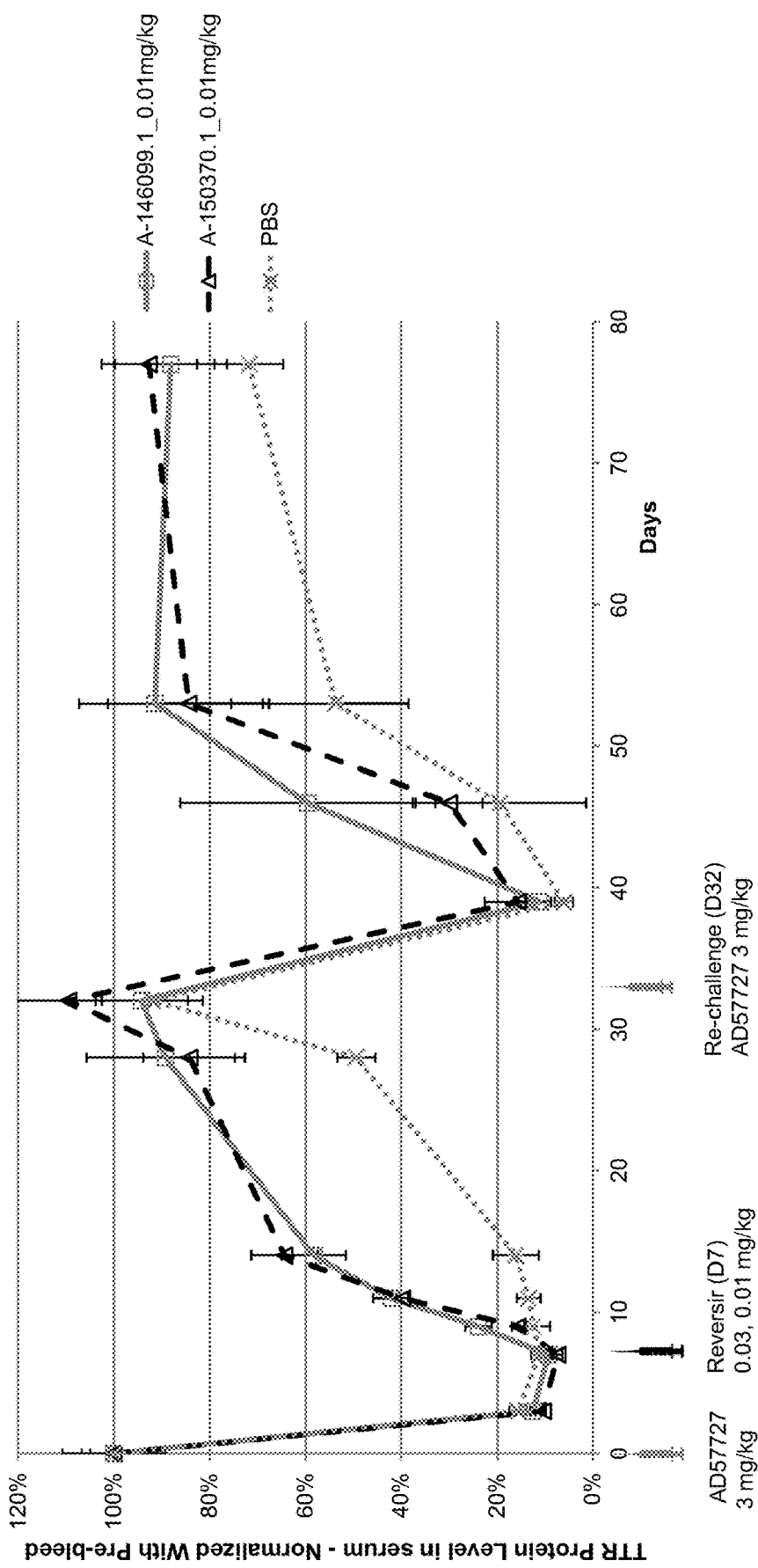
FIG. 6 shows in vivo activity of exemplary REVERSIR™ compounds with long duration of RNAi activity reversal against single re-challenging of the TTR-siRNA agent.

Example 8: Low Dose REVERSIR™ Agent with 5 LNAs Exhibits Partial Reversal of Target Protein Levels Combined with High Duration of Target Reversal Action in Mice Even when Reducing the Number of PS Backbone in REVERSIR™, Demonstrating that Tunable Duration of REVERSIR™ Cannot be Controlled by Tuning the REVERSIR™ Dose and PS Content Only TTR-siRNA-GalNAc conjugate (AD-57727) was subcutaneously (SC) administered in wild type mice on Day 0 at a dose of 3 mg/kg, followed by SC administration of the 5 LNA, 8 PS 9-mer REVERSIR™ molecule (A-146099.1) and the 5 LNA, 4 PS 9-mer REVERSIR™ molecule (A-150370.1), both dosed at the lower dose of 0.01 mg/kg on Day 7. Following the REVERSIR™ administration, serum bleeds were collected on Days 9, 11, 14, 28 and 32. The TTR protein levels were analyzed and are plotted in FIG. 6, showing for both compounds by Day 11 an incomplete partial recovery (40%) of TTR levels for the REVERSIR™ group relative to the no REVERSIR™ PBS control group. On Day 32, the TTR-siRNA-GalNAc conjugate (AD-57727) was re-challenged with a single SC dose of 3 mg/kg, and serum bleeds were collected on Days 39, 46 and 75. After the re-challenging on Day 32, the two REVERSIR™ groups showed reduction (to 20%) from the baseline levels of TTR in serum, comparable to the PBS control group, but again quickly recovered back to baseline by Day 52, relative to the no REVERSIR™ PBS control group which remained at around 50% (FIG. 6). This experiment demonstrated that high content of LNA (5 LNA) and high PS content (8 PS, A-146099.1) in non-tunable REVERSIR™ dosed at a lower dose of 0.01 mg/kg entails partial potency of reversal combined with high duration of activity which was partially re-challenged with the siRNA agent but showed recovery significantly faster than the PBS control group (FIG. 6). In addition, similar profiles of onset reversal and duration and re-challenging were observed when the content of PS modifications was reduced from 8 PS to 4 PS (A-150370.1). This experiment showed that dose alone cannot control tunable duration and effective re-challenging of high LNA non-tunable REVERSIR™ compounds even when the PS content is reduced by half (8 PS to 4 PS).

Figure 7:
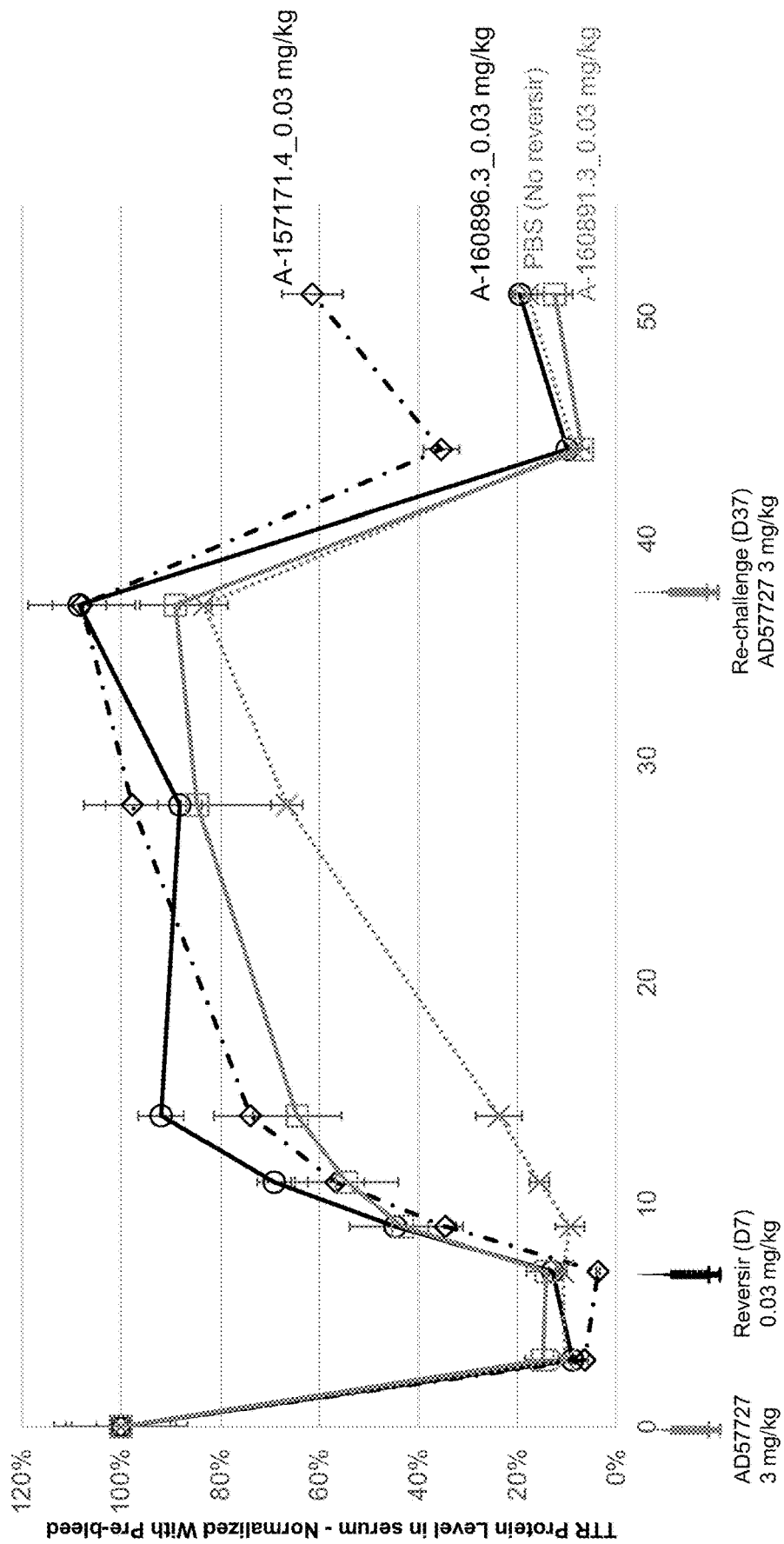
FIG. 7 shows in vivo activity of exemplary tunable REVERSIR™ compounds with tunable duration of RNAi activity reversal against single re-challenging of the TTR-siRNA agent.

Example 9: Example of Control with Tunable REVERSIR™ Designs. Reduction of LNA with Correct LNA Positioning in Tunable REVERSIR™ Agent Exhibits Potent Reversal of Target Protein Levels Combined with Tunable Duration of Target Reversal Action in Mice TTR-siRNA-GalNAc conjugate (AD-57727) was subcutaneously (SC) administered in wild type mice on Day 0 at a dose of 3 mg/kg, followed by SC administration of the 2 LNA, 4 PS 9-mer tunable REVERSIR™ molecule (A-160891.1), the 5 LNA, 4 PS 9-mer tunable REVERSIR™ molecule (A-150370.1) and the 4 LNA, 3 PS, 9-mer tunable REVERSIR™ molecule (A-160896.1) all three dosed at the effective tunable REVERSIR™ dose of 0.03 mg/kg on Day 7. Following the tunable REVERSIR™ administration, serum bleeds were collected on Days 9, 11, 14, 28 and 37. The TTR protein levels were analyzed and are plotted in FIG. 7, showing for both the 5 LNA and the 2 LNA compounds by Day 11 an incomplete partial recovery (50%), and for the 4 LNA compound higher level of recovery (70%) of TTR levels for the tunable REVERSIR™ group relative to the no REVERSIR™ PBS control group. The three groups were even further differentiated on Day 14, where the 4-LNA compound showed the strongest reversal potency. On Day 37, the TTR-siRNA-GalNAc conjugate (AD-57727) was re-challenged with a single SC dose of 3 mg/kg, and serum bleeds were collected on Days 44 and 51 (FIG. 7). After the re-challenging on Day 37, the 5-LNA tunable REVERSIR™ group showed reduction (to 40%) of levels of TTR in serum relative to the PBS control group, but again quickly recovered back to almost baseline by Day 51. Interestingly, both the 2-LNA and the 4-LNA highly tunable REVERSIR™ agents showed re-challenge profiles identical to that of the no tunable REVERSIR™ PBS control group (FIG. 7), with identical levels of TTR on Days 44 and 51. This experiment showed that reduction of LNAs can control tunable duration and effective re-challenging of tunable REVERSIR™ compounds in mice.

Figure 8:
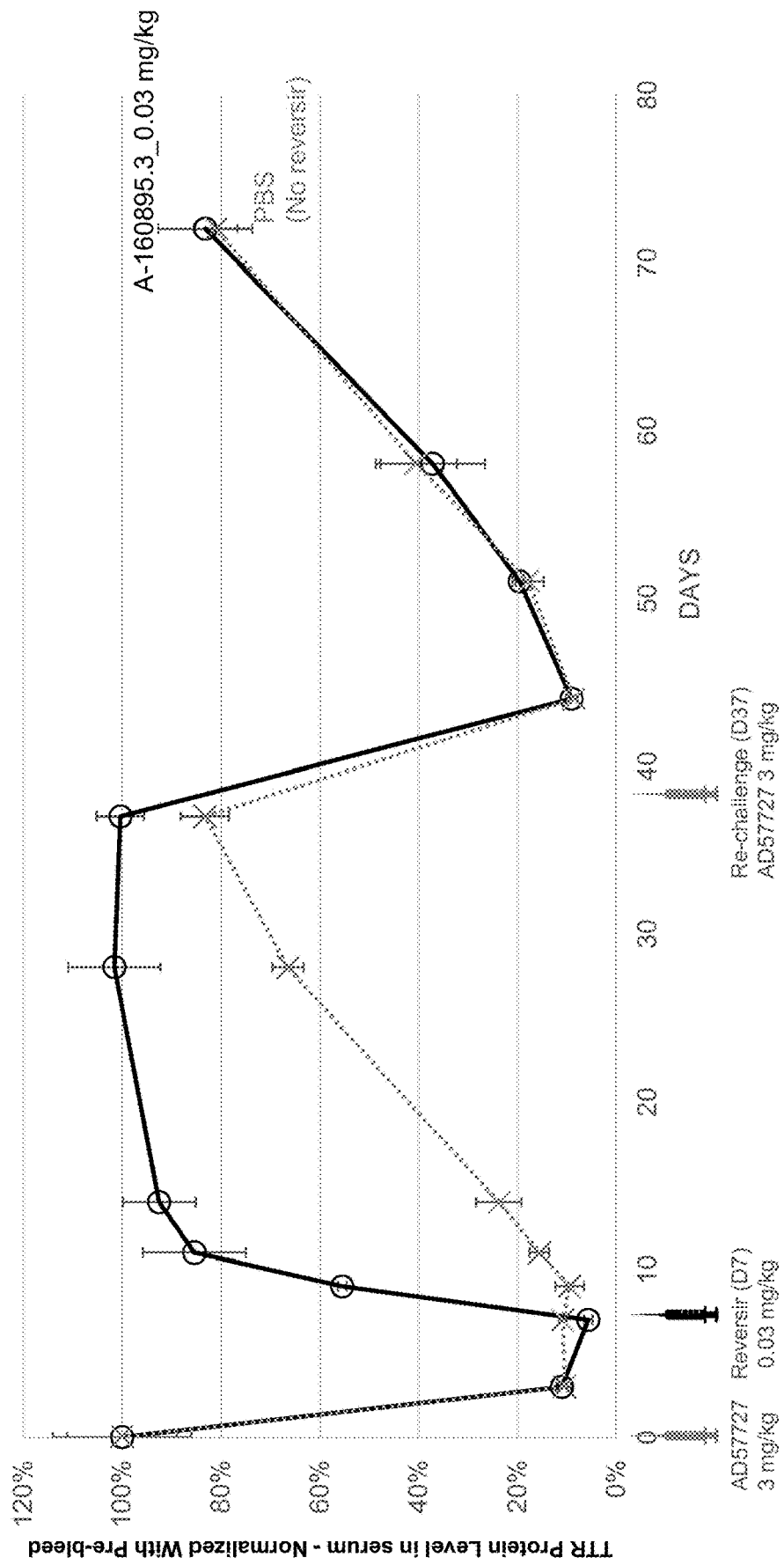
FIG. 8 shows in vivo activity of an exemplary tunable REVERSIR™ compound with tunable duration of RNAi activity reversal against single re-challenging of the TTR-siRNA agent and subsequent complete recovery of RNAi activity.

Example 10: Example of Tunable REVERSIR™ Design with Optimal Tunable Control Over siRNA Activity. 3 LNA Modifications with Correct LNA Positioning Provides Optimal Tunable REVERSIR™ Agent with Tunable Duration of Target Reversal Action in Mice TTR-siRNA-GalNAc conjugate (AD-57727) was subcutaneously (SC) administered in wild type mice on Day 0 at a dose of 3 mg/kg, followed by SC administration of a 3 LNA, 3 PS 9-mer tunable REVERSIR™ molecule (A-160895.1) dosed at the effective tunable REVERSIR™ dose of 0.03 mg/kg on Day 7. Following the tunable REVERSIR™ administration, serum bleeds were collected on Days 9, 11, 14, 28 and 37. The TTR protein levels were analyzed and are plotted in FIG. 8, showing by Day 11 a complete recovery TTR levels for the tunable REVERSIR™ group relative to the no REVERSIR™ PBS control group. On Day 37, the TTR-siRNA-GalNAc conjugate (AD-57727) was re-challenged with a single SC dose of 3 mg/kg, and serum bleeds were collected on Days 44, 51, 58 and 72 (FIG. 8). After the re-challenging on Day 37, the tunable REVERSIR™ group showed showed re-challenge and recovery profiles identical to that of the no REVERSIR™ PBS control group (FIG. 8), with identical levels of TTR on all Days.

Example 11: Phase 1/2a AGT Clinical Design: Increase Confidence in Resistant HTN PoC by Using within-Patient Comparison (Tunable REVERSIR™ Crossover)

Figure 9:
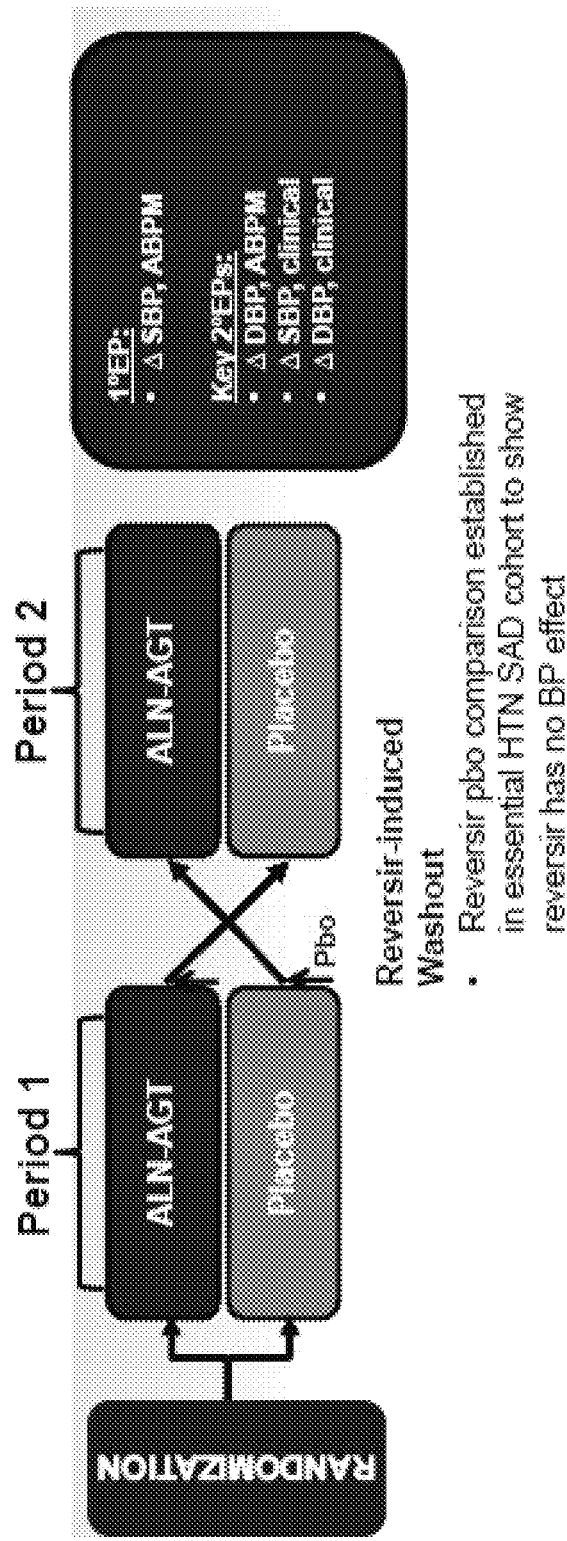
FIG. 9 shows a tunable REVERSIR™ cross-over clinical study design for Phase 1/2a FIG. 10 shows a tunable REVERSIR™ randomized withdrawal clinical study design for Phase 2/3.

The population comprises resistant hypertension as defined by JNC 8 guidelines. About twenty-four patients are used in this phase 1/2 a clinical design (N~24). In sequence 1: ALN-AGT; tunable REVERSIR™ washout; placebo. In sequence 2: Placebo; tunable REVERSIR™ washout; ALN- AGT. The primary endpoint is the change in SBP, ABPM; and the key secondary endpoints are change in DBP, ABPM; change in SBP and clinical; and change in DBP and clinical. The tunable REVERSIR™ pbo comparison established in essential HTN single ascending dose (SAD) cohort to show that tunable REVERSIR™ has no BP effect (FIG. 9).

Example 12: Phase 2/3: Durable Efficacy and Safety: Acceleration by Starting One Year Efficacy/Safety as Phase 2 (Tunable REVERSIR™ Randomized Withdrawal)

Figure 10:
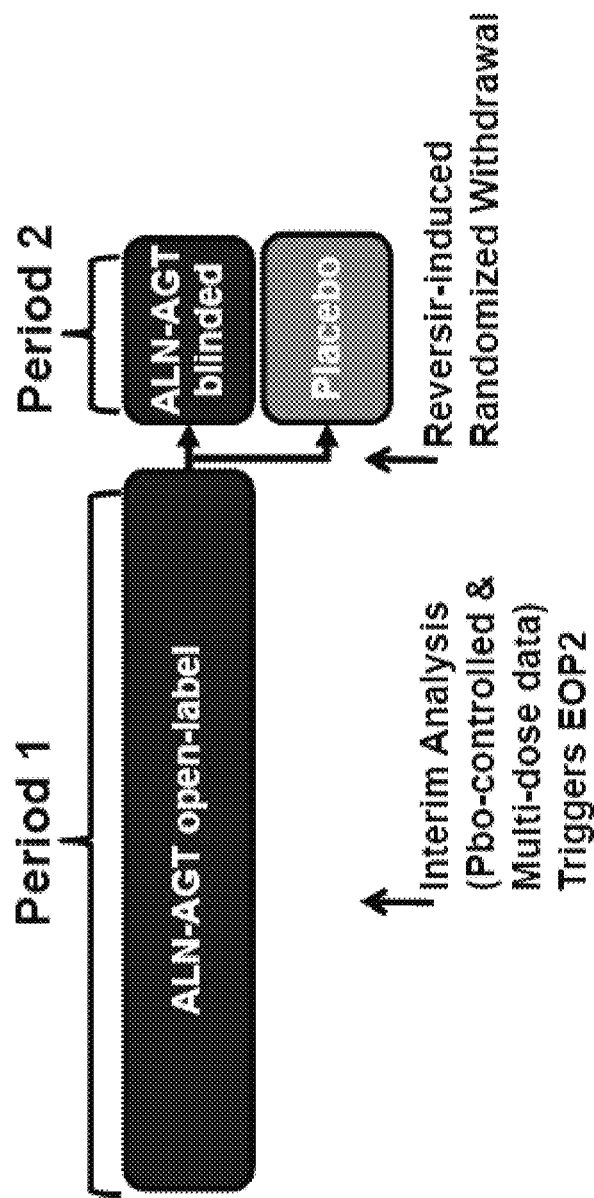
Figure 11:
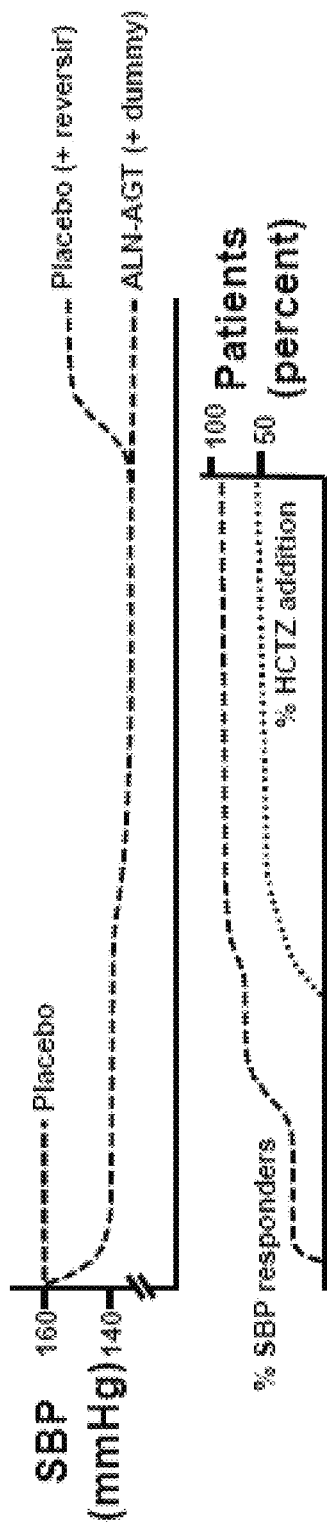
FIG. 11 shows exemplary data expected with a tunable REVERSIR™ randomized withdrawal clinical study design.

The population comprises patients at stage 1 or 2 hypertension (HTN) as defined by JNC 8 guidelines. About one thousand patients are used in this phase 2/3 clinical design (N 1000). In period 1-1 month: randomized double-blind placebo control (DB PC). Period 2-1 year: open-label single-arm; addition of thiazide diuretic if BP not at goal. Period 3: Double-blind placebo control DD randomized withdrawal (DB PC DD). The primary endpoint is to look at safety and adverse events. The key secondary endpoints are SBP responder; DBP responder; change in SBP and clinical; and change in DBP and clinical (FIG. 10). Example of data that can be obtained is shown in FIG. 11.

Systolic hypertension is defined as an elevated systolic blood pressure (SBP). If the systolic blood pressure is elevated (>140) with a normal (<90) diastolic blood pressure (DBP), it is called "isolated systolic hypertension"; HTN is hypertension; BP is blood pressure; HCTZ (hydrochlorothiazide) is a thiazide diuretic (water pill) that helps prevent your body from absorbing too much salt, which can cause fluid retention; EOP2 is end of Phase 2 in the clinical trial.

Figure 12:
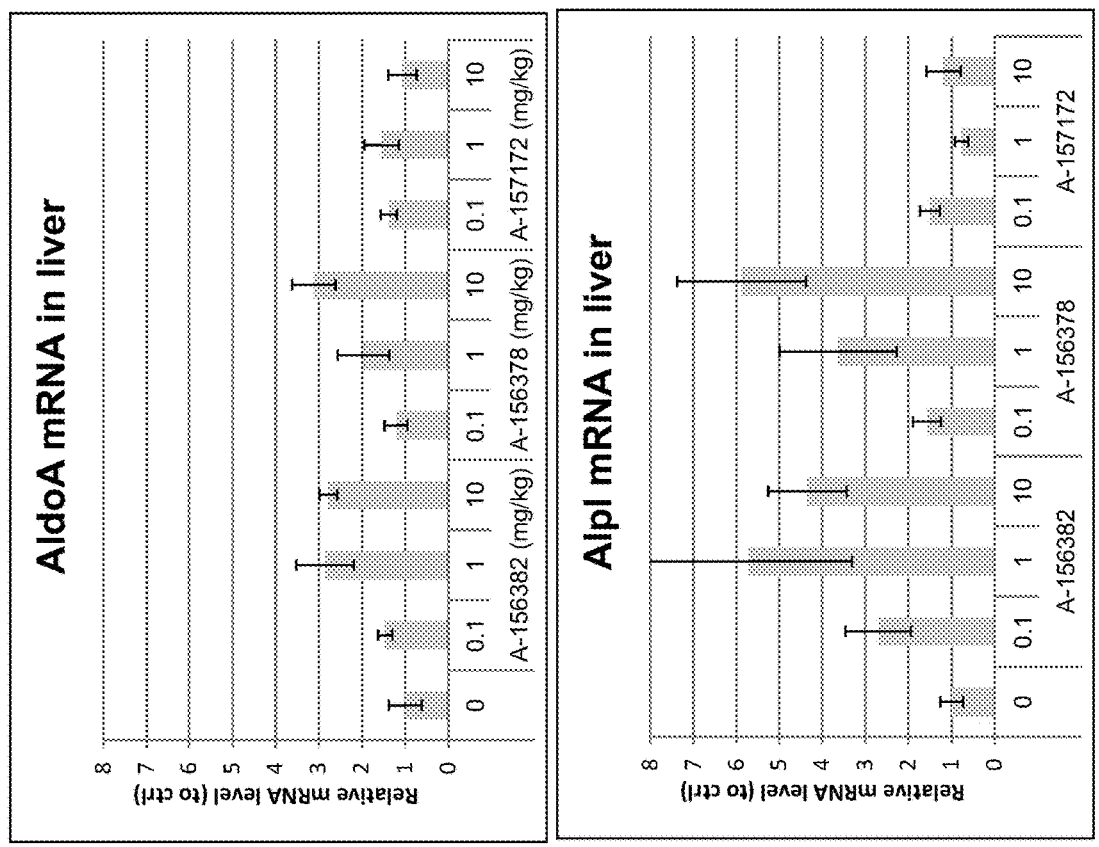
FIG. 12 shows miR-122 Target mRNA Liver qPCR Data from in vivo study in male rats using miR-122 tunable REVERSIR™ compounds.

Example 13: Tunable REVERSIR™ Agents Show miR-122 De-Repression in Rats miR-122 tunable REVERSIR™ compounds were was subcutaneously (SC) administered in wild type male rats on Day 1. Study was terminated at Day 17, livers were collected and the mRNA liver levels of miR-122 target mRNAs (AldoA and Alpl) were measured by qPCR (FIG. 12). The 9-mer miR-122 tunable REVERSIR™ (A-156382) was more potent than the 15-mer (A-156378). Maximum de-repression of miR-122 target mRNAs in the liver was observed at Day 17 with the 1 mg/kg 9-mer A-156382.

Figure 13:
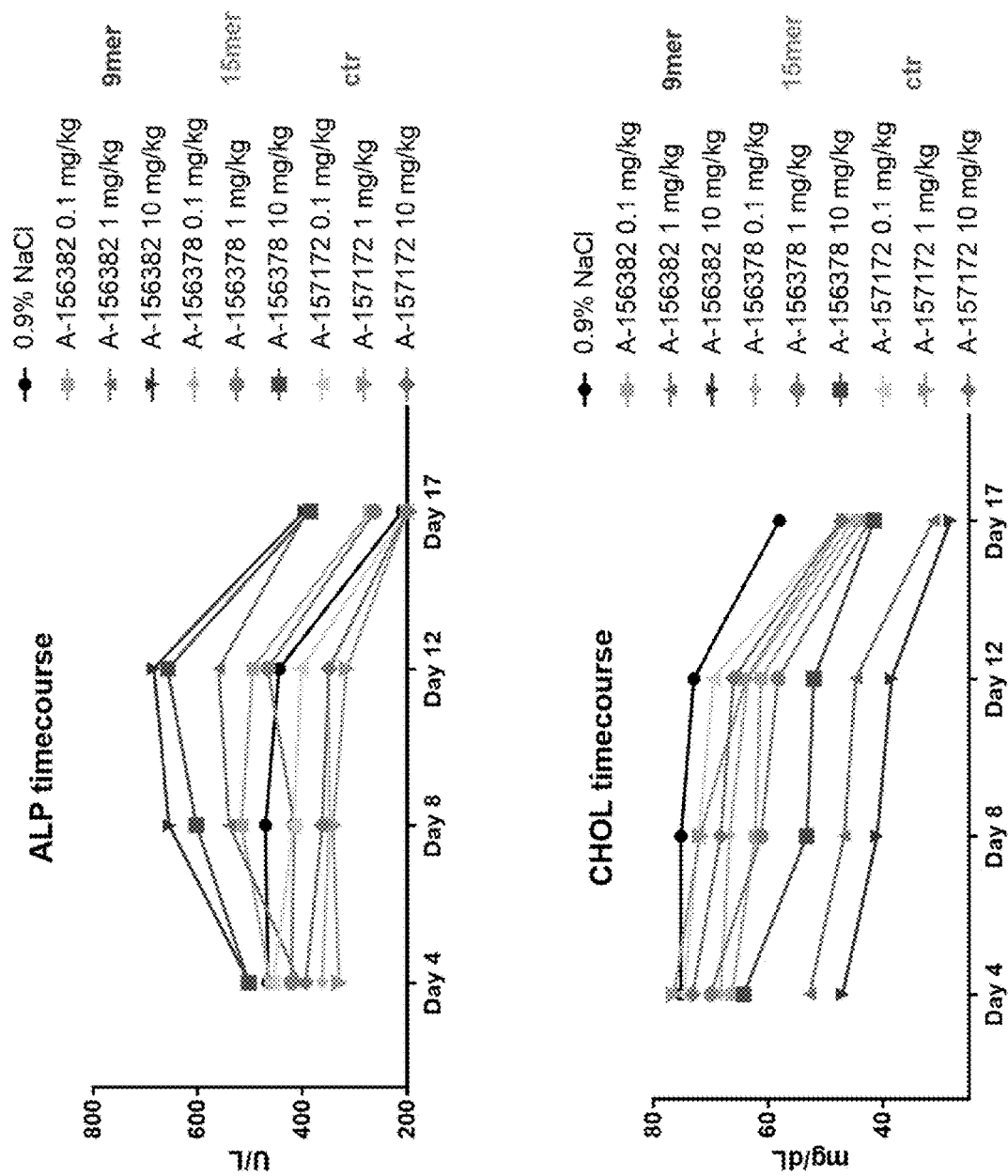
FIG. 13-15 show miR-122 Biomarkers time course from in vivo study in male rats using miR-122 tunable REVERSIR™ compounds.
Figure 14:
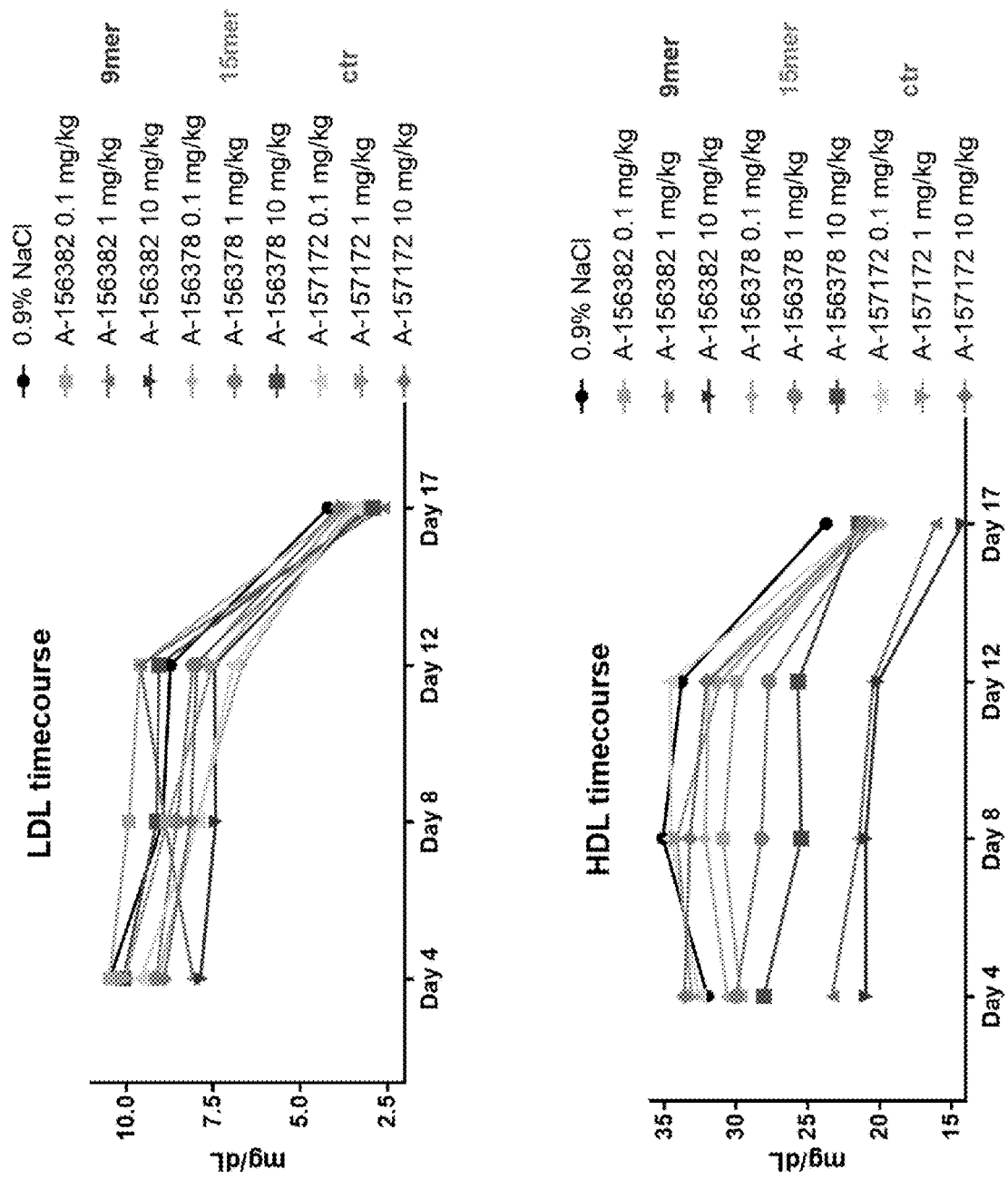
Figure 15:
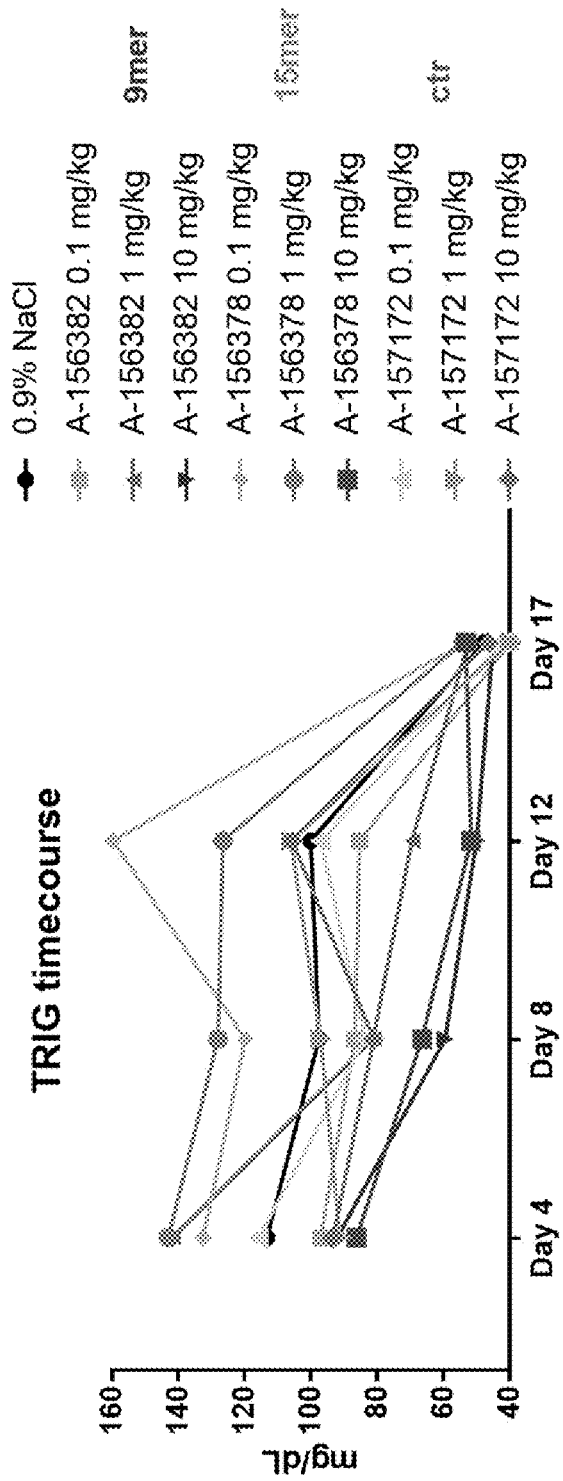
Figure 16:
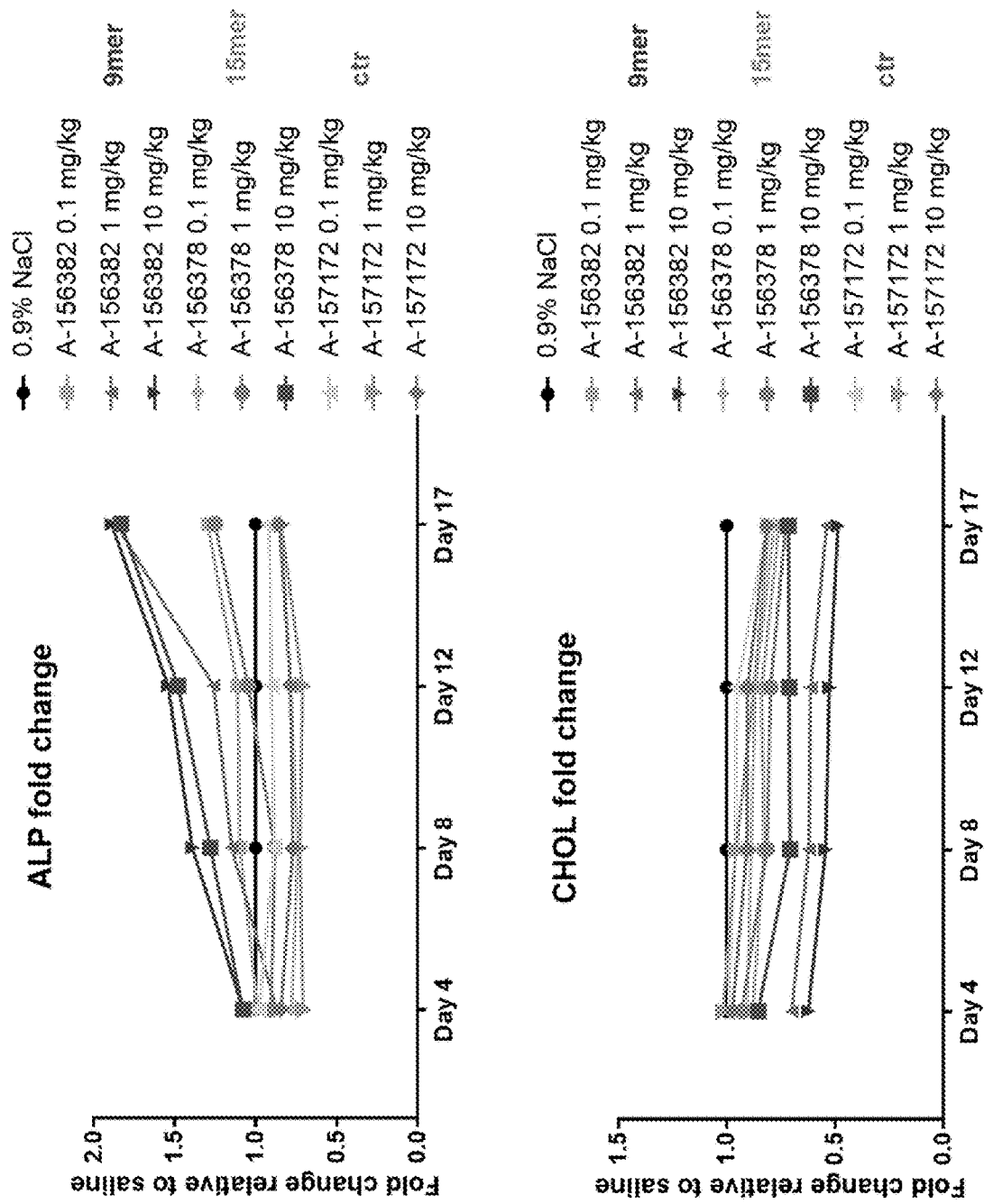
FIG. 16 shows the fold-change of miR-122 Biomarkers relative to saline groups from in vivo study in male rats using miR-122 tunable REVERSIR™ compounds.

Example 14: Tunable REVERSIR™ Agents Show Impact of miR-122 De-Repression on miR-122 Biomarkers in Rats miR-122 tunable REVERSIR™ compounds were was subcutaneously (SC) administered in wild type male rats on Day 1, serum draws were collected on Days 4, 8, 12 (160 uL serum per time point), and at necropsy and time-course of miR-122 biomarkers was measured (FIG. 13-15). The 9-mer miR-122 tunable REVERSIR™ (A-156382) was more potent than the 15-mer (A-156378). Activity-dependent changes with both miR-122 tunable REVERSIR™ compounds was observed (A-156382 and A-156378) but not with the negative control (scrambled sequence) miR-122 tunable REVERSIR™ (A-157172). Similar response to the total CHOL biomarker (FIG. 13) was observed for the HDL biomarker (FIG. 14) where dose-dependent decrease with the 9-mer miR-122 tunable REVERSIR™ A-156382. For the 15-mer A-156378 only a small magnitude of change was observed, whereas for the negative control tunable REVERSIR™ A-157172 the effect on HDL was not dose-dependent (FIG. 14). Subtle tunable REVERSIR™-induced TRIG decrease detected in non-fasted rats only at Day 12 with 10 mg/kg of either mir122 compound (FIG. 15). The fold-changes in ALP and CHOL relative to the saline control groups were determined (FIG. 16) and confirmed that the 9-mer miR-122 tunable REVERSIR™ (A-156382) was more potent than the 15-mer (A-156378).

Figure 17:
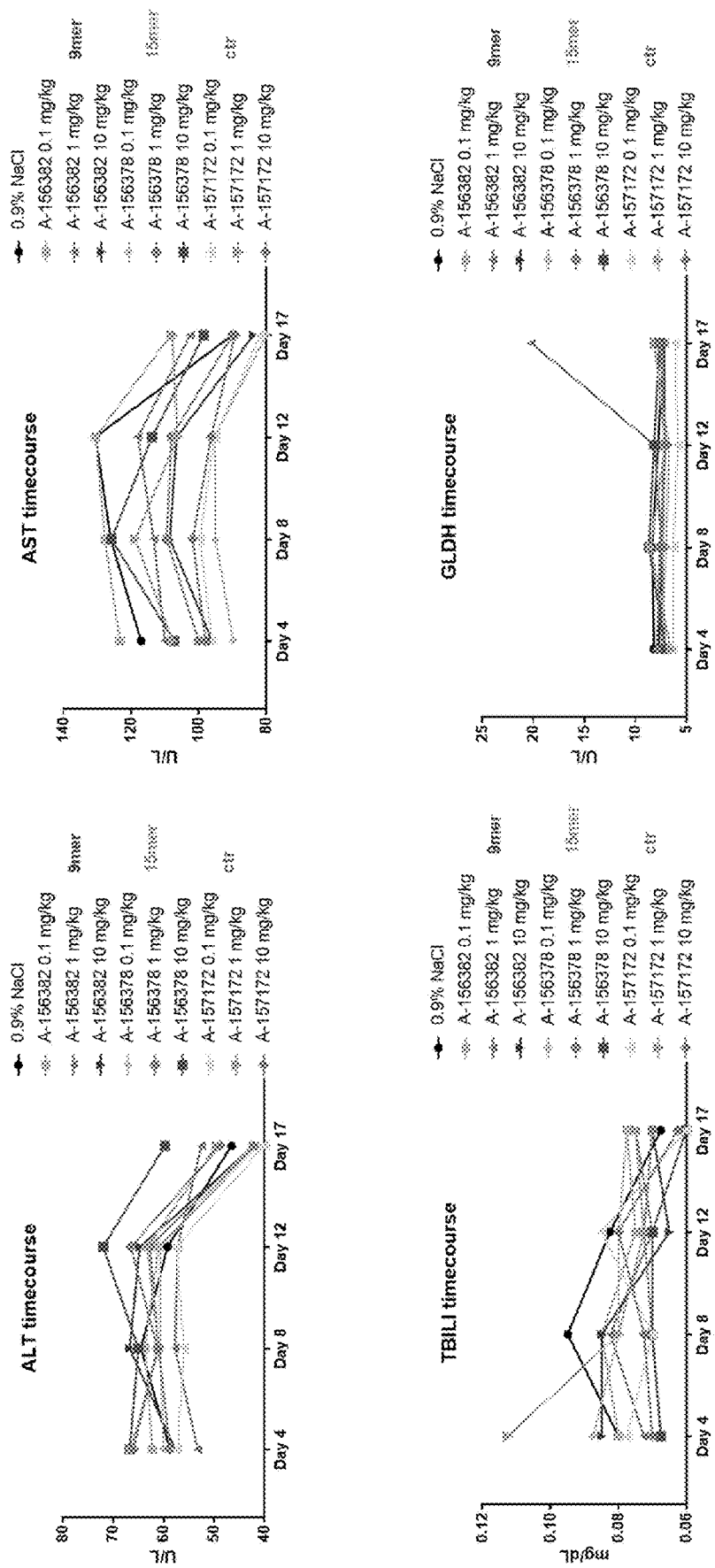
FIG. 17 shows LFT evaluation from in vivo study in male rats using miR-122 tunable REVERSIR™ compounds.
Figure 18:
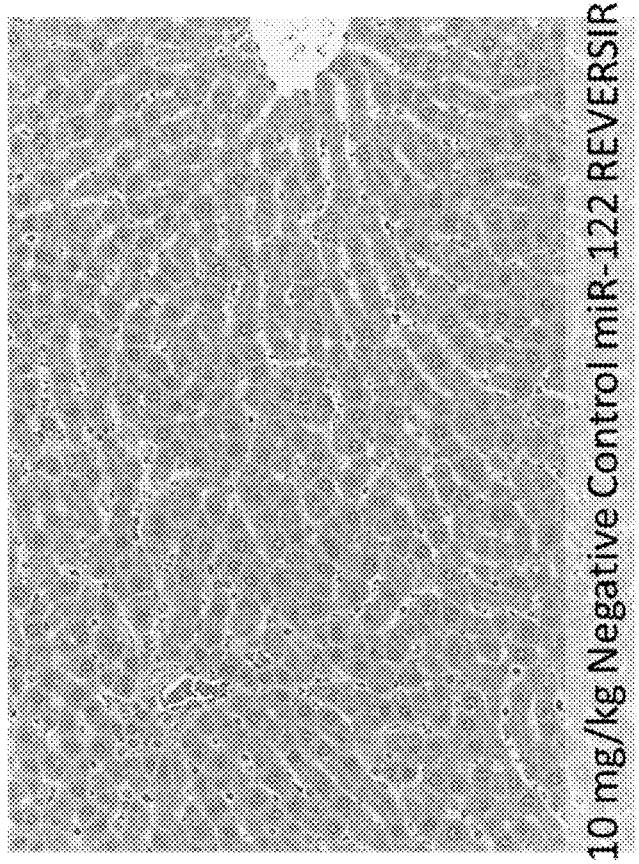
FIG. 18-19 show histopathology data from in vivo study in male rats using miR-122 tunable REVERSIR™ compounds.
Figure 18:
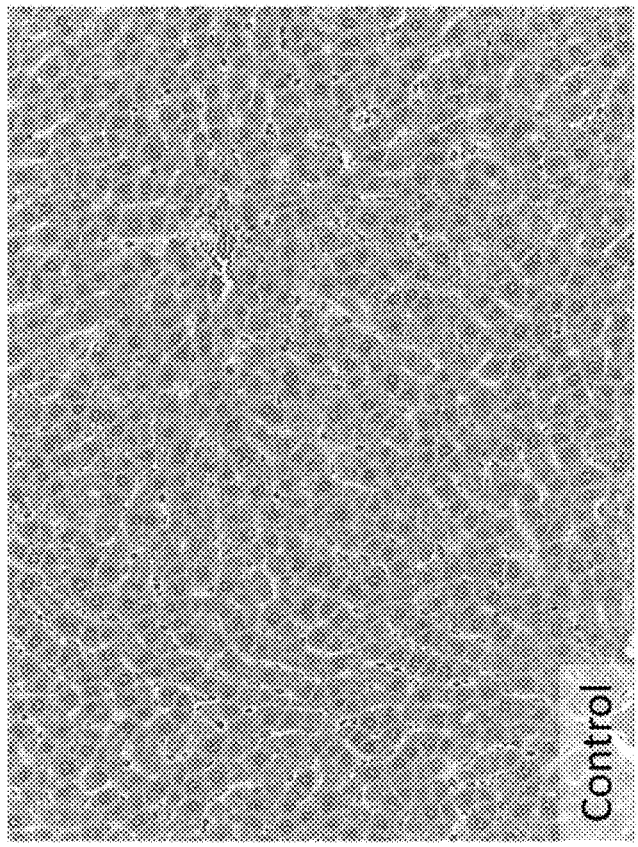
Figure 19:
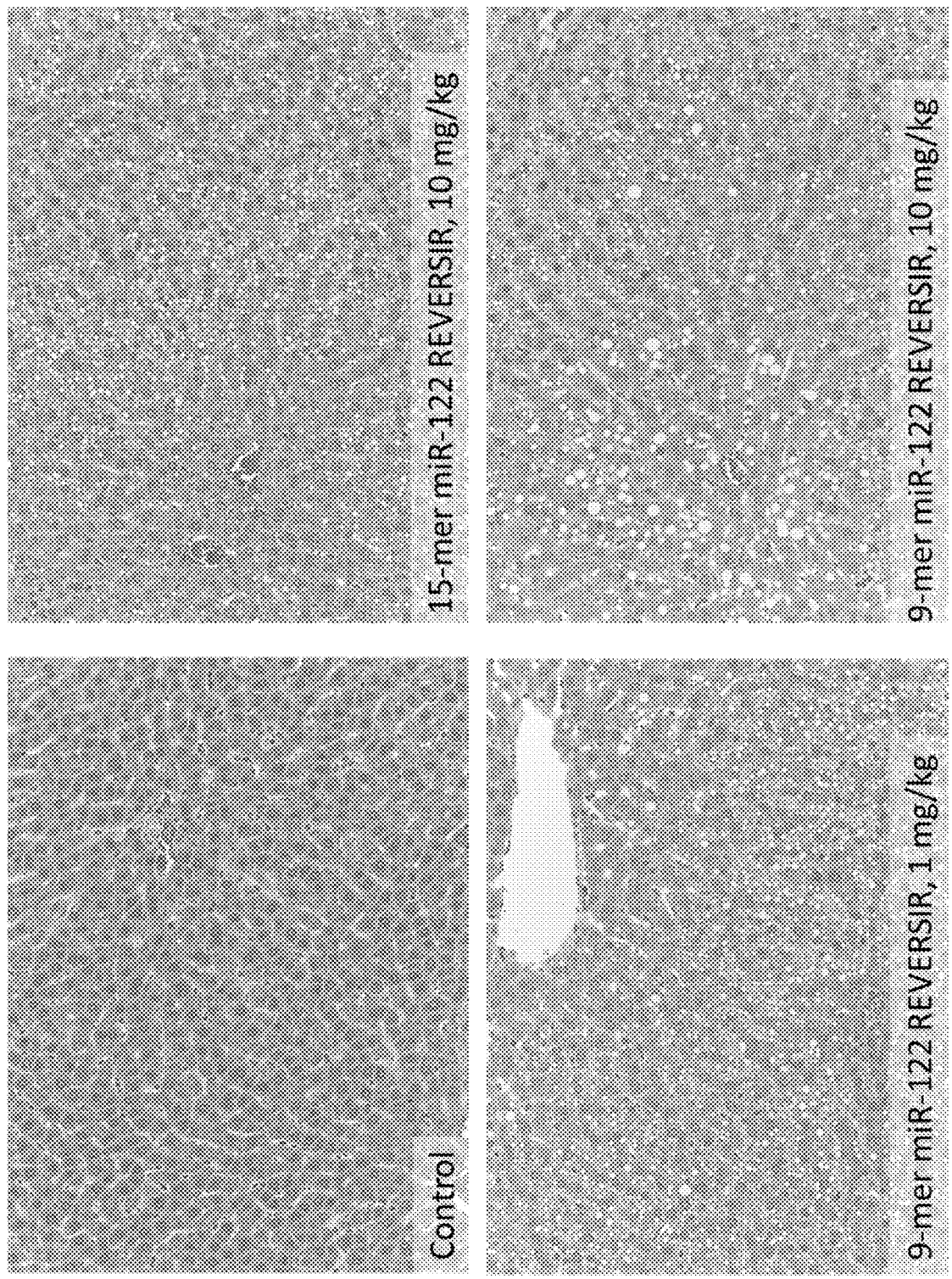

Example 15: No Histologic Evidence of Hepatocellular Toxicity, Normal Liver Parameters on Serum Chemistry were Observed with Tunable REVERSIR™ Agents in miR-122 De-Repression on miR-122 in Rats miR-122 tunable REVERSIR™ compounds were subcutaneously (SC) administered in wild type male rats on Day 1, the study was terminated at Day 17, livers were collected for liver test function (LFT) evaluation (FIG. 17) and histopathology evaluation (FIG. 18-19).

Tables

Table 1 shows exemplary lipid-tunable REVERSIR™ formulations.

Table 2 shows the sequence of the TTR siRNA-GalNAc conjugate agent (AD-57727) used.

Table 3 shows the sequences of the tunable REVERSIR™ agents used. Black circles are 2'-O-methyl nucleotides, Grey circles are LNA nucleotides, Dashed grey circle A is 2'-deoxy adenosine. Bars are PS linkages.

Table 4 shows the sequences of miR-122 tunable REVERSIR™ agents used. Black circles are 2'-O-methyl nucleotides, Grey circles are LNA nucleotides, Dashed grey circle A is 2'-deoxy adenosine. Bars are PS linkages.

Table 5 shows the in vivo study design for evaluation of miR-122 tunable REVERSIR™ agents in rats. Endpoints were as follows: Serum draws on Days 4, 8, 12 (160 uL serum per time point), and at necropsy. Interim miR-122 biomarkers: ↑ALP, ↓CHOL, ↓TRIG, ↓LDL, ↓HDL. Liver injury biomarkers: ALT, GLDH, AST, TBIL. Terminal Full serum chem panel+TBA, HDL, LDL. Liver collection at necropsy and Histopath: qPCR for miR-122 target mRNAs (ALP, AldoA). Northern blot for miR-122.

Abbreviations used in describing the sequences, e.g., sequences described in Table 2 are collected and described in Table 6 for convenience.

TABLE 2

| Duplex Name | Sense target | Sense Oligo | Sense OligoSeq | Antisense Oligo | Antisense OligoSeq |
|---|---|---|---|---|---|
| AD-57727.1 | m/r TTR | A-117799.1 | AfsasCfaGfuGfuUfCfUfuGfcUfcUfaUfaAfL96 | A-117800.1 | usUfsaUfaGfaGfAfagaAfcAfcUfgUfususu |

The Sequence ID's in Table 2 are as follows: A-117799.1 (SEQ ID NO: 36) and A-117800.1 (SEQ ID NO: 37).

TABLE 3

| A-146099.2 | | 8 PS, 5 LNA |
| A-157171.4 | | 5 PS, 5 LNA |
| A150370.4 | | 4 PS, 5 LNA |
| A-160888.3 | | 14 PS, 5 LNA (g6) |
| A-160889.3 | | 14 PS, 5 LNA (Non g6) |
| A-160890.3 | | 7 PS, 2 LNA (g6) |
| A-160891.3 | | 4 PS, 2 LNA (g6) |
| A-160892.3 | | 5 PS, 2 LNA (g6) |
| A-146096.3 | | 5 PS, 2 LNA (Non g6) |
| A160895.3 | | 3 PS, 3 LNA |
| A-160896.3 | | 3 PS, 4 LNA |

The sequence ID's and sequences in Table 3 are as follows:
- A-146099.2 (SEQ ID NO: 38), usgs(m5Clns)(Tlns)(m5Clns)(Tlns)as(Tlns)adAL96;
- A-157171.4 (SEQ ID NO: 39), usgs(m5Cln)us(m5Cln)(Tln)as(Tlns)(Aln)dAL96;
- A-150370.4 (SEQ ID NO: 40), usgs(m5Cln)(Tln)(m5Cln)(Tln)as(Tlns)adAL96;
- A-160888.3 (SEQ ID NO: 41), usgscsus(m5Cln)usa-susadAL96;
- A-160889.3 (SEQ ID NO: 42), usgscu(m5Cln)ua-susadAL96;
- A-160890.3 (SEQ ID NO: 43), usgscsus(m5Cln)usasus(Aln)dAL96;
- A-160891.3 (SEQ ID NO: 44), usgscu(m5Cln)uasus(Aln)dAL96;
- A-160892.3 (SEQ ID NO: 45), usgscsu(m5Cln)uasus(Aln)dAL96;
- A-146093.3 (SEQ ID NO: 46), usgsususcsus(Tlns)gs(m5Clns)(Tlns)(m5Clns)(Tlns)as(Tlns)adAL96;
- A-160895.3 (SEQ ID NO: 47), usgscu(m5Cln)u(Aln)us(Aln)dAL96; and
- A-160896.3 (SEQ ID NO: 48), usgs(m5Cln)u(m5Cln)u(Aln)us(Aln)dAL96. Where: L96 is N-[tris(GalNAc-alkyl)-amidodecanoyl)]-4-hydroxyprolinol Hyp-(GalNAc-alkyl)3; s is phosphorothioate; Nln is LNA; Lower case is 2'-OMe; (m5Cln) is 2'-O,4'-C-methylene 5-methylcytidine-3'-phosphate; and DN is 2'-deoxy.

TABLE 4

TABLE 4-continued

157172     A-157172 (negative control)

[Structure diagram: U C T A T A C G T A with GalNAc, GalNAc, GalNAc branches]

The sequence ID's and sequences in Table 4 are as follows:

A-156382 (SEQ ID NO: 49), (T1 ns)csascs(Aln)(m5C1n)us(m5C1 ns)(m5C1n)dAL96;

A-156378 (SEQ ID NO: 50), cscsasususgs(Tln)csascs(Aln)(m5Clns)us(m5Clns)(m5Cln)dAL96; and A-157172 (SEQ ID NO: 51), uscs(Tln)as(Tln)(Aln)cs(Glns)(Tln)dAL96. Where: L96 is N-[tris(GalNAc-alkyl)-amidodecanoyl)]-4-hydroxyprolinol Hyp-(GalNAc-alkyl)$_3$; s is phosphorothioate; Nln is LNA; Lower case is 2'-OMe; (m5Cln) is 2'-0,4'-C-methylene 5-methylcytidine-3'-phosphate; and DN is 2'-deoxy.

TABLE 5

| Group | Test/Control Article | Dose (mg/Kg) | Concentration (mg/ml) | Route and Regimen | Dose Volume (mL/kg) | Animal Numbers[a] Male | End of Study |
|---|---|---|---|---|---|---|---|
| 1 | 0.9% Nacl | 0 | 0 | SC Day 1 | 5 | 1001-1004 | 17 |
| 2 | A-156382 | 0.1 | 0.02 | | | 2001-2004 | |
| 3 | | 1 | 0.2 | | | 3001-3004 | |
| 4 | | 10 | 2 | | | 4001-4004 | |
| 5 | A156378 | 0.1 | 0.02 | | | 5001-5004 | |
| 6 | | 1 | 0.2 | | | 6001-6004 | |
| 7 | | 10 | 2 | | | 7001-7004 | |
| 8 | A-157172 | 0.1 | 0.02 | | | 8001-8004 | |
| 9 | (Negative | 1 | 0.2 | | | 9001-9004 | |
| 10 | Control) | 10 | 2 | | | 10001-10004 | |

TABLE 6

Abbreviations of nucleotide monomers used in nucleic acid sequence representation.

| Abbreviation | Nucleotide(s) |
|---|---|
| A | Adenosine-3'-phosphate |
| Ab | beta-L-adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |
| (A3m) | 3'-O-methyladenosine-2'-phosphate |
| (A3mx) | 3'-O-methyl-xylofuranosyladenosine-2'-phosphate |
| (G3m) | 3'-O-methylguanosine-2'-phosphate |
| (G3mx) | 3'-O-methyl-xylofuranosylguanosine-2'-phosphate |
| (C3m) | 3'-O-methylcytidine-2'-phosphate |
| (C3mx) | 3'-O-methyl-xylofuranosylcytidine-2'-phosphate |
| (U3m) | 3'-O-methyluridine-2'-phosphate |
| (U3mx) | 3'-O-methylxylouridine-2'-phosphate |
| (Chd) | 2'-O-hexadecyl-cytidine-3'-phosphate |
| (pshe) | Hydroxy ethylphosphorothioate |
| (Uhd) | 2'-O-hexadecyl-uridine-3'-phosphate |
| (Tgn) | Thymidine-glycol nucleic acid (GNA) S-Isomer |
| (Cgn) | Cytidine-glycol nucleic acid (GNA) |
| (Chd) | 2'-O-hexadecyl-cytidine-3'-phosphate |
| (Ggn) | 2'-O-hexadecyl-cytidine-3'-phosphate |

TABLE 6-continued

Abbreviations of nucleotide monomers used in nucleic acid sequence representation.

| Abbreviation | Nucleotide(s) |
|---|---|
| (Agn) | Adenosine-glycol nucleic acid (GNA) |
| P | 5'-phosphate |
| (m5Cam) | 2'-O-(N-methylacetamide)-5-methylcytidine-3'-phosphate |
| (m5Cams) | 2'-O-(N-methylacetamide)-5-methylcytidine-3'-phosphorothioate |
| (Tam) | 2'-O-(N-methylacetamide)thymidine-3'-phosphate |
| (Tams) | 2'-O-(N-methylacetamide)thymidine-3'-phosphorothioate |
| (Aam) | 2'-O-(N-methylacetamide)adenosine-3'-phosphate |
| (Aams) | 2'-O-(N-methylacetamide)adenosine-3'-phosphorothioate |
| (Gam) | 2'-O-(N-methylacetamide)guanosine-3'-phosphate |
| (Gams) | 2'-O-(N-methylacetamide)guanosine-3'-phosphorothioate |
| Y44 | 2-hydroxymethyl-tetrahydrofurane-5-phosphate |
| Q173 | N-((GalNAc)-amidopentanoyl)-prolinol-4-phosphate (Hyp-C5-(GalNAc)) |

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A modified oligonucleotide comprising 8-15 linked nucleotides, wherein at most only three of the nucleotides are high affinity monomers, and wherein the modified oligonucleotide comprises a nucleotide sequence substantially complementary to positions 2-8 of an antisense strand of an siRNA, and one of the high affinity monomers in the modified oligonucleotide is base paired with the 6th nucleotide from the 5'-end of the antisense strand of the siRNA.

2. The modified oligonucleotide of claim 1, wherein the high affinity monomer is an LNA.

3. The modified oligonucleotide of claim 2, wherein the modified oligonucleotide comprises three LNA nucleotides.

4. The modified oligonucleotide of claim 1, wherein the modified oligonucleotide is a single-stranded oligonucleotide that is at least 90% complementary to the antisense strand.

5. The modified oligonucleotide of claim 1, wherein the modified oligonucleotide is fully complementary to the antisense strand.

6. The modified oligonucleotide of claim 1, wherein the modified oligonucleotide comprises at least one modified internucleotide linkage.

7. The modified oligonucleotide of claim 6, wherein internucleotide linkage is a phosphorothioate.

8. The modified oligonucleotide of claim 7, wherein the modified oligonucleotide comprises not more than three or four phosphorothioate modifications.

9. The modified oligonucleotide of claim 1, wherein the modified oligonucleotide is conjugated with a ligand.

10. The modified oligonucleotide of claim 9, wherein the ligand is

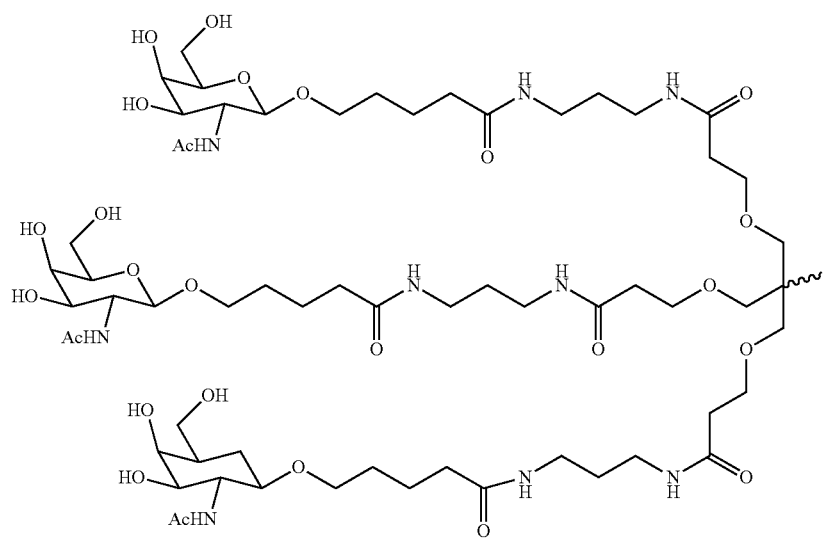

11. The modified oligonucleotide of claim 9, wherein the ligand is conjugated to 3'-terminus of the compound.

12. The modified oligonucleotide of claim 1, wherein the modified oligonucleotide is conjugated with a ligand and the ligand is conjugated to a nucleotide with a deoxy sugar in the modified oligonucleotide.

13. The modified oligonucleotide of claim 12, wherein said deoxy sugar is a 2'-deoxy ribose.

14. The modified oligonucleotide of claim 1, wherein the modified oligonucleotide comprises 9, 10 or 11 linked nucleotides.

15. The modified oligonucleotide of claim 1, wherein only two of the nucleotides are high affinity monomers.

16. A kit comprising a modified oligonucleotide of claim 1.

17. The kit of claim 16, wherein the kit further comprises a siRNA.

18. A method or a system for assessing the efficacy and safety of a pharmaceutical composition for use in the treatment or prophylaxis of a disease, the method comprising the steps of:
    (1) treating all subjects with the pharmaceutical composition for a first treatment time frame,
    (2) deriving mRNA level and/or physiological outcome measures for the all subjects,
    (3) separating the responder members of the treated subjects from the non-responder members,
    (4) randomizing and stratifying members of the responders into at least two further sub-groups,
    (5) continue treating members of one sub-group in (4) with the pharmaceutical composition, and treating members of the other sub-group with a modified oligonucleotide of claim 1 for a second treatment timeframe,
    (6) deriving mRNA level and/or physiological outcome measures for the sub-groups,
    (7) comparing the outcomes at (6) with the outcomes at (2),
    (8) using the comparison in (7) to derive an efficacy and safety measures for the pharmaceutical composition wherein the pharmaceutical composition is an oligonucleotide.

19. A method or a system for assessing the efficacy and safety of a pharmaceutical composition for use in the treatment or prophylaxis of a disease, the system comprising the steps of:
    (1) stratifying a subject group into at least two sub-groups,
    (2) treating members of one sub-group with the pharmaceutical composition for a first treatment timeframe, and treating members of a second sub-group with a blinded placebo,
    (3) deriving mRNA level, and/or biomarker and/or physiological outcome measures for the sub-groups,
    (4) treating members of the treated sub-group with a modified oligonucleotide of claim 1, and treating members of the other blinded placebo sub-group with the pharmaceutical composition for a second treatment timeframe,
    (5) deriving mRNA level and/or physiological outcome measures for the sub-groups,
    (6) comparing the outcomes at (5) with the outcomes at (3),
    (7) using the comparison in (6) to derive an efficacy and safety measures for the pharmaceutical composition wherein the pharmaceutical composition is an oligonucleotide.

* * * * *

```
                         SEQUENCE LISTING

<160> NUMBER OF SEQ ID NOS: 54

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Leu Glu Ala Leu Ala Glu Ala Leu Glu Ala Leu Ala Glu Ala
1               5                   10                  15

Leu Glu Ala Leu Ala Glu Ala Ala Ala Gly Gly Cys
            20                  25

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys
            20                  25                  30

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Glu Ala Leu Ala Glu Ala Leu Glu Ala Leu Ala Glu Ala
1               5                   10                  15
```

-continued

```
<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Leu Phe Glu Ala Ile Glu Gly Phe Ile Glu Asn Gly Trp Glu Gly
1               5                   10                  15

Met Ile Trp Asp Tyr Gly
            20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 6
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Leu Phe Glu Ala Ile Glu Gly Phe Ile Glu Asn Gly Trp Glu Gly
1               5                   10                  15

Met Ile Asp Gly Trp Tyr Gly Cys Gly Leu Phe Glu Ala Ile Glu Gly
            20                  25                  30

Phe Ile Glu Asn Gly Trp Glu Gly Met Ile Asp Gly Trp Tyr Gly Cys
        35                  40                  45

<210> SEQ ID NO 7
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
            20                  25                  30

Glu Asn Gly Trp Glu Gly Met Ile Asp Gly Gly Cys
        35                  40

<210> SEQ ID NO 8
<211> LENGTH: 35
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 8

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

<210> SEQ ID NO 10
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Norleucine
<220> FEATURE:
<221> NAME/KEY: MOD_RES
<222> LOCATION: (38)..(38)
<223> OTHER INFORMATION: Norleucine

<400> SEQUENCE: 10

Gly Leu Phe Glu Ala Ile Glu Gly Phe Ile Glu Asn Gly Trp Glu Gly
1               5                   10                  15

Xaa Ile Asp Gly Lys Gly Leu Phe Glu Ala Ile Glu Gly Phe Ile Glu
            20                  25                  30

Asn Gly Trp Glu Gly Xaa Ile Asp Gly
            35                  40

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Phe Glu Ala Leu Leu Glu Leu Leu Glu Ser Leu Trp Glu Leu Leu
1               5                   10                  15

Leu Glu Ala

<210> SEQ ID NO 12

-continued

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Phe Lys Ala Leu Leu Lys Leu Leu Lys Ser Leu Trp Lys Leu
1               5                   10                  15

Leu Leu Lys Ala
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Phe Arg Ala Leu Leu Arg Leu Leu Arg Ser Leu Trp Arg Leu
1               5                   10                  15

Leu Leu Arg Ala
            20

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Phe Phe Glu Ala Ile Ala Glu Phe Ile Glu Gly Gly Trp Glu
1               5                   10                  15

Gly Leu Ile Glu Gly Cys
            20

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ile Gly Ala Val Leu Lys Val Leu Thr Thr Gly Leu Pro Ala Leu
1               5                   10                  15
```

Ile Ser Trp Ile Lys Arg Lys Arg Gln Gln
            20              25

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His His His His His Trp Tyr Gly
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys His Lys Lys Lys Lys Lys Lys His Cys
1               5                   10

<210> SEQ ID NO 19
<211> LENGTH: 16
<212> TYPE: PRT
<213> ORGANISM: Drosophila sp.

<400> SEQUENCE: 19

Arg Gln Ile Lys Ile Trp Phe Gln Asn Arg Arg Met Lys Trp Lys Lys
1               5                   10                  15

<210> SEQ ID NO 20
<211> LENGTH: 14
<212> TYPE: PRT
<213> ORGANISM: Human immunodeficiency virus

<400> SEQUENCE: 20

Gly Arg Lys Lys Arg Arg Gln Arg Arg Arg Pro Pro Gln Cys
1               5                   10

<210> SEQ ID NO 21
<211> LENGTH: 27
<212> TYPE: PRT
<213> ORGANISM: Unknown
<220> FEATURE:
<223> OTHER INFORMATION: Description of Unknown:
      Signal sequence based peptide

<400> SEQUENCE: 21

Gly Ala Leu Phe Leu Gly Trp Leu Gly Ala Ala Gly Ser Thr Met Gly
1               5                   10                  15

Ala Trp Ser Gln Pro Lys Lys Arg Lys Val
            20              25

<210> SEQ ID NO 22
<211> LENGTH: 18
<212> TYPE: PRT
<213> ORGANISM: Mus sp.

<400> SEQUENCE: 22

Leu Leu Ile Ile Leu Arg Arg Arg Ile Arg Lys Gln Ala His Ala His
1               5                   10                  15

Ser Lys

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Leu Ala Leu Lys Leu Ala Leu Lys Ala Leu Lys Ala Ala Leu Lys
1               5                   10                  15

Leu Ala

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Arg Arg Arg Arg Arg Arg Arg
1               5

<210> SEQ ID NO 26
<211> LENGTH: 10
<212> TYPE: PRT
<213> ORGANISM: Unknown
<220> FEATURE:
<223> OTHER INFORMATION: Description of Unknown:
      Bacterial cell wall permeating peptide

<400> SEQUENCE: 26

Lys Phe Phe Lys Phe Phe Lys Phe Phe Lys
1               5                   10

<210> SEQ ID NO 27
<211> LENGTH: 37
<212> TYPE: PRT
<213> ORGANISM: Unknown
<220> FEATURE:
<223> OTHER INFORMATION: Description of Unknown:
      LL-37 peptide

<400> SEQUENCE: 27

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
        35

<210> SEQ ID NO 28
<211> LENGTH: 31
<212> TYPE: PRT
<213> ORGANISM: Unknown
<220> FEATURE:
<223> OTHER INFORMATION: Description of Unknown:
      Cecropin P1 peptide

<400> SEQUENCE: 28

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30

<210> SEQ ID NO 29
<211> LENGTH: 30
<212> TYPE: PRT
<213> ORGANISM: Unknown
<220> FEATURE:
<223> OTHER INFORMATION: Description of Unknown:
      Alpha-defensin peptide

<400> SEQUENCE: 29

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 30
<211> LENGTH: 36
<212> TYPE: PRT
<213> ORGANISM: Unknown
<220> FEATURE:
<223> OTHER INFORMATION: Description of Unknown:
      Beta-defensin peptide

<400> SEQUENCE: 30

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
        35

<210> SEQ ID NO 31
<211> LENGTH: 42
<212> TYPE: PRT
<213> ORGANISM: Unknown
<220> FEATURE:
<223> OTHER INFORMATION: Description of Unknown:
      PR-39 peptide

<400> SEQUENCE: 31

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro Gly Lys Arg

<210> SEQ ID NO 32
<211> LENGTH: 13
<212> TYPE: PRT
<213> ORGANISM: Unknown
<220> FEATURE:
<223> OTHER INFORMATION: Description of Unknown:
      Indolicidin peptide

<400> SEQUENCE: 32

Ile Leu Pro Trp Lys Trp Pro Trp Trp Pro Trp Arg Arg
1               5                   10

<210> SEQ ID NO 33
<211> LENGTH: 16
<212> TYPE: PRT
<213> ORGANISM: Unknown
<220> FEATURE:
<223> OTHER INFORMATION: Description of Unknown:
      RFGF peptide

<400> SEQUENCE: 33

Ala Ala Val Ala Leu Leu Pro Ala Val Leu Leu Ala Leu Leu Ala Pro
1               5                   10                  15

<210> SEQ ID NO 34
<211> LENGTH: 11
<212> TYPE: PRT
<213> ORGANISM: Unknown
<220> FEATURE:
<223> OTHER INFORMATION: Description of Unknown:
      RFGF analogue peptide

<400> SEQUENCE: 34

Ala Ala Leu Leu Pro Val Leu Leu Ala Ala Pro
1               5                   10

<210> SEQ ID NO 35
<211> LENGTH: 12
<212> TYPE: PRT
<213> ORGANISM: Unknown
<220> FEATURE:
<223> OTHER INFORMATION: Description of Unknown:
      Bactenecin peptide

<400> SEQUENCE: 35

Arg Lys Cys Arg Ile Val Val Ile Arg Val Cys Arg
1               5                   10

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aacaguguuc uugcucuaua a                                           21

<210> SEQ ID NO 37
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uuauagagca agaacacugu uuu                                           23

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
ugctctataa                                                          10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
ugcuctataa                                                          10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
ugctctataa                                                          10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
ugcucuauaa                                                          10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 42
ugcucuauaa                                                                10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
ugcucuauaa                                                                10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
ugcucuauaa                                                                10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ugcucuauaa                                                                10

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
uguucutgct ctataa                                                         16

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 47
ugcucuauaa                                                              10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
ugcucuauaa                                                              10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
tcacacucca                                                              10

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
ccauugtcac acucca                                                       16

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<223> OTHER INFORMATION: Description of Combined DNA/RNA Molecule:
      Synthetic oligonucleotide

<400> SEQUENCE: 51
uctatacgta                                                          10

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
uguucuugct ctataa                                                   16

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
tguucuugct ctataa                                                   16

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
ugcuctataa                                                          10
```